United States Patent
Rossen et al.

(10) Patent No.: US 11,324,779 B2
(45) Date of Patent: May 10, 2022

(54) INJECTABLE MICROTISSUE SYSTEMS, DEVICES, AND METHODS

(71) Applicant: THE TRUSTEES OF COLUMBIA UNIVERSITY IN THE CITY OF NEW YORK, New York, NY (US)

(72) Inventors: Ninna S. Rossen, Brooklyn, NY (US); Samuel K. Sia, New York, NY (US); Brian M. Gillette, Bronx, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 29 days.

(21) Appl. No.: 15/694,152

(22) Filed: Sep. 1, 2017

(65) Prior Publication Data

US 2018/0042970 A1 Feb. 15, 2018

Related U.S. Application Data

(63) Continuation-in-part of application No. PCT/US2015/063266, filed on Dec. 1, 2015.
(Continued)

(51) Int. Cl.
*A61K 35/44* (2015.01)
*C12N 5/071* (2010.01)
(Continued)

(52) U.S. Cl.
CPC ............ *A61K 35/44* (2013.01); *A61K 9/0019* (2013.01); *A61K 9/5063* (2013.01); *A61K 35/28* (2013.01);
(Continued)

(58) Field of Classification Search
None
See application file for complete search history.

(56) References Cited

U.S. PATENT DOCUMENTS 7,364,725 B1 4/2008 Flugelman
8,173,119 B2 5/2012 Tamarat et al.
(Continued)

FOREIGN PATENT DOCUMENTS

WO 2011156784 A1 12/2011
WO 2014026201 A1 2/2014
WO WO 2014/026201 * 2/2014

OTHER PUBLICATIONS

Park et al., World J. Stem Cells 6(1): 33-42 (2014).*
Baer, World J. Stem Cells 6(3): 256-265 (2014).*
Rouwkema et al., Tissue Eng. 12(9): 2685-2693 (2006).*
(Continued)

*Primary Examiner* — Erin M. Bowers
(74) *Attorney, Agent, or Firm* — Potomac Law Group, PLLC

(57) ABSTRACT

Spheroid microtissues that can mimic native tissue-like structure and function, spheroid production methods that are high-throughput, suitable for efficient production, maintainable over long-term culture, and/or offer repeatable control over size distribution. Spheroids that have blood vessels, including spheroids with functional, blood-perfused vascular networks upon injection in vivo. Dissolvable hydrogel microwell arrays for high throughput parallel formation of spheroids in a single pipetting step and easy retrieval for downstream applications. A method to produce prevascularized microtissues in sufficient numbers to form a macrotissue in vivo for therapeutic purposes. This method is based on sacrificial release of dissolvable microwell templates, a novel and scalable strategy which enables gentle harvesting of microtissues with control over size and composition. The method forms microtissues containing endothelial cells and mesenchymal stem cells, which are co-cultured under dynamic conditions and self-organize into blood-vessel units.

10 Claims, 42 Drawing Sheets
(17 of 42 Drawing Sheet(s) Filed in Color)

Related U.S. Application Data

(60) Provisional application No. 62/127,217, filed on Mar. 2, 2015.

(51) Int. Cl.
 *A61K 9/00* (2006.01)
 *A61K 9/50* (2006.01)
 *A61K 35/28* (2015.01)

(52) U.S. Cl.
 CPC ......... *C12N 5/0691* (2013.01); *C12N 5/0697* (2013.01); *C12N 2501/02* (2013.01); *C12N 2501/115* (2013.01); *C12N 2501/165* (2013.01); *C12N 2501/33* (2013.01); *C12N 2501/385* (2013.01); *C12N 2501/39* (2013.01); *C12N 2501/395* (2013.01); *C12N 2501/81* (2013.01); *C12N 2502/1352* (2013.01); *C12N 2502/1358* (2013.01); *C12N 2502/28* (2013.01); *C12N 2539/00* (2013.01)

(56) References Cited

U.S. PATENT DOCUMENTS

| | | |
|---|---|---|
| 8,846,307 B2 | 9/2014 | Neumann |
| 2007/0116674 A1 | 5/2007 | Casteilla et al. |
| 2008/0063716 A1 | 3/2008 | Moro et al. |
| 2010/0068793 A1 | 3/2010 | Ungrin et al. |
| 2011/0171712 A1 | 7/2011 | Rivron et al. |
| 2012/0083425 A1 | 4/2012 | George et al. |
| 2012/0129208 A1 | 5/2012 | Khine et al. |
| 2014/0369970 A1 | 12/2014 | Alfonso et al. |

OTHER PUBLICATIONS

Keim et al., J. Biotechnol. 118:213-229 (2005).*
Botham et al., "Clinical trials of adult stem cell therapy for peripheral artery disease," Methodist Debakey Cardiovasc J., 2013, 9(4): pp. 201-205.
Eng et al., "Assembly of complex cell microenvironments using geometrically docked hydrogel shapes", Proceedings of the National Academy of Sciences, Mar. 19, 2013, vol. 110(12), pp. 4551-4556.
Fleming et al., "Fusion of uniluminal vascular spheroids: a model for assembly of blood vessels," Developmental Dynamics, Feb. 2010, 239(2): pp. 398-406.
Hanjaya-Putra et al., "Integration and Regression of Implanted Engineered Human Vascular Networks During Deep Wound Healing", Stem Cells Translational Medicine, Mar. 13, 2013, vol. 2, pp. 297-306.
International Search Report and Written Opinion for International Application No. PCT/US2015/63266 dated Mar. 29, 2016.
Jiang et al., "Guided assembly of endothelial cells on hydrogel matrices patterned with microgrooves: a basic model for microvessel engineering," Soft Matter, 2013, 9: pp. 1113-1121.
Ogawa et al., "Vascular tissue engineering and vascularized 3D tissue regeneration," Regen. Med., 2007, 2(5): pp. 831-837.
Parsa, et al., "Uncovering the behaviors of individual cells within a multicellular microvascular community", PNAS, Mar. 22, 2011, vol. 108(12), pp. 5133-5138.
Raval et al., "Cell therapy of peripheral arterial disease: From experimental findings to clinical trials," Circ. Res., Apr. 2013, 112(9).
Tschoeke et al., "Tissue-engineered small-caliber vascular graft based on a novel biodegradable composite fibrin-polylactide scaffold," Tissue Engineering: Part A, 2009, 15(8): pp. 1909-1918.
Walser et al., "Generation of co-culture spheroids as vascularization units for bone tissue engineering," European Cells and Materials, 2013, 26: pp. 222-233.
Mironov et al., "Organ printing: from bioprinter to organ biofabrication line," Curr Opin Biotechnol, Oct. 2011, vol. 22(5), pp. 667-673.
Mironov et al., "Organ printing: Tissue spheroids as building blocks," Biomaterials, Apr. 2009, vol. 30(12), pp. 2164-2174.
Nam et al., "Biomimetic 3D Tissue Models for Advanced High-Throughput Drug Screening," J Lab Autom 20, 201-215 (2015).
Novosel et al., "Vascularization is the key challenge in tissue engineering," Adv Drug Deliv Rev, Apr. 30, 2011, vol. 33(4-5), pp. 300-311.
Okochi et al., "Three-dimensional cell culture array using magnetic force-based cell patterning for analysis of invasive capacity of BALB/3T3/v-src," Lab Chip, Sep. 23, 2009, vol. 9(23), pp. 3378-3384.
Ott et al., "Perfusion-decellularized matrix: using nature's platform to engineer a bioartificial heart," Nat Med 14, 213-221 (2008).
Ozawa et al., "Alginate gel microwell arrays using electrodeposition for three-dimensional cell culture," Lab Chip, May 13, 2013, vol. 13(15), pp. 3128-3135.
Palmer et al., "High-resolution in vivo imaging of fluorescent proteins using window chamber models," Methods Mol Biol, Mar. 31, 2012, vol. 872, pp. 31-50.
Pati et al., "Printing three-dimensional tissue analogues with decellularized extracellular matrix bioink," Nat Commun, Jun. 2, 2014, vol. 5, art. 3935.
Ponticorvo et al., "How to build a Laser Speckle Contrast Imaging (LSCI) system to monitor blood flow," JoVE, 2010, vol. 45, pp. 1-3.
Rouwkema et al., "Endothelial Cells Assemble into a 3-Dimensional Prevascular Network in a Bone Tissue Engineering Construct," Tissue Engineering, Sep. 22, 2006, vol. 12(9), pp. 2685-2693.
Sekine et al., "In vitro fabrication of functional three-dimensional tissues with perfusable blood vessels," Nat Commun 4, 1399 (2013).
Spence et al., "Directed differentiation of human pluripotent stem cells into intestinal tissue in vitro," Nature 470, 105-109 (2011).
Steffens et al., "In vivo engineering of a human vasculature for bone tissue engineering applications," J Cell Mol Med, Sep. 2009, vol. 13(9b), pp. 3380-3386.
Sun et al., "Vascularization strategies of engineered tissues and their application in cardiac regeneration," Adv Drug Deliv Rev, Jan. 15, 2016, vol. 96, pp. 183-194.
Sutherland et al., "Growth of multicell spheroids in tissue culture as a model of nodular carcinomas," J Natl Cancer Inst, Jan. 1, 1971, vol. 46(1), pp. 113-120.
Takasato et al., "Directing human embryonic stem cell differentiation towards a renal lineage generates a self-organizing kidney," Nat Cell Biol 16, 118-126 (2014).
Takebe et al., "Vascularized and functional human liver from an iPSC-derived organ bud transplant," Nature 499, 481-484 (2013).
Tan et al., "3D printing facilitated scaffold-free tissue unit fabrication," Biofabrication, Jun. 2014, vol. 6(2), art. 024111.
Tongers et al., "Therapeutic angiogenesis for critical limb ischemia: microvascular therapies coming of age," Circulation 118, 9-16 (2008).
Topeke et al., "PDMS absorption of small molecules and consequences in microfluidic applications," Lab Chip, Oct. 4, 2006, vol. 6(12), pp. 1484-1486.
Tung et al., "High-throughput 3D spheroid culture and drug testing using a 384 hanging drop array," Analyst, Oct. 21, 2010, vol. 136(3), pp. 473-478.
Verseijden et al., "Prevascular structures promote vascularization in engineered human adipose tissue constructs upon implantation," Cell Transplant, Mar. 26, 2010, vol. 19, pp. 1007-1020.
Wang et al., "Alginate encapsulation is a highly reproducible method for tumor cell implantation in dorsal skinfold chambers," BioTechniques, Dec. 2005, vol. 39(6), pp. 834-839.
Wenger et al., "Development and characterization of a spheroidal coculture model of endothelial cells and fibroblasts tor improving angiogenesis in tissue engineering," Cells Tissues Organs, Nov. 17, 2005, vol. 181(2), pp. 80-88.
White et al., "Implanted cell-dense prevascularized tissues develop functional vasculature that supports reoxygenation after thrombosis," Tissue Eng Part A, Jun. 27, 2014, vol. 20(17-18), pp. 2316-2328.
Yuhas et al., "A simplified method for production and growth of multicellular tumor spheroids," Cancer Res, Oct. 1977, vol. 37(10), pp. 3639-3643.

(56) References Cited

OTHER PUBLICATIONS

Zisch et al., "Cell-demanded release of VEGF from synthetic, biointeractive cell ingrowth matrices for vascularized tissue growth," FASEB Journal, Dec. 2003, vol. 17(15), pp. 2260-2262.
"Peripheral Arterial Disease (PAD) Fact Sheet," US Centers for Disease Control and Prevention, https://www.cdc.gov/dhdsp/data_statistics/fact_sheets/fs_PAD.htm.
Akiyama et al., "Periosteal cell pellet culture system: a new technique for bone engineering," Cell Transplant, Jan. 9, 2006, vol. 15, pp. 521-532.
Alajati et al., "Spheroid-based engineering of a human vasculature in mice," Nat Methods, May 2008, vol. 5(5), pp. 439-445.
Benoit et al., "Safety and efficacy of autologous cell therapy in critical limb ischemia: a systematic review," Cell Transplant 22, 545-562 (2013).
Black et al., "F.A. In vitro reconstruction of a human capillary-like network in a tissue-engineered skin equivalent," FASEB J 12, 1331-1340 (1998).
Boas et al., "Laser speckle contrast imaging in biomedical optics," J Biomed Opt, Jan.-Feb. 2010, vol. 15(1), art. 011109.
Bosiers et al., "Endovascular Therapy as the Primary Approach for Limb Salvage in Patients with Critical Limb Ischemia: Experience with 443 Infrapopliteal Procedures," Vascular, Apr. 1, 2006, vol. 14(2), pp. 63-69.
Brenes et al., "Toward a mouse model of hind limb ischemia to test therapeutic angiogenesis," J Vasc Surg, Dec. 2012, vol. 56(6), pp. 1669-1679.
Briers et al., "Laser Doppler, speckle and related techniques for blood perfusion mapping and imaging," Physiol. Meas., Oct. 29, 2001, vol. 22(4), pp. R35-R66.
Chen et al., "High-Throughput Cancer Cell Sphere Formation for Characterizing the Efficacy of Photo Dynamic Therapy in 3D Cell Cultures," Sci Rep, Jul. 8, 2015, vol. 5, art. 12175.
Chen et al., "Paracrine factors of mesenchymal stem cells recruit macrophages and endothelial lineage cells and enhance wound healing," PLoS One 3, e1886 (2008).
Chung et al., "Injectable cellular aggregates prepared from biodegradable porous microspheres for adipose tissue engineering," Tissue Eng Part A, Oct. 23, 2008, vol. 15(6), pp. 1391-1400.
Clark et al., "Microscopic observations on the growth of blood capillaries in the living mammal," American journal of anatomy, Mar. 1939, vol. 64, pp. 251-301.
Davies, "Critical limb ischemia: epidemiology," Methodist DeBakey Cardiovasc J 8, 10-14 (2012).
Dimmeler et al., "A. Translational strategies and challenges in regenerative medicine," Nat Med 20, 814-821 (2014).
Dissanayaka et al., "Scaffold-free Prevascularized Microtissue Spheroids for Pulp Regeneration," J Dent Res, Dec. 2014, vol. 93(12), pp. 1296-1303.
Ehsan et al., "A three-dimensional in vitro model of tumor cell intravasation," Integr Biol (Camb), Jun. 2014, vol. 6(6), pp. 603-610.
Feiring et al., "Preventing leg amputations in critical limb ischemia with below-the-knee drug-eluting stents: the PaRADISE (Preventing Amputations using Drug eluting StEnts) trial," J Am Coll Cardiol, Apr. 2010, vol. 55(15), pp. 1580-1589.
Fennema et al., "Spheroid culture as a tool for creating 3D complex tissues," Trends Biotechnol, Feb. 2013, vol. 31(2), pp. 108-115.
Frey et al., "Reconfigurable microfluidic hanging drop network for multi-tissue interaction and analysis," Nat Commun, Jun. 30, 2014, vol. 5, art. 4250.
Gillette et al., "Engineering extracellular matrix structure in 3D multiphase tissues," Biomaterials, Nov. 2011, vol. 32(23), pp. 8067-8076.
Gillette et al., "In situ collagen assembly for integrating microfabricated three-dimensional cell-seeded matrices," Nat Mater, Aug. 2008, vol. 7, pp. 636-640.
Goto et al., "Search for appropriate experimental methods to create stable hind-limb ischemia in mouse," Tokai J Exp Clin Med, Sep. 20, 2006, vol. 31(3), pp. 128-132.
Greggio et al., "Artificial three-dimensional niches deconstruct pancreas development in vitro," Development 140, 4452-4462 (2013).
Griffin et al., "Accelerated wound healing by injectable microporous gel scaffolds assembled from annealed building blocks," Nat Mater, Jul. 2015, vol. 14(7), pp. 737-744.
Haraguchi et al., "Fabrication of functional three-dimensional tissues by stacking cell sheets in vitro," Nature Protocols 7, 850-858 (2012).
Huang et al., "Mesenchymal stem cells promote growth and angiogenesis of tumors in mice," Oncogene, Sep. 12, 2013, vol. 32, pp. 4343-4354.
Huebsch et al., "Matrix elasticity of void-forming hydrogels controls transplanted-stem-cell-mediated bone formation," Nat Mater, Dec. 2015, vol. 14(12), pp. 1269-1277.
Iwase et al., "Comparison of angiogenic potency between mesenchymal stem cells and mononuclear cells in a rat model of hindlimb ischemia," Cardiovasc Res, Jun. 1, 2005, vol. 66(3), pp. 543-551.
Jeong et al., "Viscoelastic lithography for fabricating self-organizing soft micro-honeycomb structures with ultra-high aspect ratios," Nat Commun, May 9, 2016, vol. 7, art. 11269.
Kang et al., "A 3D bioprinting system to produce human-scale tissue constructs with structural integrity," Nat Biotechnol, Feb. 15, 2016, vol. 34, pp. 312-319.
Kim et al., "Vascularization of three-dimensional engineered tissues for regenerative medicine applications," Acta Biomater, Sep. 1, 2016, vol. 41, pp. 17-26.
Kolesky et al., "3D Bioprinting of Vascularized, Heterogeneous Cell-Laden Tissue Constructs," Adv. Mater, May 21, 2014, vol. 26(19), pp. 3124-3130.
Kolesky et al., "Three-dimensional bioprinting of thick vascularized tissues," Proc Natl Acad Sci USA, Mar. 22, 2016, vol. 113(12), pp. 3179-3184.
Lancaster et al., "Cerebral organoids model human brain development and microcephaly," Nature 501, 373-379 (2013).
Laschke et al., "The dorsal skinfold chamber: window into the dynamic interaction of biomaterials with their surrounding host tissue," European cells & materials, Sep. 20, 2011, vol. 22, pp. 147-164.
Lawall et al., "Treatment of peripheral arterial disease using stem and progenitor cell therapy," J Vasc Surg 53, 445-453 (2011).
Lee et al., "Lung stem cell differentiation in mice directed by endothelial cells via a BMP4-NFATc1-thrombospondin-1 axis," Cell 156, 440-455 (2014).
Leong et al., "Patterned prevascularised tissue constructs by assembly of polyelectrolyte hydrogel fibres," Nat Commun 4, 2353 (2013).
Li et al., "PDMS Compound Adsorption in Context," J Biomol Screen, Feb. 1, 2009, vol. 14(2), pp. 194-202.
Liu et al., "Functional three-dimensional HepG2 aggregate cultures generated from an ultrasound trap: comparison with HepG2 spheroids," J Cell Biochem, Dec. 1, 2007, vol. 102(5), pp. 1180-1189.
Liu et al., "Quasi-spherical microwells on superhydrophobic substrates for long term culture of multicellular spheroids and high throughput assays," Biomaterials, Jul. 2014, vol. 35(23), pp. 6060-6068.
Lokmic et al., "An arteriovenous loop in a protected space generates a permanent, highly vascular, tissue-engineered construct." FASEB J 21, 511-522 (2007).
Lovett et al., "Vascularization strategies for tissue engineering," Tissue engineering, Part B, Reviews 15, 353-370 (2009).
Mazza et al., "Decellularized human liver as a natural 3D-scaffold for liver bioengineering and transplantation," Sci Rep, Aug. 7, 2015, vol. 5, art. 13079.
Metzger et al., "The liquid overlay technique is the key to formation of co-culture spheroids consisting of primary osteoblasts, fibroblasts and endothelial cells," Cytotherapy, Sep. 2011, vol. 13(11), pp. 1000-1012.
Meyer et al., "Cartilage defect regeneration by ex vivo engineered autologous microtissue—preliminary results," In Vivo, Jan. 12, 2012, vol. 26, 251-257.

(56) References Cited

OTHER PUBLICATIONS

Miller et al., "Rapid casting of patterned vascular networks for perfusable engineered three-dimensional tissues," Nat Mater 11, 768-774 (2012).
Mirabella et al., "3D-printed vascular networks direct therapeutic angiogenesis in ischaemia," Nature Biomedical Engineering, Jun. 13, 2017, vol. 1, art. 0083.
Minar, "Critical limb ischaemia," Hamostaseologie, Jan. 2009, vol. 29(1), pp. 102-109.
Sasagawa et al., "Design of prevascularized three-dimensional cell-dense tissues using a cell sheet stacking manipulation technology," Biomaterials, vol. 31, pp. 1646-1654, 2010.
Yap et al., "Enhanced liver progenitor cell survival and differentiation in vivo by spheroid implantation in a vascularized tissue engineering chamber," Biomaterials, vol. 34, No. 16, pp. 3992-4001, May 2013.

* cited by examiner

FIG. 3A
w/o VEGF
FIG. 3B
with VEGF
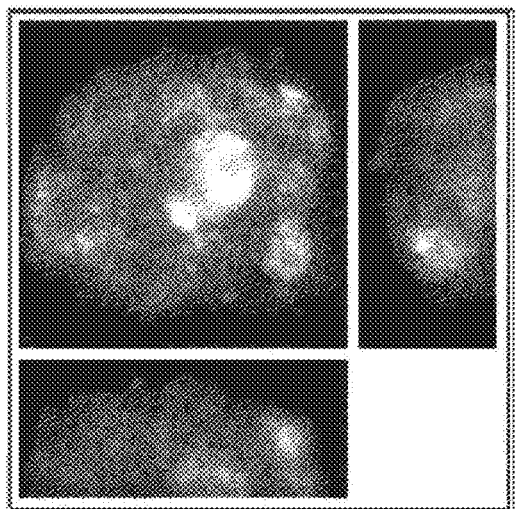
Day 3
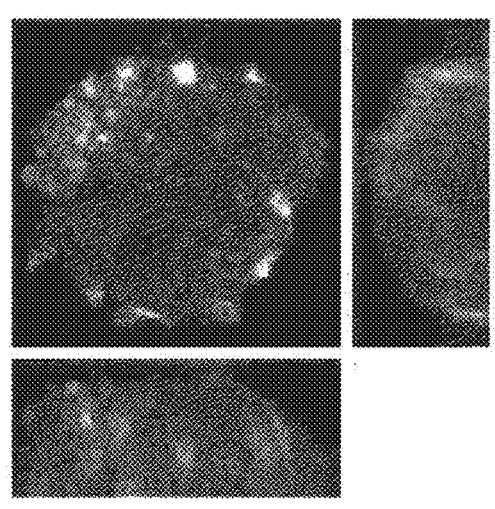
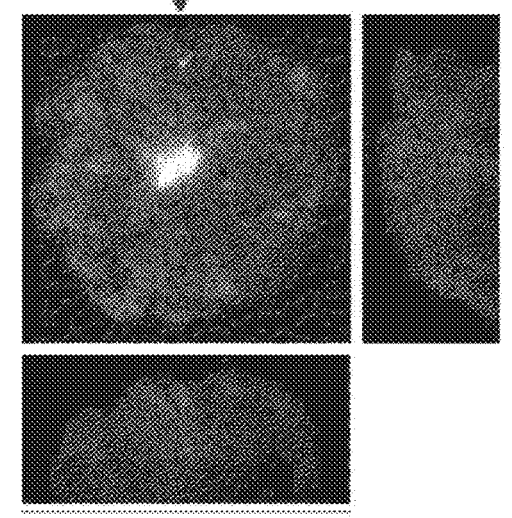
Day 10
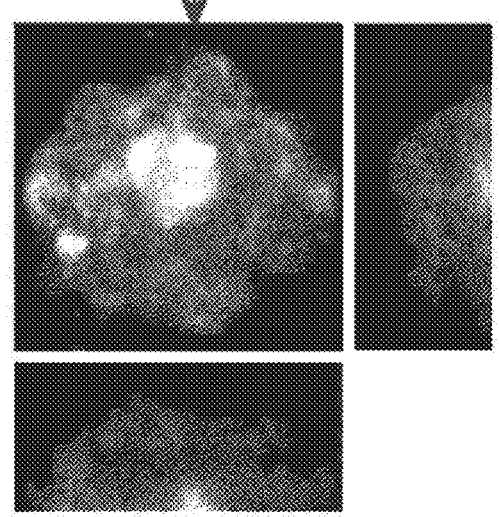
FIG. 3C
FIG. 3D

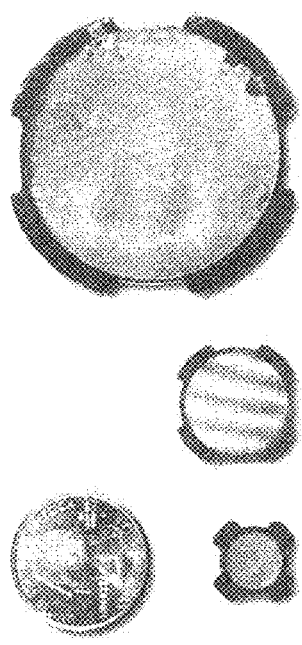
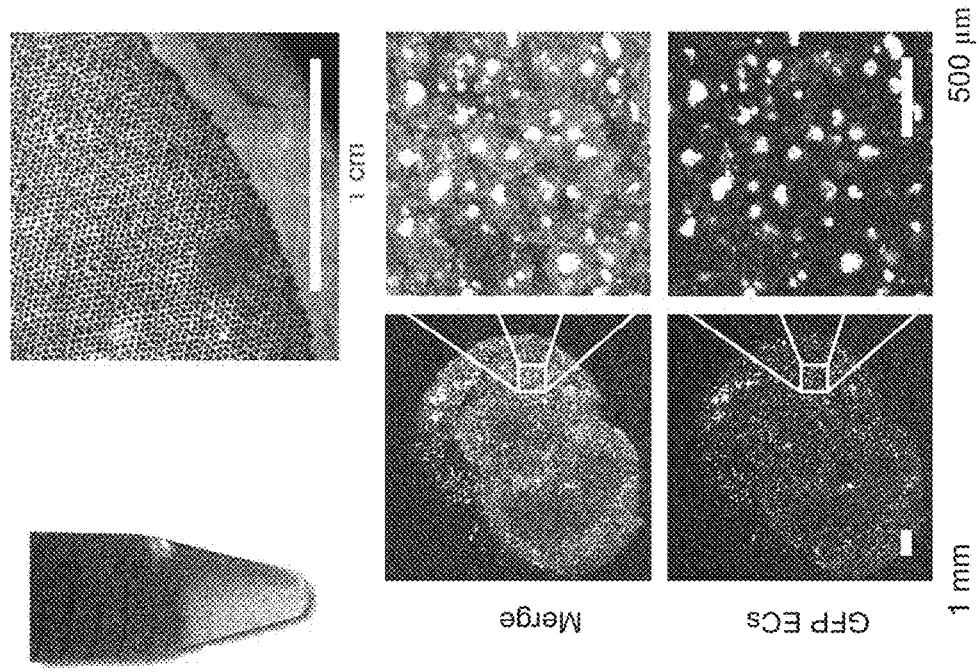
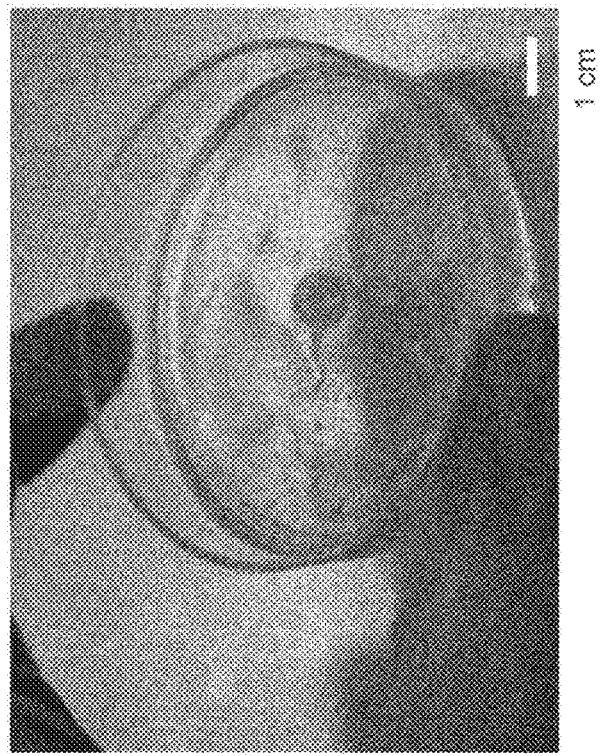
FIG. 14A  FIG. 14B  FIG. 14C  FIG. 14D (8 in vivo + 8 in vitro)  FIG. 14E  FIG. 14F FIG. 16A
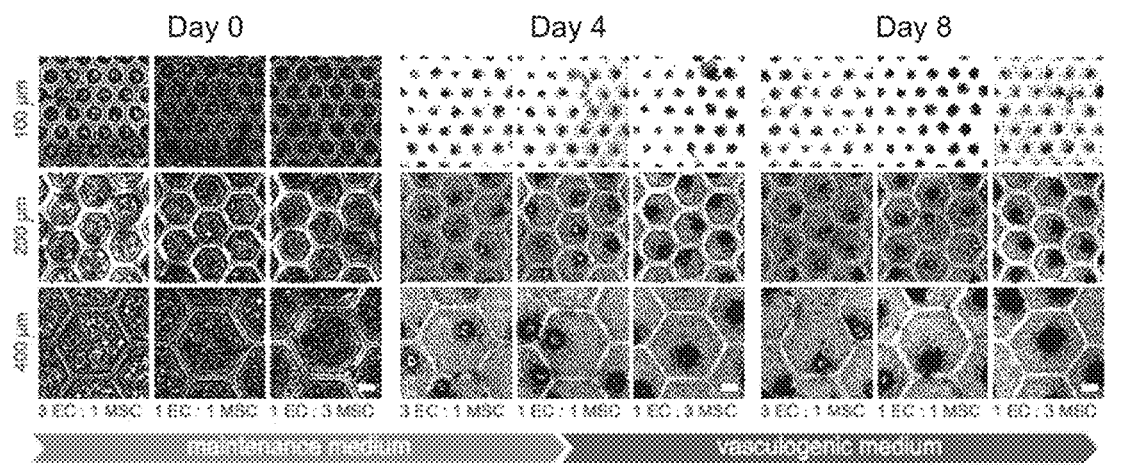
FIG. 16B
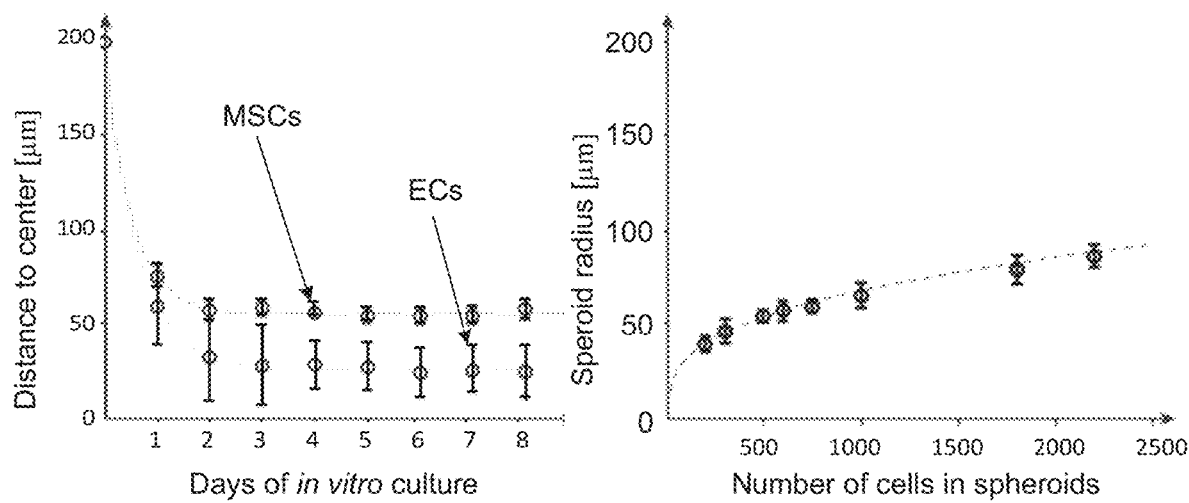
FIG. 16C FIG. 17A
FIG. 17B
FIG. 17C
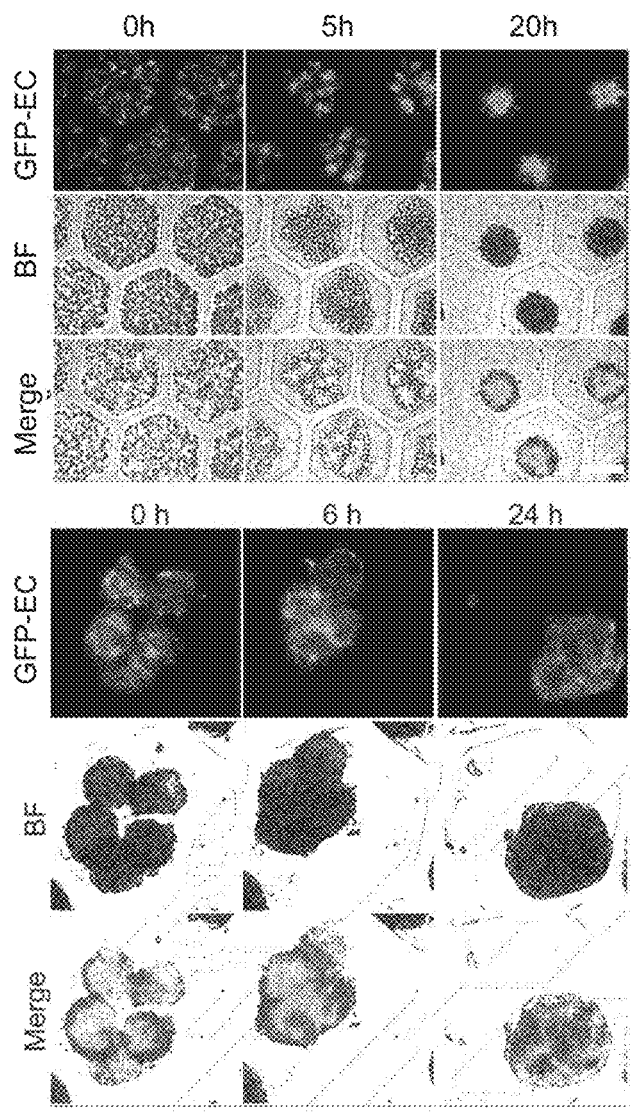
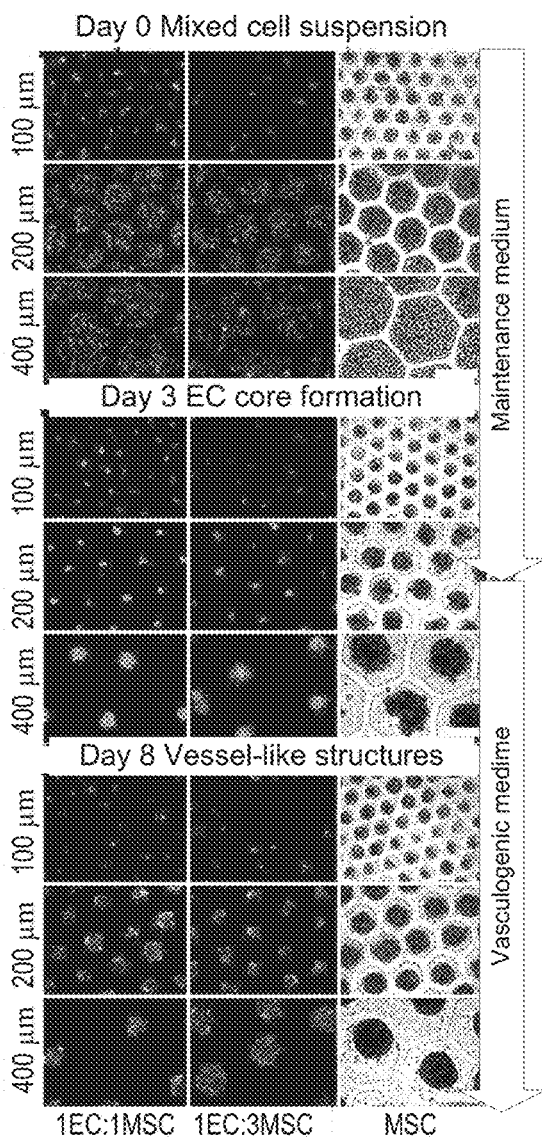

FIG. 18A
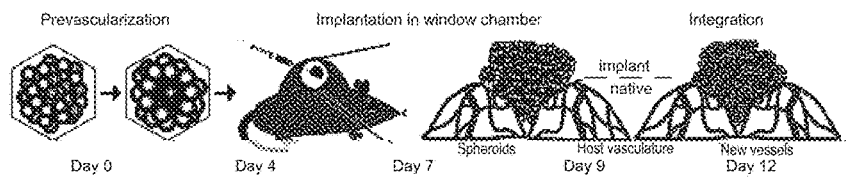
FIG. 18B
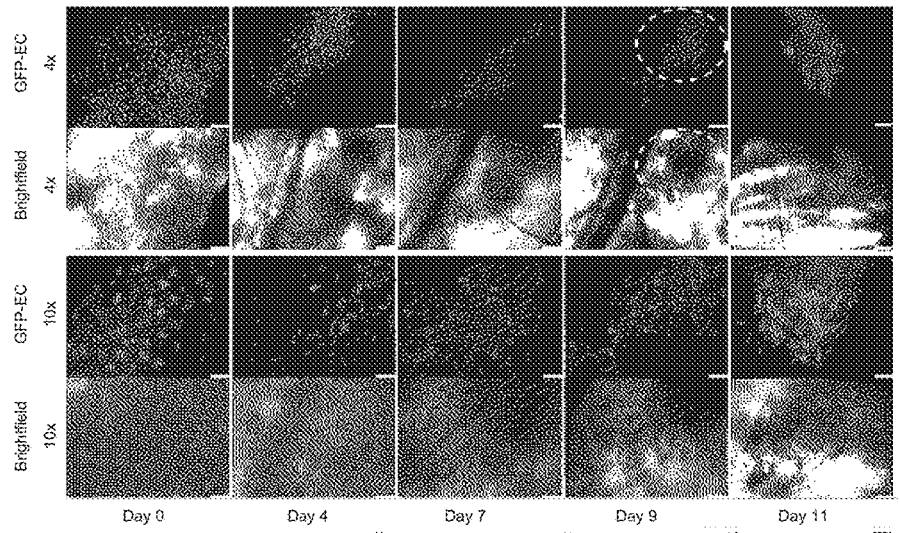
FIG. 18C
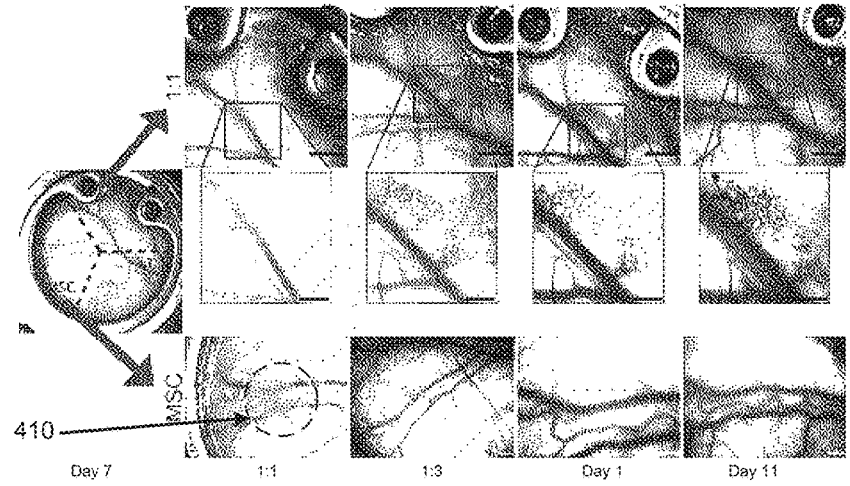
FIG. 18D
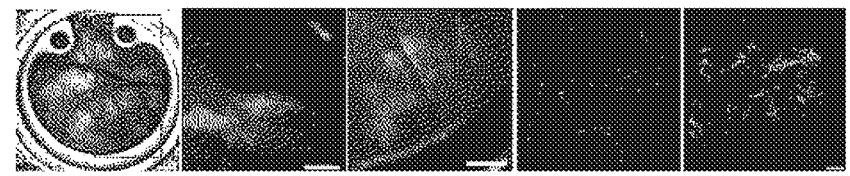
FIG. 18E

FIG. 20B
FIG. 20A
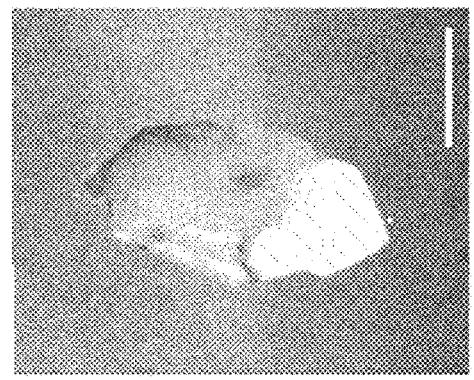
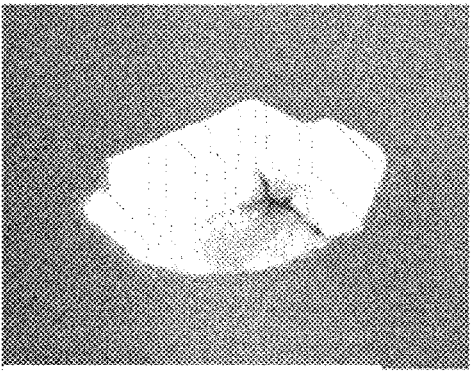
FIG. 20C

Not injected

Injected with 27 gauge (210 μm inner diameter)

Injected with 30 gauge (210 μm inner diameter)

FIG. 26A
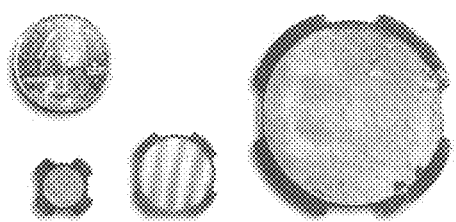
FIG. 26B
FIG. 26C
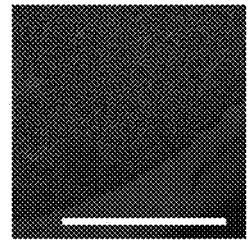
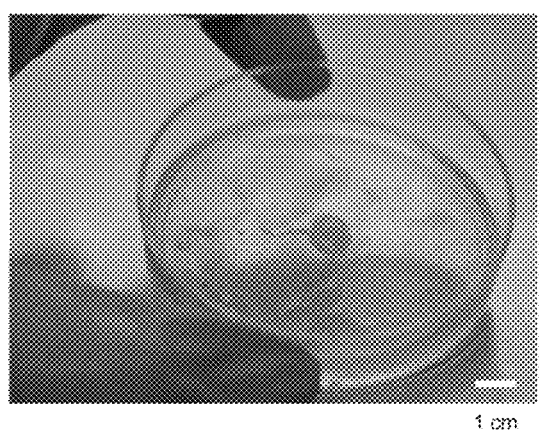
FIG. 26D
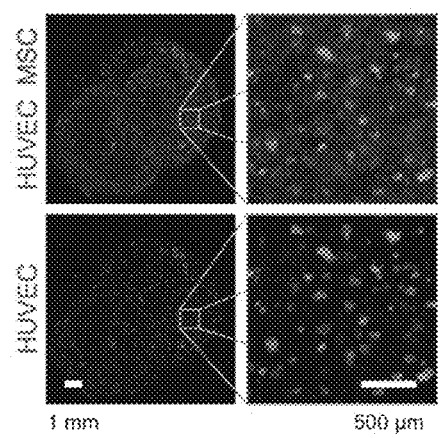
FIG. 26E

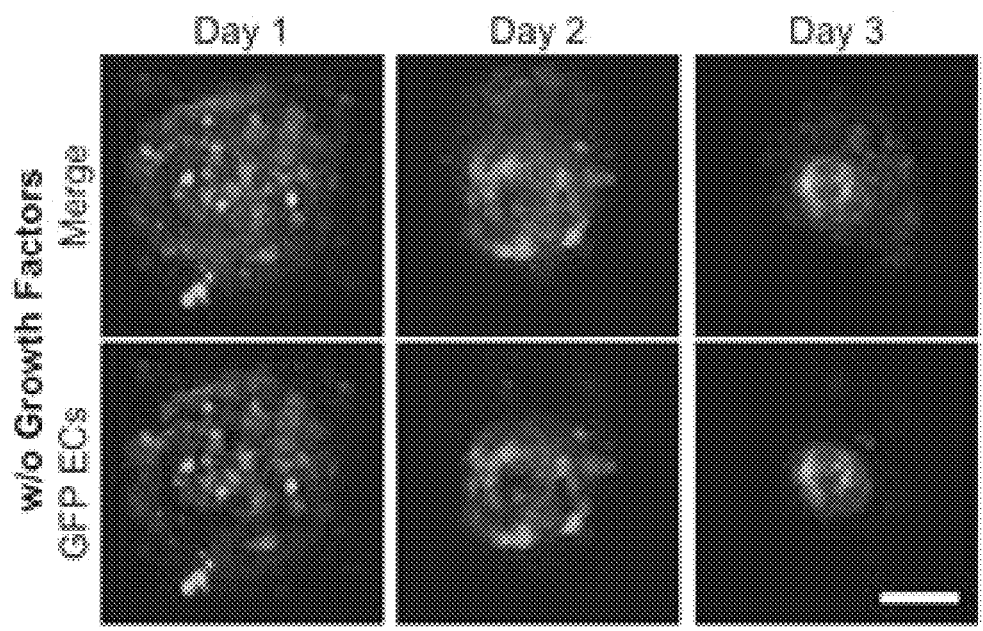
FIG. 27A
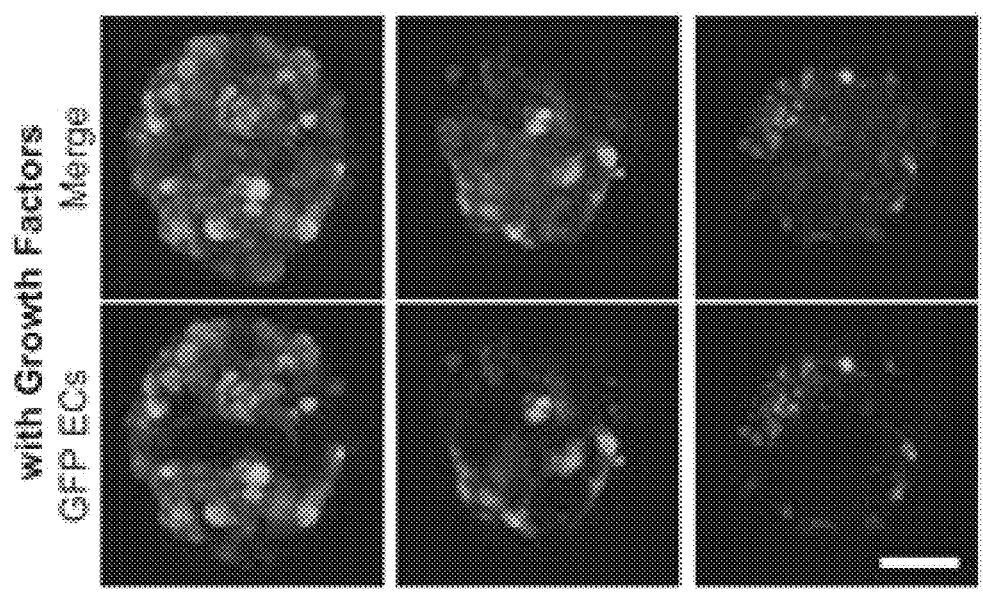
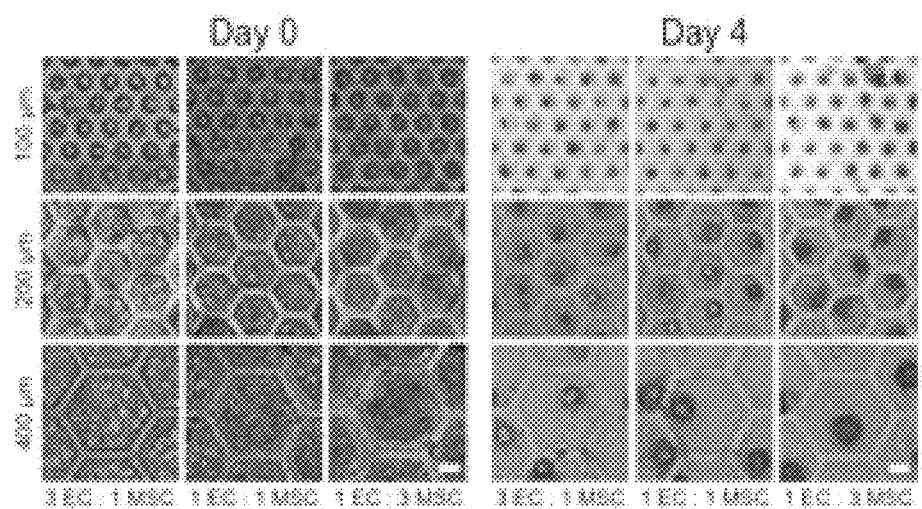
FIG. 27B

FIG. 29A
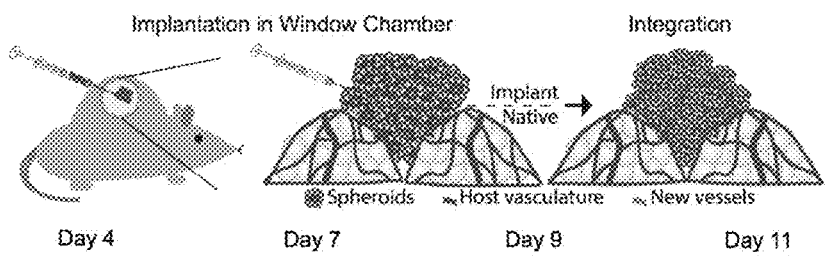
FIG. 29B
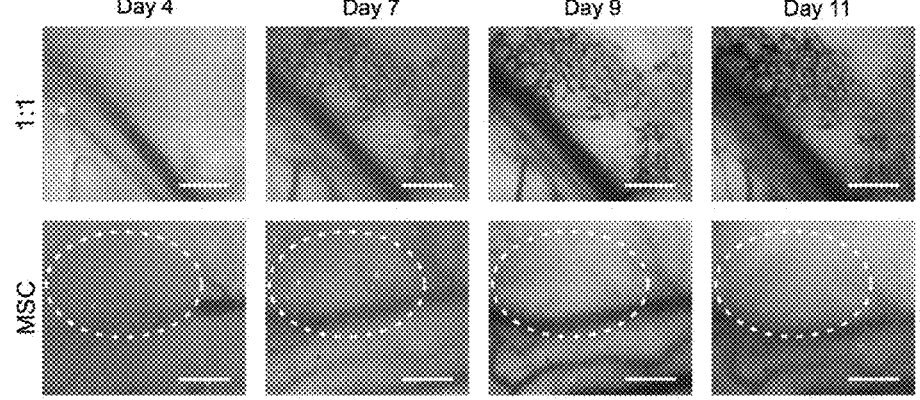
FIG. 29C
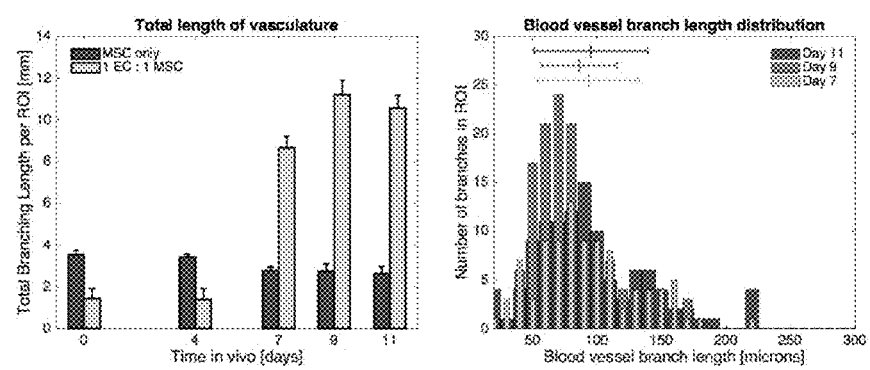
FIG. 29D
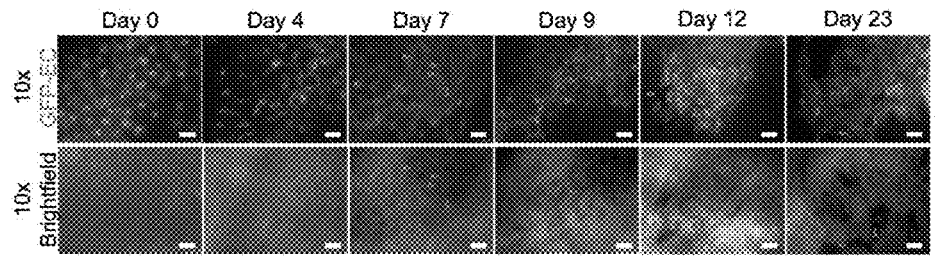
FIG. 29E FIG. 30A
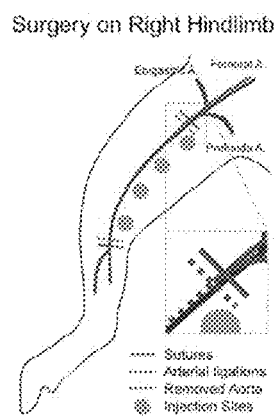
FIG. 30C
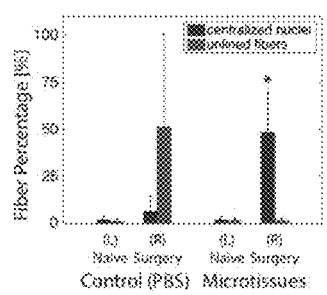
FIG. 30E
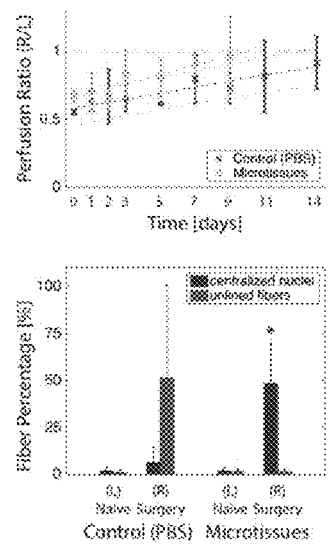
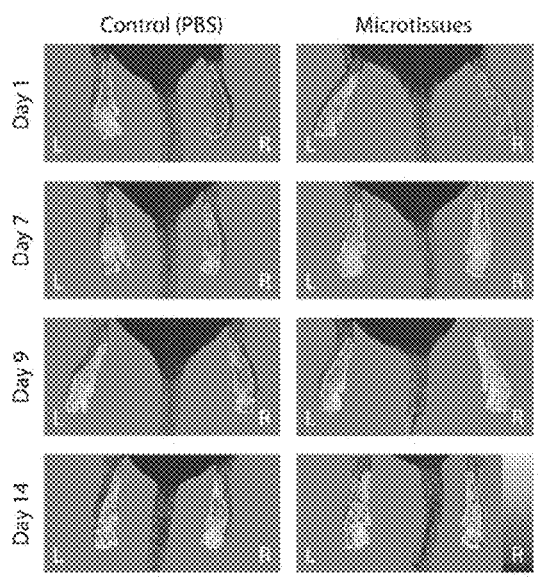
FIG. 30B
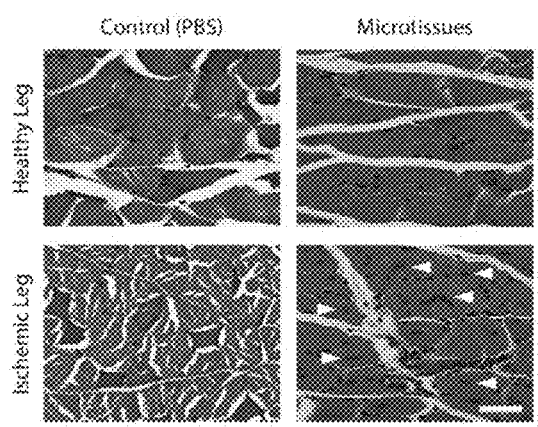
FIG. 30D FIG. 38A 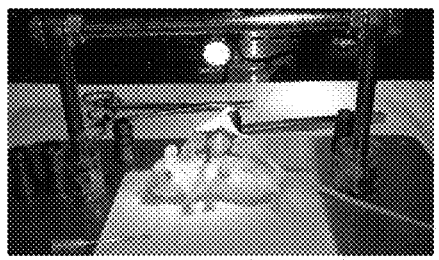 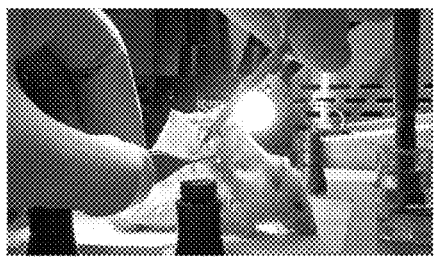 FIG. 38B
FIG. 38C 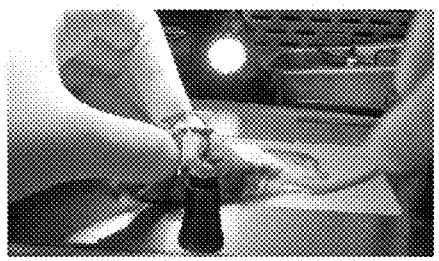 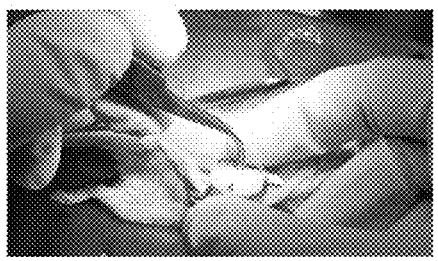 FIG. 38D
FIG. 38E 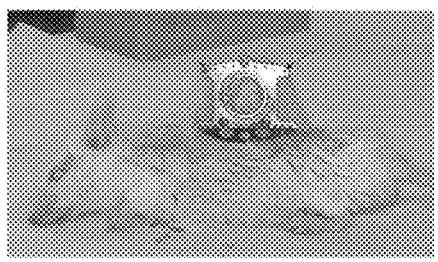 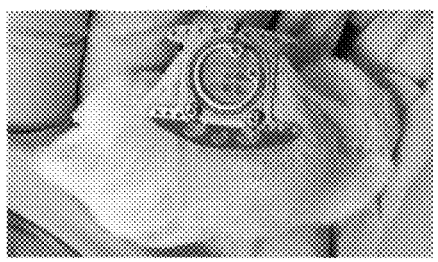 FIG. 38F not injected injected with 27 gauge
(210 µm inner diameter)

injected with 30 gauge
(159 µm inner diameter)

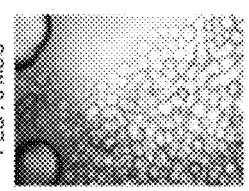 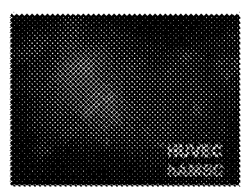 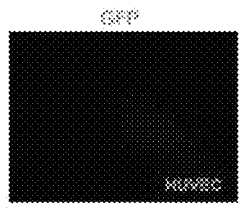 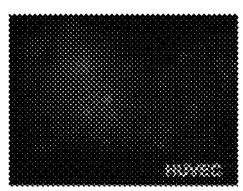
FIG. 40D

| Cell Aggregate Production Method | High throughput | Output (no. of cell aggregates) | Easy automation (Liquid handling in all steps) | Size control | Continuous observation | Easy harvesting | Biologically inert process suitable for in vivo use | Publication |
|---|---|---|---|---|---|---|---|---|
| dissolvable microwells | ++ | 10,000s per mold | + | + | + | + | + | Rossen et al. (2017) |
| microwell | + | 1,000s per mold | - | + | + | - | +/- | [43], [53], [61], & [62] |
| microwells within a microfluidic chip | + | 1,800s per microfluidic chip | - | + | ++ | - | + | [60] |
| hanging drops | - | 384 per culture plate | + | + | - | + | + | [54] |
| hanging drops in a microfluidic network | - | 16 per microfluidic chip | + | + | - | + | + | [55] |
| non-adhesive wells | + | 96 per culture plate | + | - | - | + | + | [56], [58], & [59] |
| spinner culture | + | 1,000s per spinner flask | + | - | + | - | + | [46] |
| ultrasound wave trap | - | 1 pellet per 2.5 mm tube | - | + | + | - | - | [48] |
| magnetic field | + | 1,800s per culture plate | - | + | - | - | - | [49] |
| clonal growth on soft agar | + | 1,000s per culture plate | - | - | - | - | + | [57] |

FIG. 42

INJECTABLE MICROTISSUE SYSTEMS, DEVICES, AND METHODS

STATEMENT REGARDING FEDERALLY SPONSORED RESEARCH

This invention was made with government support under R01HL095477 and 341/300-123012 awarded by the National Institutes of Health (NIH). The government has certain rights in the invention.

FIELD

The present disclosure relates generally to tissue engineering, and, more particularly, to injectable microtissues.

BACKGROUND

Spheroid microtissues—small aggregates of cells produced in vitro—can mimic the structure and function of native tissues, and are useful for a range of research and clinical applications, including regenerative medicine, in vitro drug screening, and in vivo tissue transplants. Spheroids form when multiple individual cells aggregate and then adhere to each other more strongly than surrounding materials, resulting in formation of a sphere-shaped cluster. Although a wide variety of methods have been developed to produce spheroids, current approaches lack simplicity.

Challenges in this area include production issues such as size distribution and vascularization after injection or implantation. The hanging-drop method, in which a small droplet of cells placed on the lid of a petri dish and inverted to cause aggregation at the bottom of the drop is commonly used. Seeding cells on non-adhesive 2D cell culture ware and guiding cells into a cluster by centrifugation, a standing ultrasound wave or a magnetic field are also used. Other methods for producing spheroids include seeding cells in spinner cultures. Macroporous carriers and microcarriers such as Cultispher-S with aggregation up to microspheres in spinner flasks, or coating the surface of polymer microspheres with cells are also known.

Vascularization, injectability, and other issues are important challenges for regenerative medicine. In vivo, most cells are found no more than 200 μm from the nearest capillary, which reflects the diffusion limit of oxygen. In order to create a larger tissue, a functional vascular network must be included to overcome the mass transfer limitations in the design of tissues engineered in vitro. Known approaches for vascularization include in vitro methods such as stacking endothelial cell layers between other cell sheets, scaffold guided endothelial co-culture, scaffold functionalization, and in vivo systems such as the arteriovenous loop chamber. In vivo approaches may rely on host blood vessel invasion of an avascular implant, which is slow and limited to several tenths of micrometers per day.

Effective methods to promote vascularization are crucial in tissue engineering and regenerative medicine, as well as treatment of ischemic pathologies. For engineered tissues, previous strategies included avascular or pre-vascularized scaffolds, but these approaches were limited by scaffold incompatibility or relied on host infiltration of blood vessels which is slow (limited to a few tenths of micrometers per day). Surgical approaches such as arteriovenous loop chamber also relied on invasion from host blood vessels. Emerging in vitro strategies included assembly of endothelial cell-laden hydrogel fibers or layers, but these approaches can be labor-intensive or difficult to scale up, and usually require invasive surgery if delivered as large pre-vascularized tissues.

There is also a need for novel methods to re-vascularize ischemic tissues. For example, peripheral artery disease (PAD) is the development of atherosclerotic plaque in the lower extremity arterial circulation resulting in varying levels of ischemia. The most severe form of the disease, critical limb ischemia (CLI) can lead to amputations and mortality rates of 25% within a year of surgery 24 and 60% within five years. Cases of CLI cost over 50,000 per patient per year, with direct billing of 25 billion per year in the U.S. One emerging approach for treatment is injections of mesenchymal stem cells (MSCs), which can potentially aid vascular regeneration by recruiting endothelial cells (ECs) and endothelial progenitor cells, but such approaches have not yet shown significant new re-perfusion. Injections of suspensions of ECs could promote assembly of vascular networks in vivo, but this method is heavily dependent on the state of injected cells while they are in the body; for example, the cells could die from prolonged deprivation of oxygen and nutrients. Implanting vascular patches with EC-lined lumens has been shown to increase collateral circulation in murine hindlimb ischemia models, but may not be applicable to clinical settings as they would require invasive surgery in ischemic sites with impaired wound healing.

Microtissues are three-dimensional multicellular aggregates (sometimes referred to as spheroids or organoids) which mimic the structure and function of native tissues and are useful for various research and clinical applications, including in vitro developmental research, drug screening, and in vivo tissue transplants. Several approaches for producing microtissues. Some of these include culturing cells in spinner cultures, using centrifugation, ultrasound wave 48 or magnetic field. However, these approaches offer little control over sizes of the microtissues, are difficult to continuously observe, are unsuitable for in vivo implantation, and may impair cell function or survival due to harsh handling. Macroporous gels, carriers, microspheres, or micro-honeycomb structures can be made in a gentler fashion, but their ECM composition is fixed and may not be generalizable to different cell types 5. Other approaches seed cells in hanging drops or in non-adhesive wells, but even with automated media exchange, this approach is low-throughput and limited to culturing 384 microtissues on a well-plate area. Other approaches include PDMS-based microchannels, and microwells with non-adhesive coating or material, but they exhibit limitations. For example, PDMS adsorbs many molecules (steroid hormones, hydrophobic small molecules and drugs) which could affect culture conditions and downstream assays. Moreover, harvesting microtissues from these structures requires inverting or disassembling the device and washing all components to collect the microtissues, a procedure which can be harsh, inefficient, and labor-intensive.

BRIEF DESCRIPTION OF DRAWINGS

The patent or application file contains at least one drawing executed in color. Copies of this patent or patent application publication with color drawing(s) will be provided by the Office upon request and payment of the necessary fee.

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

FIG. 3A is an image of an endothelial cell spheroid in a microwell after 3 days culture in a media without growth factors VEGF and bFGF, according to one or more embodiments of the disclosed subject matter.

FIG. 3B is an image of an endothelial cell spheroid in a microwell after 3 days culture in a media with growth factor VEGF.

FIG. 3C is an image of an endothelial cell spheroid in a microwell after 10 days culture in a media without growth factors VEGF and bFGF, according to one or more embodiments of the disclosed subject matter.

FIG. 3D is an image of an endothelial cell spheroid with endothelial core that is induced to mature and produce a lumen and/or sprout by addition of growth factors added to the media after the endothelial cores have formed, according to one or more embodiments of the disclosed subject matter.

FIGS. 14A-14F show a schematic diagram and results of a spheroid fabrication method using (FIGS. 14A-B) the same steps as illustrated in FIG. 13 to form 1000, 3000 or 30,000 spheroids depending on the size of the alginate construct; (FIG. 14C) 250,000,000 cells to be seeded on alginate microwells for massive high throughput; (FIG. 14D) Cells seeded in the 60 mm construct with 30,000 wells to create 30,000 spheroids. Scale bar is 1 cm; (FIG. 14E) Collecting the 30,000 mature spheroids will create a macro-tissue with an area of 1 cm$^2$ and a height of 1 mm Scale bar is 1 cm; (FIG. 14F) The spheroids are closely packed and all with endothelial cores in the macro-tissues. Scale bars are 1 mm and 500 μm in close-up.

FIGS. 16A-16C show endothelial cores formed by directed self-organization of the cells through timed exposure to growth factors. (FIG. 16A) The method can produce a large array of spheroids of different sizes (formed in microwells with either 100, 200 or 400 μm diameter) and with different endothelial core sizes (formed by different ratios of endothelial cells to mesenchymal stem cells (EC:MSC)). All spheroids in these arrays show the endothelial core formation after culture in maintenance medium, and maturation of these cores after culture in vasculogenic medium. (FIG. 16B) The contraction of the cells into spheroids (upper curve) and formation of endothelial cores (lower curve) as illustrated by the maximum radial distance of MSCs and ECs from the center of the spheroids (n>20) for each day of culture in (FIG. 16A). (FIG. 16B) The method can control the size of spheroids because it allows a specific number of cells to be adjacent. Spheroid diameter over time for spheroids containing different number of cells. (FIG. 16C) Spheroid diameter as a function of the number of cells they contain. With the fitted function of $r=(6/\pi$ (vcell ncell) $1/3/2$.

FIGS. 17A-17C) Early development of spheroid of 1 human ECs to 1 human MSCs in the first 20 hours (between Day 0 and Day 1) in 400 μm microwell. Shown are brightfield, GFP ECs and merge images. (FIG. 17B) In vitro formation of spheroid and vasculature of human ECs and MSCs under nine conditions (EC:MSC ratio and well size). Overlay of fluorescence: GFP ECs and MSCs. Shown are the spheroids immediately after seeding, after 3 days of culture in maintenance medium, and after 8 days of culture, the last 5 days with vasculogenic factors. (FIG. 17C) Spheroid fusion. Shown are spheroids of 1:1 and 1:3 HUVEC to MSC ratio that were formed and prevascularized in 200 um microwells for 9 days with last 6 days in vasculogenic medium. To mimic an in vivo environment, which is adhesive for cells, spheroids were placed in collagen-alginate microwell. Displayed are brightfield, GFP-EC and merge images of first 24 h of spheroid fusion. Scale bar=200 µm.

FIGS. 18A-18E show the vascular formation of injecting spheroids in vivo. (FIG. 18A) shows the experimental set up. Spheroids were formed and prevascularized in vitro, implanted in a window chamber on a SCID mouse and vascular formation and integration was observed. (FIG. 18B) shows the kinetics of vessel formation; Spheroids at different time points in vivo, cultivated in 200 µm microwell, GFP-Huvec:MSC=1:1; Prior in vitro cultivation: 3d in maintenance medium followed by 6d in vasculogenic medium; Arrow heads point at blood filled vessels. Dotted line encircles newly formed lumenous vessels. Scale bar=250 µm. (FIG. 18C) Stereoscopic images at different time points in vivo. Top row shows 1 Huvec:1 MSC spheroids. Square shows implants. Newly formed vessels are blood filled and functional. Day 7 is the first time blood in vessels was observed. Bar in top row=1.25 mm Bar in middle row=0.5 mm Bottom row shows pure MSC spheroids. No signs of vascularization were observed. Dotted line encircles implant. Bar in bottom row=0.5 mm (FIG. 18D) Day 7, newly formed, blood filled vessels colocalize with GFP signal from implants. Scale bar=1.25 mm (FIG. 18E) Spheroids in 9 well insert in vivo (FIG. 24F). 1 GFP-Huvec:1 MSC spheroids, formed and prevascularized in 200 µm microwells. Shown are maximum projection images of confocal Z-stack GFP-Huvec images. Z-stack at day 11=172 µm in 32 slices. Individual spheroids on day 1 form dense vascular network until day 11. Spatial control in vivo is exerted through 9 well insert. Scale bar=200 µm.

FIGS. 19A-19F show the fabrication of alginate-based micro-wells. FIG. 19A shows six cross-linked alginate microwell constructs in the PDMS mold with the top three constructs removed. FIGS. 19B-19D) The alginate molds are carefully loosened with a pair of sterile tweezers and removed from the mold holding on only to the "wings" to preserve the microwell structures in the middle. FIG. 19E) The alginate constructs must be flipped to expose the microwells before being placed in the well plate (FIG. 19F).

FIGS. 20A-20D show injecting the spheroids in vivo. (FIG. 20A) Injecting a solution with spheroids (endothelial ratio 1:3 and size 200 µm) into the adipose tissue of the obliques. A small incision along the back was made to ensure the correct position of the injection site. (FIG. 20B) The mice were sacrificed and the entire obliques (white dashed circle) were excised after 18 days of implantation. Black scale bar is 20 mm and the white scale bars are 2.5 mm at the oblique in the dashed circle. (FIG. 20C) Front and back of the extracted obliques. Scale bar 2.5 mm FIG. 20D) Fluorescent image of the obliques that shows the extent of the tissue formed by the injected spheroids.

(FIG. 21A) 1 HUVEC:1 MSC spheroids. (FIG. 21B) 1 HUVEC:3 MSC spheroids. (FIG. 21C) MSC spheroids.

(FIG. 24A) Dorsal skin was spread out and backside of window chamber was connected; Needles were used to create holes for window chamber; (FIG. 24B) A circle was marked on the skin to indicate the opening for the window chamber and the skin was carefully cut out; (FIG. 24C) Front and back of window chamber were assembled; (FIG. 24D) Nuts were used to lock the window chamber; A custom 3D printed backing was used to hold the skin in place; (FIG. 24E) Closed window chamber in place; Secured with lateral sutures; (FIG. 24F) A custom-made window chamber insert to test up to 9 conditions simultaneously was included.

FIG. 25A contains schematic diagrams (top) and corresponding experimental images (bottom) showing the steps of microtissue fabrication and in vivo perfusion. Experimental data were collected using GFP-labelled HUVECs and RFP-labelled mouse MSCs. First, a co-culture of endothelial cells (green) and therapeutic cells (red) is seeded on dissolvable alginate microwells. Second, after being cultured in maintenance medium without growth factors for 3 to 4 days, cells self-organize into microtissues with an endothelial core. A switch into culture medium with vasculogenic growth factors for an additional 4 days promoted formation of vessels within the microtissues. Third, alginate microwells were dissolved with 5% sodium citrate to release microtissues. Fourth, suspension of microtissues could be centrifuged and assembled into a macro-tissue in vitro to study vascular formation, or injected into the subdermis or ischemic hindlimb of a mouse to demonstrate engraftment in vivo. Fifth, injected microtissues rapidly connected to form perfused microvasculature in vivo. FIG. 25B shows the liquid handling steps in the process; 1) seeding the co-culture of ECs (green) and MSCs (red) by pipetting cells onto alginate microwell construct, 2) adding maintenance media once the cells have settled to the bottom of the microwells (approx. 30 minutes), 3) switching to vasculogenic media once an endothelial core has formed, and 4) gently dissolving the alginate microwells (approx. 5 minutes) to harvest microtissues (the microtissues can be gently washed prior to injection).

FIGS. 26A-26D illustrate scalability of method, showing massively parallel production of microtissues and formation of macrotissue. FIG. 26A contains pictures of three alginate microwells constructs for inserts into 24-well plates, 12-well plates or 60-mm dishes with the capacity to produce 24×1000, 12×3000 or 30,000 microtissues respectively. FIG. 26B illustrates of 250 million cells for seeding into alginate microwells. Cells in this figure are GFP-labelled HUVECs and RFP-labelled mouse MSCs. FIG. 26C shows a stitched brightfield image of cells seeded in a 60-mm construct with 30,000 wells to create 30,000 microtissues. Scale bar is 1 cm. FIG. 26D is a picture of a 1 mm thick macrotissues with an area of 1 cm$^2$ assembled in vitro by collecting the 30,000 mature pre-vascularized microtissues produced with the alginate microwell (a and b) construct in a 60-mm dish. Scale bar is 1 cm. FIG. 26E shows fluorescence images of the macrotissue in (d) with a close-up of the closely packed microtissues with endothelial cores (green). Scale bars are 1 mm (left) and 500 µm (right).

FIGS. 27A-27D illustrate self-organization of endothelial cores by timed exposure to growth factors. FIG. 27A is confocal fluorescence images of co-culture microtissues of GFP-labeled HUVECs (green) and RFP-labeled mouse MSCs (red) over the first three days in maintenance medium without growth factors (top) or in vasculogenic medium with 40 ng/mL VEGF and 40 ng/mL bFGF (bottom). The cells self-organize by migration, and either formed endothelial cores when cultured in media without growth factors (top) or had endothelial cells randomly distributed near the surface of the microtissue and did not form endothelial cores when cultured in media with growth factors (bottom). Scale bars are 100 µm. FIG. 27B is an overlay of fluorescent and transmitted images showing parallel production of microtissues in arrays of different sizes of microwells (with either 100, 200, or 400 µm diameter) and different co-culture ratios (1 EC:3 MSC, 1 EC:1 MSC or 3 EC:1 MSC). Different sizes of microwells yield different sizes of microtissues, either unvascularized with only MSCs or pre-vascularized with a co-culture of ECs and MSCs, and different co-culture ratios yield different endothelial core sizes. Scale bars are 100 µm. (FIG. 27C) Quantitative analysis of cell aggregation into microtissues and the formation of an endothelial core over time in 200 µm microwells, as measured by the radius of the smallest circle that can contain all MSCs (red) or all ECs (green) (n>20). FIG. 27D is a Barplot showing the size of fully-contracted microtissues (red) and the size of the endothelial cores (green) for all tested microwell sizes and co-culture ratios.

FIG. 28A shows maturation of endothelial cores with dynamic culture conditions for two co-culture ratios; 1 GFP-HUVEC:3 hAMSC (left) and 1 GFP-HUVEC:1 hAMSC (right). The cells are seeded (day 0) and initially cultured in maintenance medium without growth factors to form endothelial cores. After 3 days the microtissues were cultured in vasculogenic medium with 40 ng/mL VEGF and 40 ng/mL bFGF and the endothelial cores matured into vessels with discernable lumens (red arrows) and sprouts (white arrows). Scale bars are 200 µm. FIG. 28B shows epifluorescence, brightfield, and overlay images showing early self-organization of pre-vascularized microtissues over the first 20 hours, with a 1 GFP-HUVEC:1 hAMSC co-culture in 400 µm microwells. Scale bar is 200 µm. FIG. 28C shows epifluorescence, brightfield, and overlay images showing fusion of pre-vascularized microtissues (same conditions as in right FIGS. 28A and 28B) into mesotissues over the first 24 hours of the fusion process within a 400 µm collagen-doped alginate microwell. Scale bar is 200 µm.

FIGS. 29A-29E illustrate rapid in vivo vascularization upon injection of microtissues. FIG. 29A is a schematic diagram of experimental setup for observing vascular formation and integration with host vasculature in vivo in real time via a window chamber. Microtissues (from human cells formed under dynamic culture conditions in 200 µm microwells yielding microtissues 71±5 µm in diameter) were injected into a window chamber implant in a SCID mouse. FIG. 29B is real-time in vivo stereoscopic images of prevascularized microtissues with 1 GFP-HUVEC:1 hAMSC (top row) and unvascularized microtissues with hAMSC only (bottom row) through window chamber at different time points. Scale bars are 500 µm. In the top row, newly formed vessels are apparent within 4 days, and blood-filled vessels observed by day 7. In the bottom row, the dashed white line indicates the area of microtissues implant and no neo-vascularization was observed. FIG. 29C shows quantification of neo-vascularization of the prevascularized microtissues as the total length of vasculature within three ROI. The total length of vasculature increases substantially after day 7 for prevascularized microtissues. There is no substantial difference in total length of the vasculature for the unvascularized microtissues. FIG. 29D shows histograms of branching length in the newly formed microvasculature (b and c) at day 7, 9 and 11. Lines above histogram indicate the mean branch length and standard deviation for day 7, day 9, and day 11 as 93±39 µm, 86±29 µm, and 93±44 µm respectively. FIG. 29E shows real-time in vivo images of prevascularized microtissues with endothelial cells in green. Red arrow heads point to luminous, blood-filled vessels (as indicated by dark lines in fluorescence images and dark areas of brightfield images). Scale bar is 250 µm.

FIGS. 30A-30E illustrate rapid in vivo perfusion and muscle fiber regeneration upon injection of microtissues in ischemic hindlimb. FIG. 30A is a schematic diagram of the surgery used to induce ischemia in the right hind limb. The superficial femoral artery was isolated from the femoral vein and nerve bundle along the length of the thigh, ligated and totally excised. The mouse then received four injections along the length of the thigh of either 25 µL PBS (control) or microtissues (corresponding to 0.5×10$^6$ cells) injected at each site. The microtissues were formed in 200 µm microwells with maintenance media and a 1 mEC:1 mMSC co-culture ratio yielding prevascularized microtissues 71±5 µm in diameter with endothelial cores. FIG. 30B is representative images of blood perfusion in the hind limbs measured with laser speckle contrast imaging (LSCI) for the two experimental groups. The perfusion of each limb was measured as the average LSCI intensity of the planar surface of the paw (dashed white outline). FIG. 30C shows quantification of perfusion in the hindlimbs as the perfusion ratio (R/L) between the naïve left (L) hindlimb and the ischemic right (R) hindlimb (n=3 mice for each condition) with the control mice in blue and the microtissue treatment mice in green. The best-fit (dashed) and 95% confidence interval (dotted) lines are shown (from day 0 to 9 for microtissues, from day 0 to 14 for control). FIG. 30D shows histology of the gastrocnemius muscle on day 14 with an H&E stain. White arrows indicate centralized nuclei of regenerating muscle fibers. Scale bar is 50 µm. FIG. 30E shows the percentage of myofibers characterized as necrotic because of hyalination (pink) or as regenerating, viable myofibers assessed by centralized nuclei (purple) (n=3). (4 ROIs of 587×440 µm$^2$ for each condition). Error bars are standard deviations, * indicate significantly more regenerating fibers with p<0.05.

FIG. 31A shows six cross-linked alginate microwell constructs in the PDMS mold with the top three constructs removed. FIGS. 31B-31D show how the alginate molds are carefully loosened with a pair of sterile tweezers and removed from the mold holding on only to the "wings" to preserve the microwell structures in the middle. FIG. 31E shows the alginate constructs flipped to expose the microwells before being placed in the well plate (FIG. 31F).

FIG. 32A is an image of microtissue and endothelial core formation of 1 EC:1 DFC in 400 μm wells after three days culture in maintenance medium. FIG. 32B is a barplot of the radius of the smallest circle that can contain all ECs (green) or all DFCs (dark gray) for the different well sizes at Day 3. FIG. 32C is a barplot of the number of microtissues formed per mm2 (dark grey) and the number of those microtissues that contain endothelial cores (light grey).

FIG. 36A represents 1 HUVEC:1 hAMSC microtissues. FIG. 36B represents 1 HUVEC:3 hAMSC microtissues. FIG. 36C represents hAMSC only microtissues.

FIGS. 38A-38F illustrate window chamber surgery. In FIG. 38A dorsal skin was spread out and backside of window chamber was connected, and needles were used to create holes for window chamber. FIG. 38B shows a circle marked on the skin to indicate the opening for the window chamber and the skin was carefully cut out. In FIG. 38C the front and back of window chamber were assembled. In FIG. 38D nuts were used to lock the window chamber, with a custom 3D printed backing used to hold the skin in place. FIG. 38E shows a closed window chamber in place, secured with lateral sutures. FIG. 38F shows a custom-made window chamber insert to test up to 9 conditions simultaneously.

FIGS. 40A-40D illustrate a procedure for injecting microtissues in vivo (without window chamber). FIG. 40A illustrates injecting a solution with microtissues (1EC:3MSC and 200 μm size) into the adipose tissue of the obliques. A small incision along the back was made to ensure the correct position of the injection site. FIG. 40B shows the mice were sacrificed and the entire obliques (white dashed circle) were excised after 18 days of implantation. FIG. 40C shows front and back of the extracted obliques. Scale bar is 2.5 mm FIG. 40D illustrates merged and individual images of brightfield and fluorescent images showing the position of the injected microtissues. Top: RFP-MSC only microtissues. Bottom: 1 GFP-ECs:3 RFP-MSC ratio microtissues.

FIG. 41A shows a skin incision made over the femoral artery for a high femoral artery ligation and total excision as previously described. FIG. 41B shows fascia cleared and the femoral artery identified (picture taken through microscope). FIG. 41C shows the femoral artery was isolated from the femoral vein and nerve bundle (picture taken through microscope).

FIG. 42 tabulates advantages for different cell aggregation production methods.

DETAILED DESCRIPTION

Figure 1:
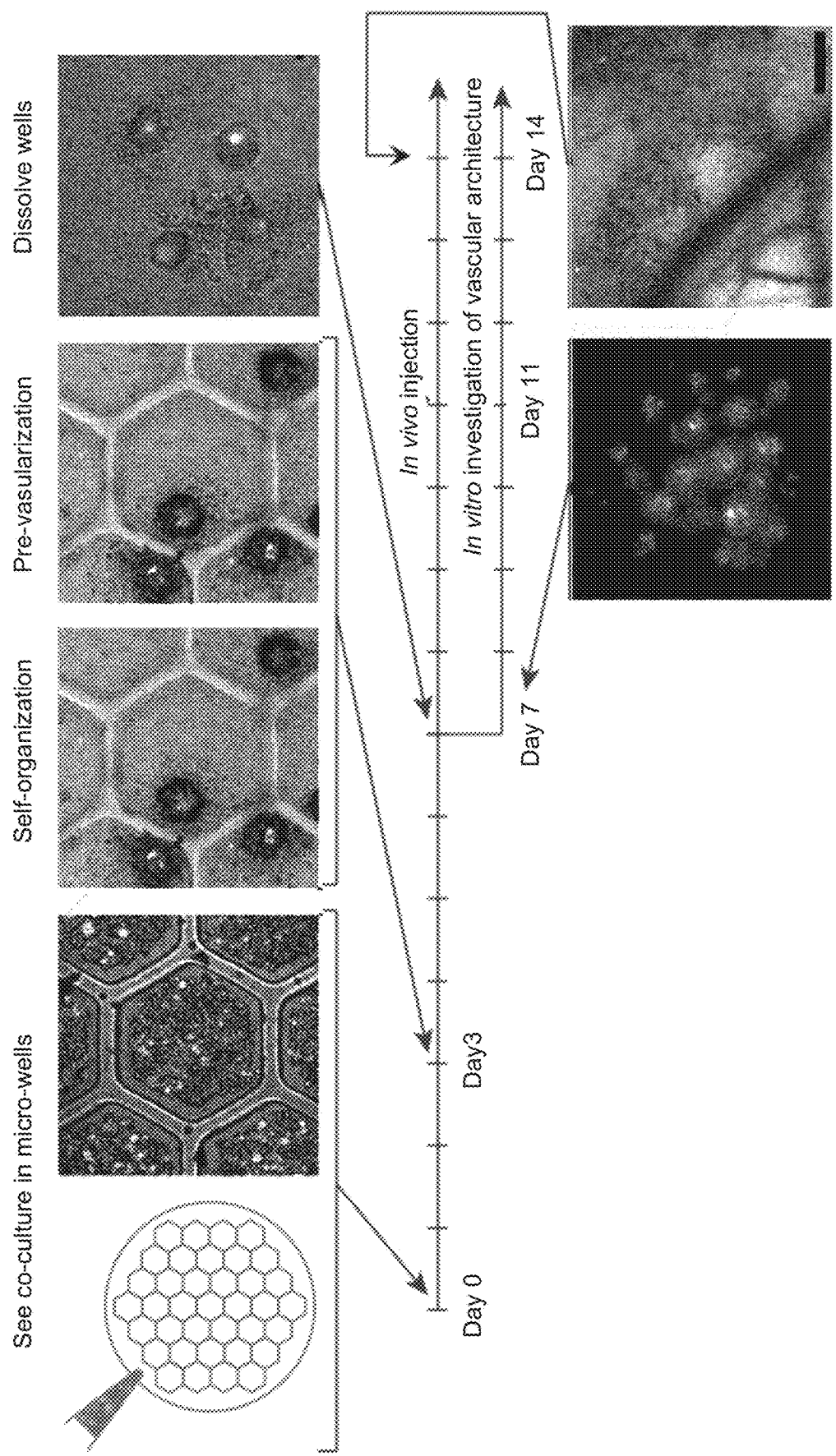
FIG. 1 is a timeline diagram illustrating aspects and associated images of spheroid fabrication and delivery, according to one or more embodiments of the disclosed subject matter.

The disclosed embodiments include methods for producing microtissues with blood-vessel building blocks for rapid vascularization and cell survival upon in vivo implantation. Co-cultures of cells within spheroids may enable cells to self-organize into a bulk tissue. Spheroids may be scaffold-free and may not require post-formation tissue maturation or a potentially toxic cell deposition process In embodiments of the disclosed subject matter, spheroid micro-tissues can provide native-like microenvironments for cells to be delivered in vivo. In particular, a high-throughput protocol for manufacturing injectable spheroids is disclosed herein, whereby the resulting micro-tissues may be used to deliver a treatment or therapy to a patient (e.g., human or animal), for example, by providing a mesenchymal stem cell (MSC) therapy.

In one or more embodiments, each spheroid micro-tissue produced using the disclosed methods has a primitive vasculature. Upon injection into the patient, the primitive vasculature in each micro-tissue can connect with existing vasculature and/or with the primitive vasculature of other injected micro-tissues to form a complete, perfused vasculature, for example, in as little as four days. Micro-tissues-containing blood vessel units may be engineered with directed cell self-organization using timed exposures to growth factors and injected as treatment of critical limb ischemia, for example.

In one or more embodiments, a clinically significant number (e.g., on the order of millions) of spheroids may be grown. Each spheroid can have multiple cell types. The structure of spheroids may be engineered to form microtissues by directing self-organization of the different cell types using particular patterns of timing for exposure to, and privation from, growth factors. For example, methods may be used to engineer micro-tissues spheroids of mesenchymal stem cells, smooth muscle cells, dermal fibro-blast and adipose cells, each of which contain a unit of blood vessel. Based on the current disclosure, one of ordinary skill in the art may appreciate that different cells and combination of cells are also possible, as well as different growth factors. Accordingly, embodiments of the disclosed subject matter are not limited to the particular cell types, combination of cells, and/or growth factors specifically described herein.

In one embodiment microtissues with blood-vessel building blocks are produced at high-throughput in vitro. This embodiment uses dissolvable alginate as a sacrificial material for microwells to generate microtissue reproducibly in a manner suited for mass production. This approach offers high-throughput production with control over microtissue size and composition, the microtissues can be continuously observed, easily harvested, and are suitable for use in vivo. Furthermore, they can be delivered with injections obviating invasive surgery to ischemic sites with impaired wound healing. This approach was validated by observing the self-organization of thousands of microtissues in vitro and in vivo, including rapid integration with the host's vascular network and re-perfusion of an ischemic hindlimb.

Figure 2:
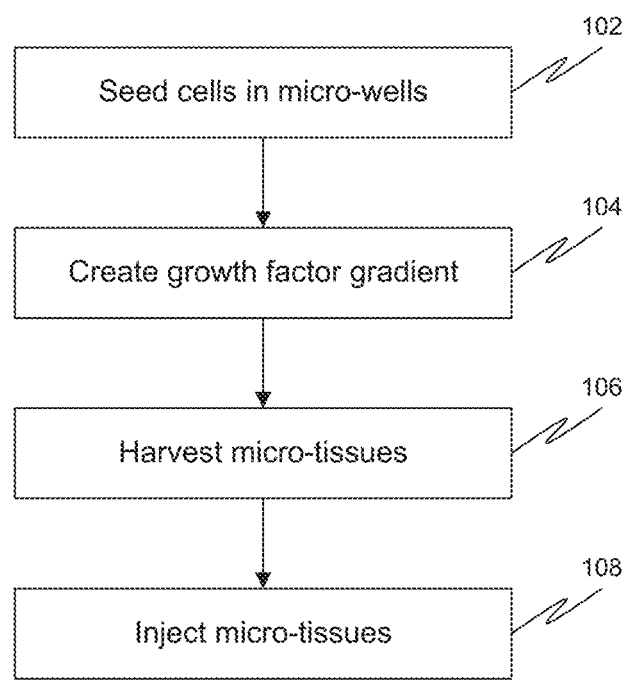
FIG. 2 is a process flow diagram of a method for spheroid fabrication and delivery, according to one or more embodiments of the disclosed subject matter.

Referring to FIGS. 1-2, an embodiment for forming injectable microtissues is illustrated. At 102, a co-culture of therapeutic cells and endothelial cells may be seeded over a construct with a multitude of microwells (for example, as illustrated in FIG. 1). The construct, or at least surfaces of the microwell in contact with the cell, may be formed of a material that is substantially non-adhesive to the cells within the microwell. For example, the construct may be formed of alginate, agarose, and/or polydimethylsiloxane (PDMS), among other materials. The cells may be seeded on the construct and then be provided with a predefined time to settle into the microwells, with approximately the same number of cells in each well. Cells may tend to adhere to adjacent structures. The present microwell is non-adhesive such that the cells only to adhere to each other. Within an initial culture period (e.g., over first 24 hours), the cells in each microwell adhere to each other and contract to form spheroids. The distribution of the cells within the spheroid is random, reflecting the random distribution originating when they were initially seeded into the microwells.

At 104, the self-organization of the different cell types in the spheroid co-cultures may be directed by timed exposure to growth factors. For example, when employing endothelial cells to form blood vessel, the endothelial cells respond to vascular endothelial growth factor (VEGF) and basic fibroblast growth factor (bFGF) with increased proliferation and migration. If a gradient of these growth factors is present, the endothelial cells will respond with a directed migration towards the higher concentration. Most cell-types will express either one or both of these growth factors in response to hypoxia (less than optimal oxygen). These responses may be used to direct the endothelial cells self-organization into blood vessel units at the center of the spheroids.

After seeding the cells in non-adherent micro-wells, cell culture media were provided without VEGF or bFGF. After an initial culture period (e.g., on the order of a day), the cells were organized into a spheroid, with the cells in the middle of each spheroid beginning to express VEGF and bFGF, thereby creating a gradient from the center of the spheroid to the exterior thereof. After an intermediate culture period (e.g., at 3-4 days), the endothelial cells were observed to have migrated into the middle of the spheroid forming an endothelial core, i.e., a blood vessel unit. Growth factor was then be introduced to allow the spheroids to further mature.

For example, the cells may be cultured in the microwells without vasculogenic growth factors for 3 days (i.e., to allow formation of the endothelial core), followed by an additional 7 days of culture with vasculogenic growth factors. The cells self-organized into spheroids with an endothelial core that matured into vessels. Referring to FIG. 3, images illustrating features of the endothelial cores formed by directed self-organization of cells through timed exposure to growth factors are shown. As illustrated in FIG. 3A, the first three days of culture in media without growth factors (VEGF and bFGF) induces the endothelial cells to migrate to the spheroid centers and to form endothelial cores. In contrast, FIG. 3B illustrates endothelial cells in spheroids grown in media with growth factors for the first three days. In FIG. 3B, the endothelial cells migrated to the periphery of the spheroid instead of the center. After endothelial core formation, spheroids continuously cultured in media without growth factors remain as endothelial cores, as illustrated in FIG. 3C. However, endothelial cores induced to mature and produce lumen and/or sprouts if growth factors were added to the media after the endothelial cores had formed, as illustrated in FIG. 3D.

Thus, micro-tissues with primitive vasculature may be formed and harvested from the construct with microwells at 106 for subsequent injection at 108. For example, the microwells (e.g., formed of alginate) may be dissolved to release the spheroids into suspension as has been confirmed by experiment. Such a suspension of spheroids may be assembled into a tissue in vitro to study the vascular formation or injected into a patient to effect a treatment. For example, in mouse studies described further below, hundreds of such micro-tissues, each containing a blood vessel unit, were injected into a window chamber. Upon injection, the blood vessel units connect and form a new vascular network with the endothelial core as nodes. The new vascular network connects to the mouse's own vasculature after about seven days and is perfused. In one or more embodiments, timed, consecutive seedings may be used to further direct self-organization.

Figure 4:
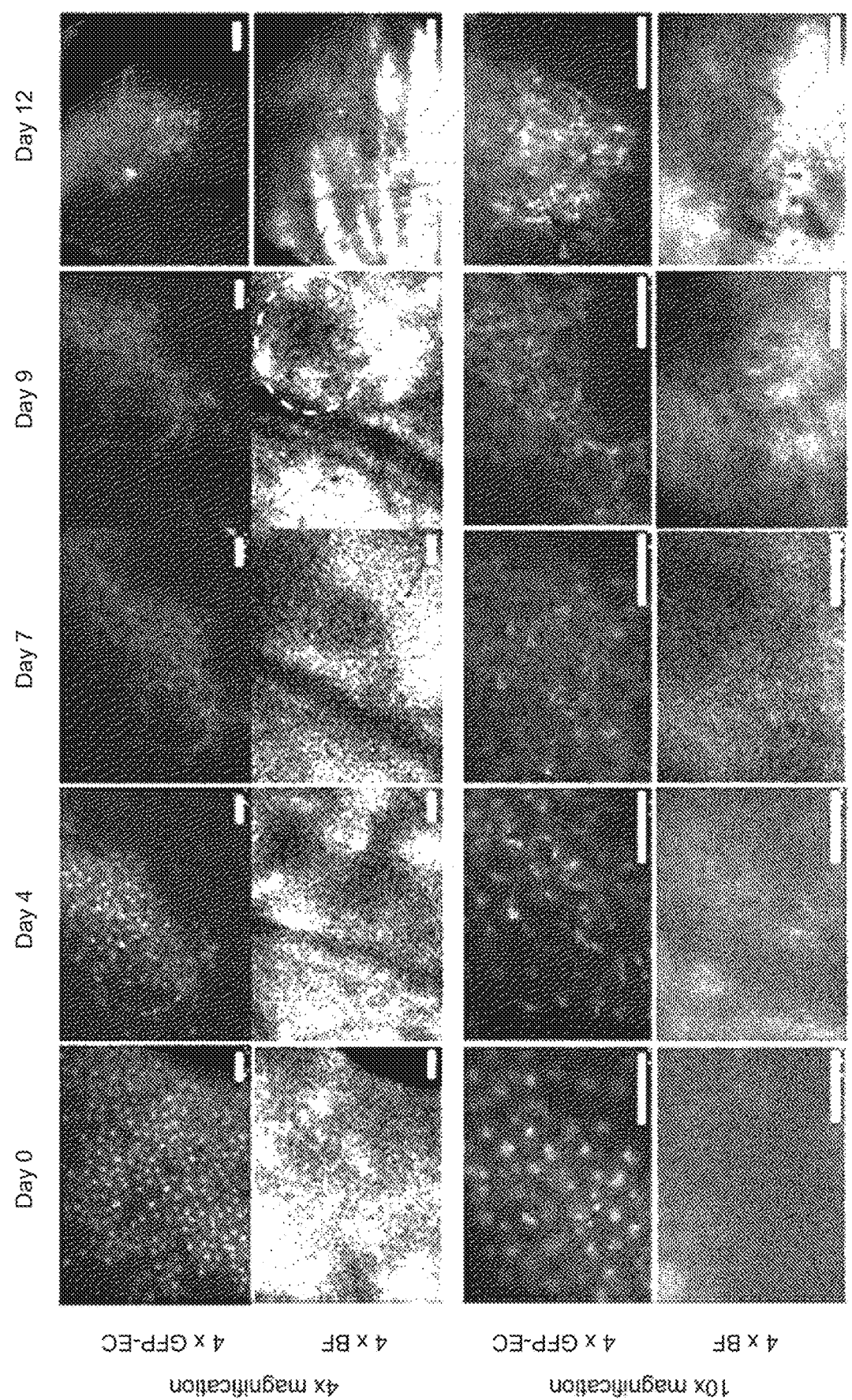
FIG. 4 are images (bottom two rows at higher magnification) illustrating the kinetics of vascular formation for spheroids at different time points in vivo, according to one or more embodiments of the disclosed subject matter.

Referring to FIGS. 3A, 3B, 3C, various images illustrating vascular formation by injected spheroids in vivo are shown. FIG. 4 shows images of spheroids at different time points in vivo. The spheroids were grown in microwells having 200 μm using Human Umbilical Vein Endothelial Cells (HUVEC) with Green Fluorescent Protein (GFP) in a ratio of 1:1 with MSCs. The cells were cultured in the microwell for three days using a maintenance medium (i.e., without growth factors) followed by six days in a vasculogenic medium. In FIG. 4, arrow blood-filled vessels can be observed. The scale bars represent 250 μm.

Figure 5:
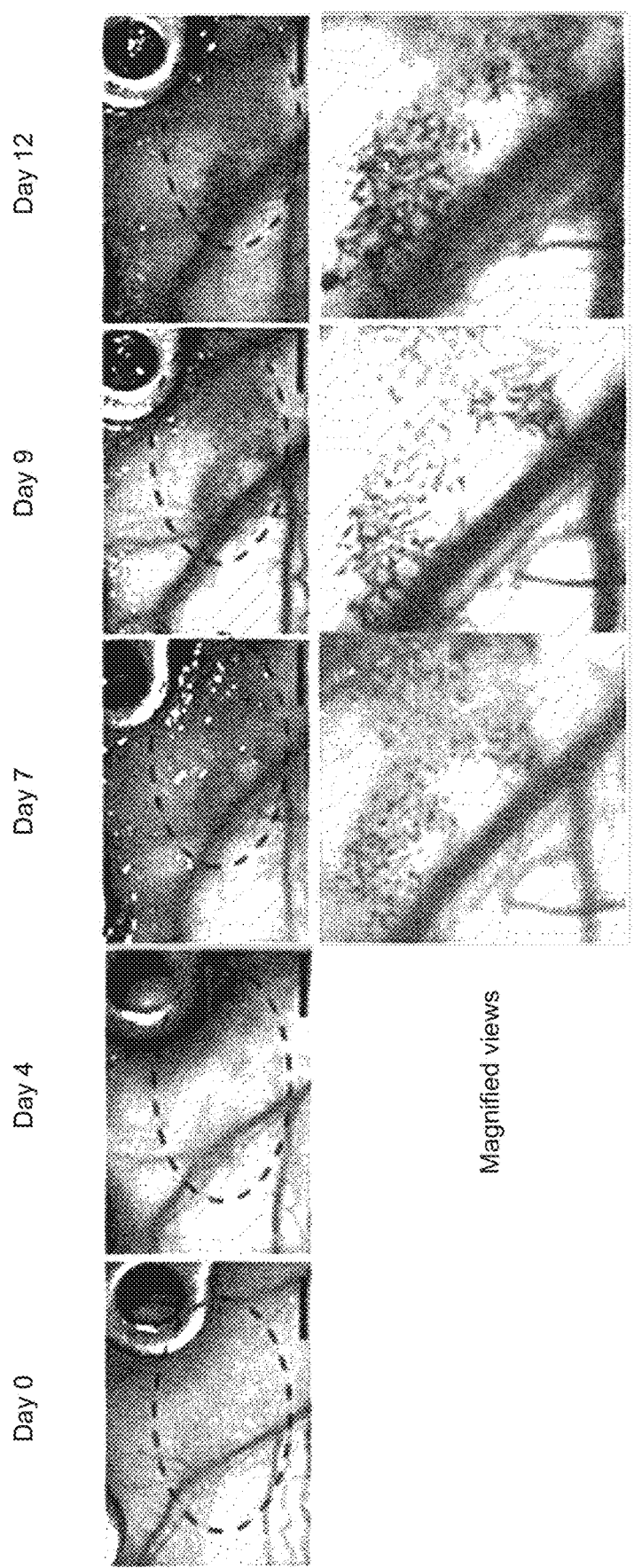
FIG. 5 are stereoscopic images (bottom row at higher magnification) illustrating the progression of injected spheroids into blood vessels in vivo, according to one or more embodiments of the disclosed subject matter.
Figure 6:
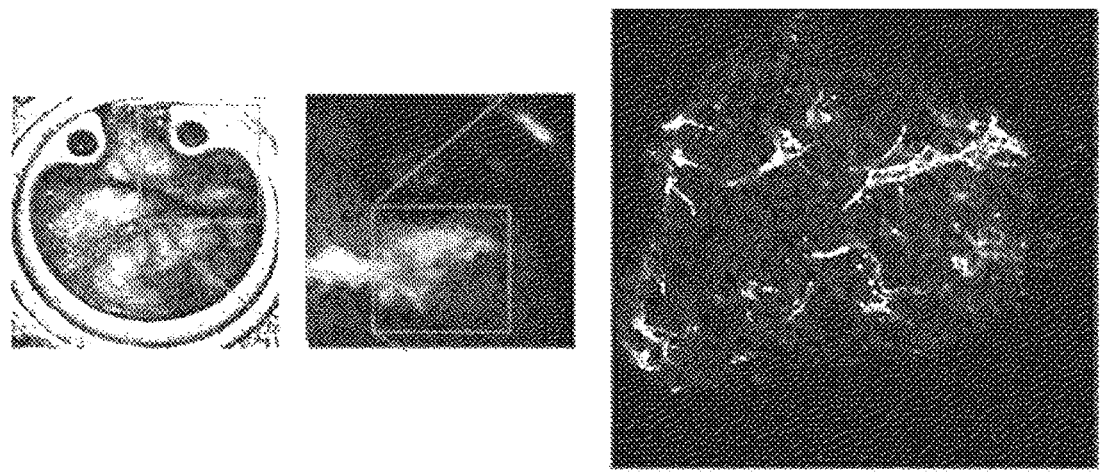
FIG. 6 shows images illustrating a newly formed blood vessel in vivo, according to one more embodiments of the disclosed subject matter.

FIG. 5 shows stereoscopic images of injected microtissues at different time points in vivo. As may be confirmed from the figures and as observed in the laboratory, newly formed vessels resulting from the injection are blood-filled and functional. The newly formed blood vessels were first observed at day 7 in FIG. 5, and close-ups of the blood vessels are shown in the bottom row. In FIG. 5, the scale bar in the top row of images represents 1.25 mm and the scale bar in the bottom row of images represents 0.5 mm. The dotted oval in FIG. 5 encircles the implant region. FIG. 6 shows images of the GFP signal from the newly-formed blood-filled vessels at Day 7.

The resulting vasculature of the micro-tissues both in vitro and in vivo may be controlled. For example, the size of the spheroids may be adjusted by varying the number of cells seeded into a microwell that eventually organize into a single spheroid and/or by adjusting the size of the microwell. The size of the microwells and the concentration of cells adjusted to determine the amount of cells that will settle in each of the wells. For example, the microwells can each have a diameter less than 500 µm, for example, between 10 µm and 500 µm, such as 100 µm, 200 µm, and 400 µm. Other microwell diameters are also possible according to one or more contemplated embodiments. Moreover, although diameter has been used herein to refer to the size of the microwells, it is contemplated that the microwell may have a shape other than circular, for example, hexagonal as illustrated in FIG. 1, elliptical, rectangular, or other shapes may be employed. Varying the size of spheroids before allowing them to aggregate into tissues can provide control of the resulting vasculature. The disclosed methods are highly scalable. For example, the methods may be used to produce up to half-a-billion cells, which would be enough to form a 10 mm×10 mm×1 mm tissue in vitro.

According to embodiments of the disclosed subject matter, treatments for various vascular issues are be provided. In embodiments, the disclosed methods for making spheroids are followed by injection or implantation to provide a treatment for critical limb ischemia (CLI). Suitable therapeutic cells may be selected for this purpose. A patient may be injected on an outpatient basis with the disclosed engineered microtissues, each of which contains a blood vessel unit (i.e., a spheroid with an endothelial core). Upon injection, these microtissue units are observed to connect to form a vascular network, which formation occurs faster than the formation of a vascular network by single cell therapies. Multiple injections may be given along the affected limb resulting in a new vascular network that can perfuse the limb and save it from amputation. The therapy may be autologous by using blood vessel units formed from the patient's own cells, for example, harvested with liposuction and injected in-clinic by a clinician.

Other therapeutic technologies include, but are not limited to, stem cell injections, endothelial progenitor cell injections, endothelial cell injections and growth factor injections. In addition, lymphatic endothelial cells may be used instead of vascular endothelial cells. Thus, a lymph vessel unit may be formed instead of a blood vessel unit. Injection of the lymph vessel units can create a lymphatic network that may relieve lymphedema.

Moreover, embodiments of the disclosed subject matter may be extended to other cell types to form injectable micro-tissues of different organ tissues, thereby providing an alternative to whole organ transplants.

In another example, embodiments of the disclosed spheroids may be used to treat subcutaneous adipose tissue loss. Subcutaneous adipose tissue loss is associated with numerous conditions including oncologic resection, congenital birth defects and traumatic injury. The current clinical treatment strategies for adipose tissue reconstruction primarily involve the transplantation of autologous composite tissue flaps or synthetic substitutes. However, the use of autologous tissues is associated with the creation of a donor site defect and potentially, the need for costly and complex surgical procedures. Synthetic implants are associated with immune rejection, implant migration and resorption, and a failure to integrate into the host tissues. Scaffolds for tissue engineering may be differentiated according to whether they are implantable or injectable. Injectable scaffolds may minimize risk of infections and scarring as well as the ability to fill irregularly shaped defect sites, making them particularly applicable for adipose tissue engineering.

Mesenchymal stem cells (MSCs) are commonly characterized by expression of fibroblastic markers and by their in vitro differentiation potential into, at a minimum, adipocytes, chondrocytes and osteoblasts. Moreover, MSCs display the general features of primary and non-oncogenic (i.e., non-transformed) cell type: serum dependency, limited growth rate and limited life span during in vitro culture. Moreover, other in vivo beneficial effects of MSCs are related to secretion of trophic factors. For example, C-MSCs present antigenic potential, including, but not limited to, expression of vascular endothelial growth factor (VEGF)), insulin like growth factor (IGF), platelet derived growth factor (PDGF), hepatocyte growth factor (HGF), basic fibroblast growth factor (bFGF), transforming growth factor β1 (TGFβ1), angiopoetin-1 (Ang-1), and stem cell factor (SCF).

Figure 7:
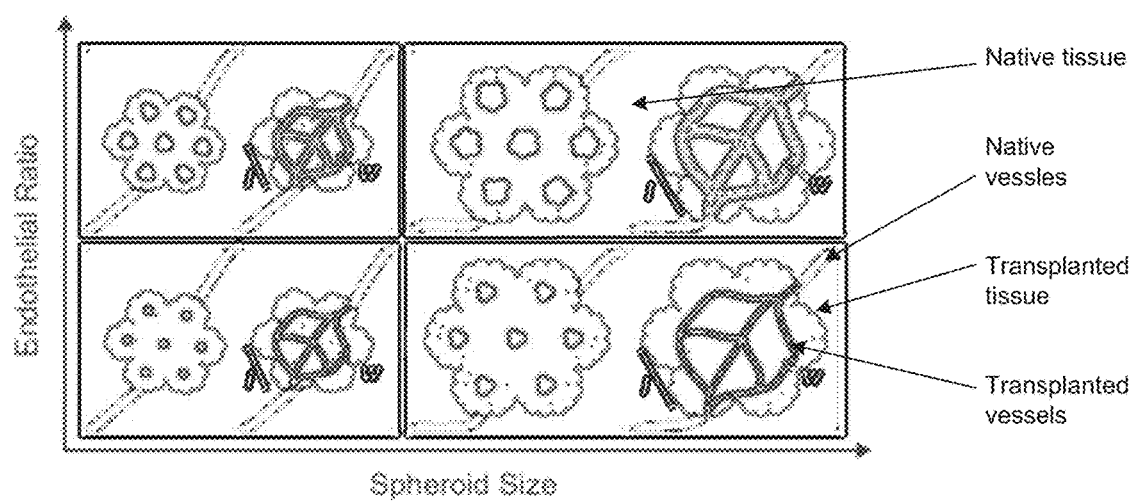
FIG. 7 is a graph illustrating the relationship between cell ratios, spheroid size, and various features of the resulting network architecture, according to one or more embodiments of the disclosed subject matter.

In one or more embodiments, controlling the architecture of the vascular network may be influenced by various factors. By packing larger spheroids a larger distance between the endothelial cores may be achieved versus packing smaller spheroids. The endothelial cores can act as nodes in the vascular network, so that the larger distance between the endothelial cores in larger spheroids can result in longer branches in the resulting fully-formed vascular network. Secondly, micro-vessels may be formed by a single, or several, endothelial cells. Micro-vessel walls are one cell thick, so micro-vessels made of more cells will have larger diameters and/or be wider. All, or a proportion, of the available endothelial cells provided by the spheroids can participate in the forming of the vascular network. Accordingly, the higher ratio of endothelial cells to mesenchymal stem cells may yield wider vessels. FIG. 7 is a schematic illustrating the above described relationships depending on spheroid size and cell ratio.

An array of different spheroid sizes and cell ratios were tested to demonstrate that ratio of cells in, and size of, the spheroid can determine the architecture of the resulting blood vessel network. In particular, three different microwell sizes, which determine the ultimate size of the spheroid, were tested: 100 µm, 200 µm, and 400 µm. In addition, three different cell ratios were tested: 3 endothelial cells to 1 mesenchymal stem cell (3:1), 1 endothelial cell to 1 mesenchymal stem cell (1:1), and 1 endothelial cell to 3 mesenchymal stem cells (1:3).

Figure 8:
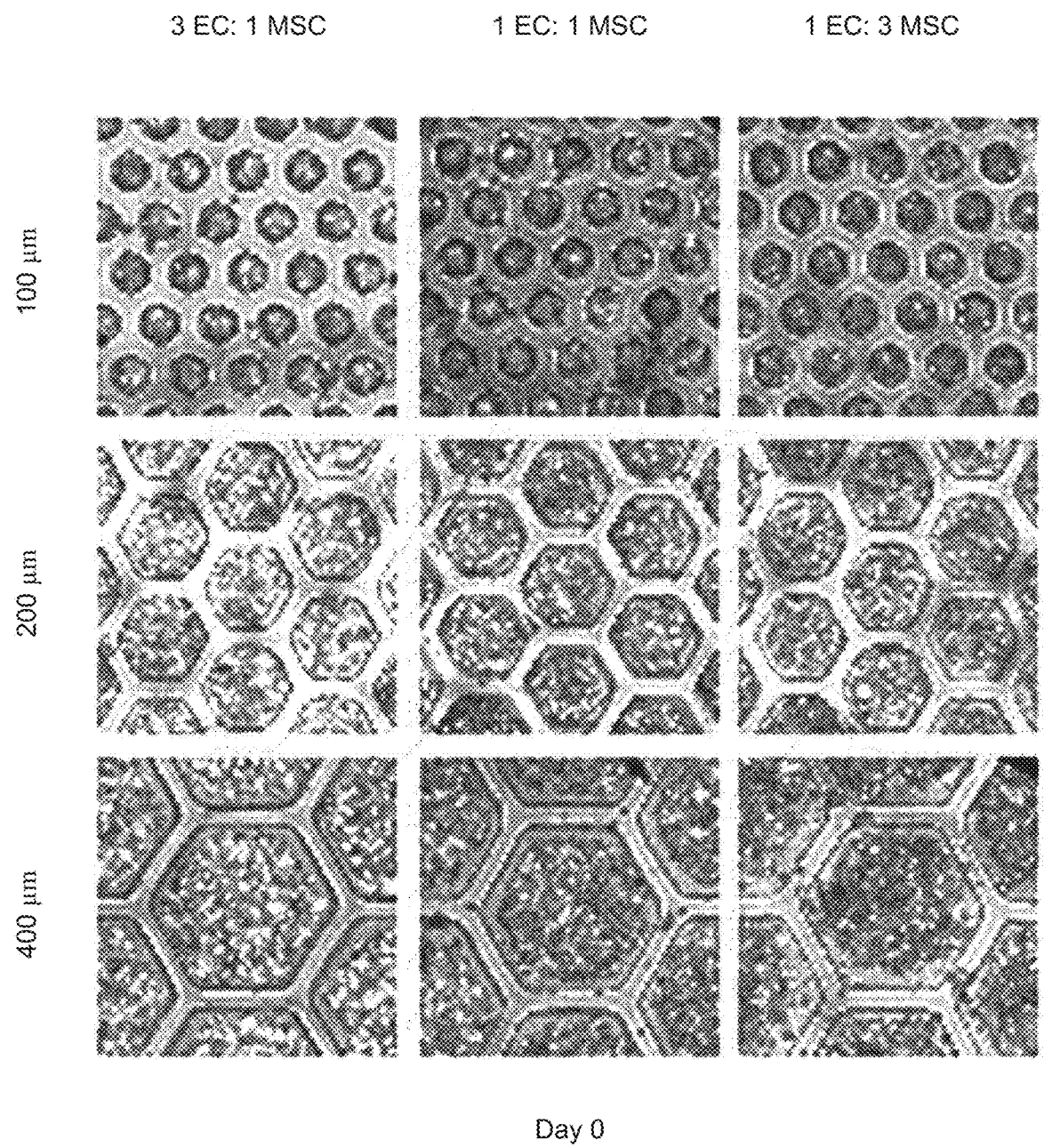
FIG. 8 are images of microwells seeded with different conditions including microwell size and ratio of endothelial cell to mesenchymal stem cell ratio immediately after seeding, according to one or more embodiments of the disclosed subject matter.
Figure 9:
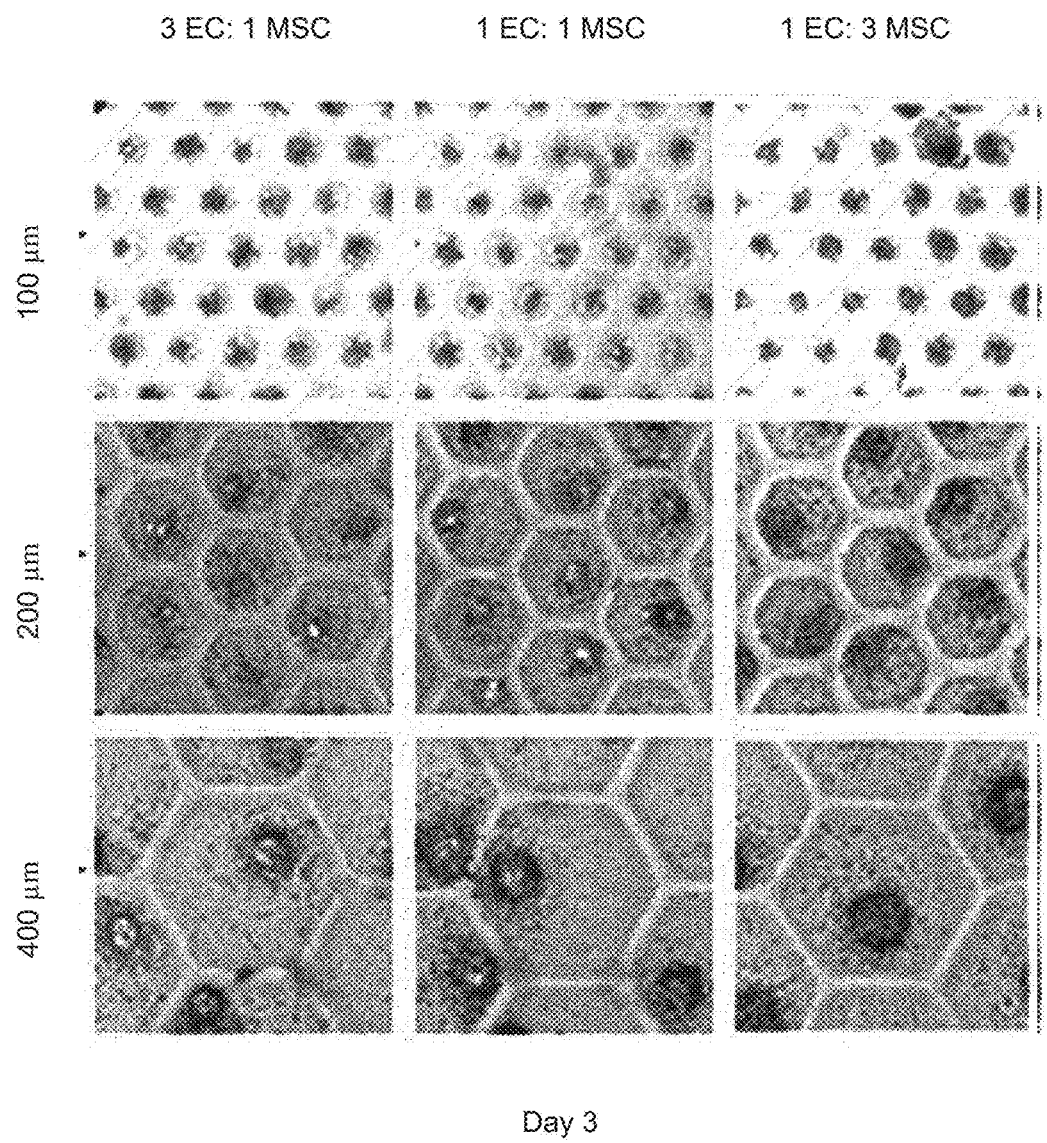
FIG. 9 are images of microwells seeded with different conditions including microwell size and ratio of endothelial cell to mesenchymal stem cell ratio at 3 days of culture without VEGF, according to one or more embodiments of the disclosed subject matter.
Figure 10:
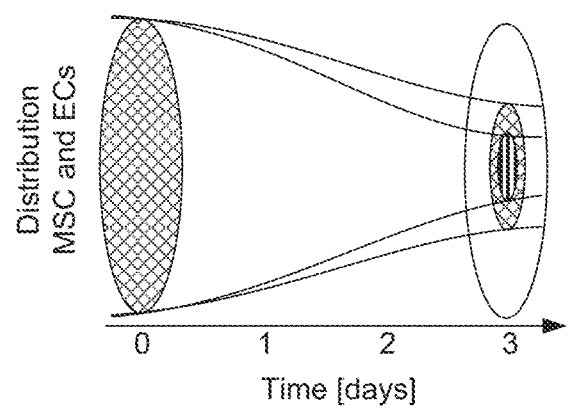
FIG. 10 is a simplified graph illustrating the size of spheroids and radial distribution of endothelial cells and mesenchymal stem cells over time, according to one or more embodiments of the disclosed subject matter.

FIGS. 8-9 show the formation of these pre-vascularized spheroids as a three-by-three array for the time period immediately after seeding at day 0 (FIG. 8) and after initial spheroid formation in basal media with distinct endothelial cores at day 3 (FIG. 9). FIG. 10 illustrates the size of the spheroids and radial distribution of endothelial cells and mesenchymal stem cells over time.

The first time point, illustrated by FIG. 8, is at day 0 right after seeding the co-culture of endothelial and mesenchymal stem cells into the microwells. The second time point, illustrated by FIG. 9, is at day 3 after the cells have been cultured in the microwells allowing them to form spheroids. The first three days, the cells/spheroids are cultured in a basal media without any exogenous growth factors thereby observed to cause the endothelial cells to self-organize and migrate to the center of the spheroid creating an endothelial core within each spheroid. While not wishing to be bound by any particular theory, cells at the center of the spheroid exude endogenous growth factors that guide the endothelial cells on the periphery of the spheroid toward the center. As a result, so the cells in the microwell self-organize to form a spheroid with an endothelial core and a mesenchymal stem cell shell whose thickness may be varied, for example by adjusting the proportion of the MSC and EC. After day 3, when the endothelial cores have formed, the spheroids were further cultured in vascularization media with exogenous growth factors, which was observed to cause the cells in the endothelial core to sprout toward the surface and mature into lumenous vessels.

Producing the spheroids in non-adhesive microwells, rather than in, for example hanging drops, allows for large numbers of spheroids to be made in relatively small space with very little labor. The disclosed spheroid fabrication procedure yields copious amount of spheroids, all with endothelial cores prompted by culture without exogenous growth factor and with reproducible sizes. FIG. 10 shows the size of the spheroids over time, as well as the intra-spheroid organization of the endothelial cells and mesenchymal stem cells. There is very little variance in the size of the cells, and the core's position is centered in all the spheroids.

Figure 11:
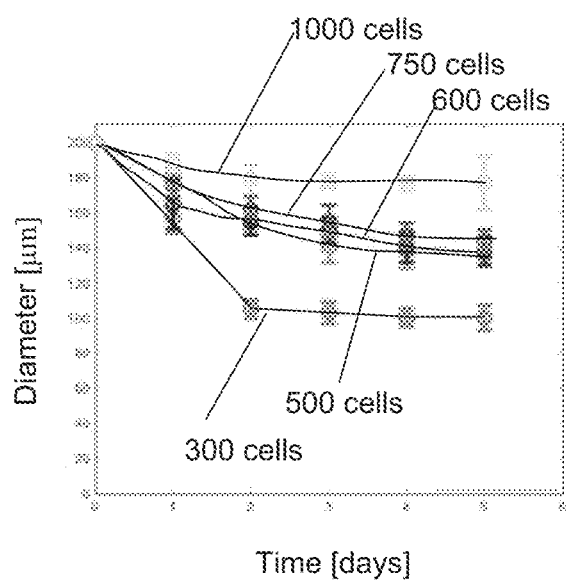
FIG. 11 is a graph of spheroid diameter over time for spheroids fabricated according to one or more embodiments of the disclosed subject matter.
Figure 12:
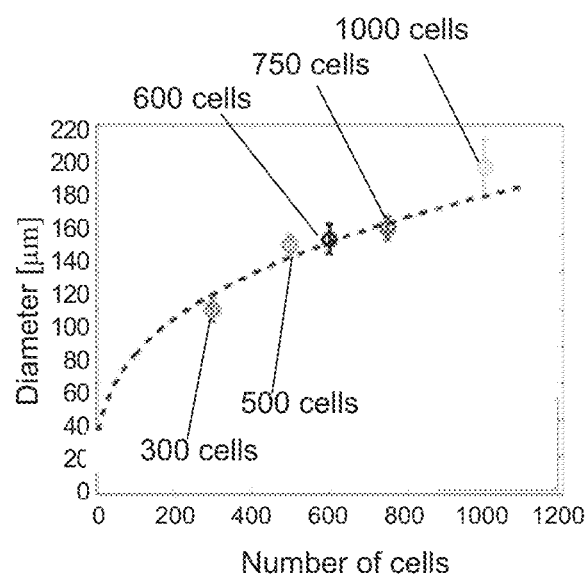
FIG. 12 is a graph of spheroid diameter as a function of the number of cells in spheroids fabricated according to one or more embodiments of the disclosed subject matter.

The diameter of each spheroid is related to the number of cells allocated to each spheroid (i.e., the cells settling in each microwell), as illustrated in FIGS. 11-12. The size of the spheroid may thus be controlled by seeding the same number of cells into fewer and larger wells, or by seeding more cells into the same diameter wells (in which case, the depth of the well may be increased in order to hold the added number of cells).

In addition to the advantages noted above, the use of a non-adhesive material such as alginate for the microwell can have other advantages as well. For example, the alginate polymers may be de-crosslinked so as to dissolve the microwells after the spheroids are fully formed and/or pre-vascularized. Dissolving the alginate microwells leaves the spheroids floating in a solution, which may be gently pipetted into tubes, spun down and resuspended in whichever media is desirable for cell delivery. The dissolvable alginate provides a gentle but effective way of harvesting the spheroids for future therapeutic use.

The construct can have a large number of microwells, for example, at least 1000 microwells. For example, the construct may be molded using alginate. A master mold for the alginate microwell construct may be fabricated using SU-8 patterned on 3-inch silicon wafers by photolithography. A polydimethylsiloxane (PDMS) replica may be formed from the master mold and made hydrophilic by plasma treatment. The PMDS replica may be submerged in distilled water to retain their hydrophilicity. The PMDS replica can then be autoclaved and cooled prior to casting.

Cold collagen solutions may be mixed with cold 1.6% w/v alginate in a 1:1 ratio. The resulting collagen-alginate solution may be placed on ice before pipetting the solution into the PDMS mold. Thus, the hydrogels contained a constant amount of alginate (0.8% w/v), which may be selected to be a minimum amount to support molding and handling of microfluidic hydrogels at low collagen density. The top of the molds may be closed with cellulose dialysis membranes (6000 kD MWCO). The membranes may be flattened, for example, by using the edge of a sterile glass slide. The collagen component may be allowed to gel for 50 min at either room temperature or 37° C. before pipetting a 60 mM $CaCl_2$ HEPES buffer solution on top of the membrane for at least 45 min to crosslink the alginate at room temperature. The hydrogels may be removed from the molds and placed in HEPES saline buffer solution supplemented with 1.8 mM $CaCl_2$ to prevent leaching of the calcium ions from the hydrogels.

The GFP-labelled human umbilical vein endothelial cells (GFP-hUVECs) may be cultured in Endothelial Growth Medium 2 at 37° C. and 5% $CO_2$. The hUVECs may be passaged gently using TrypLE and used only until passage P6. The RFP-labelled mouse mesenchymal stem cells (RFP-mMSCs) may be cultured in DMEM with 10% FBS and 1% PenStrep at 37° C. and 5% $CO_2$. The mMSCs can also be passaged gently using TrypLE and used only until passage P8.

To culture the spheroids, the 1.8 mM $CaCl_2$ solution that the alginate microwells were stored in may be removed and replaced with enough DMEM media to cover the constructs. The microwell constructs can then be placed in the incubator at 37° C. and 5% $CO_2$ to equilibrate for 20 minutes. Then the media may be removed and the microwell constructs gently dried using surgical spears. The spheroids can then be seeded in the microwells using a positive displacement pipette with 20 μL of the desired cell suspensions. The cells can then be cultured in 0.5 mL of DMEM with 10% fetal bovine serum (FBS), 1% PenStrep and 20 ng/mL ascorbic acid for 3 days with a media change on the second day.

To assemble the spheroids in vitro, the media may be removed from the microwells, which may subsequently be de-crosslinked with 200 μL of 5% sodium-citrate, thereby releasing the fully-formed spheroids into suspension. The suspension may be gently spun down at 220 g for 5 minutes. The supernatant may be removed and the spheroids resuspended in 0.5 mL vascularization media (DMEM) with 10% fetal bovine serum (FBS), 1% PenStrep, 20 ng/mL ascorbic acid, 20 ng/mL vascular endothelial growth factor (VEGF) and 20 ng/mL basic fibroblast growth factor (bFGF). The spheroids can then be spun down again at 220 g for 10 minutes and left in the incubator for an hour to form primary cell-cell adhesions between the spheroids, thereby forming macroscopic aggregates.

To inject spheroids in vivo, the media may be removed from the microwells, which can subsequently be de-crosslinked with 200 μL of 5% sodium-citrate, thereby releasing the fully-formed spheroids into suspension. The suspension may be gently spun down at 220 g for 5 minutes. The supernatant may be removed and the spheroids resuspended in 200 μL PBS. The resulting solution may be injected into a patient under sterile conditions, e.g., on to a mouse's open window chamber.

The above method was employed and confirmed in laboratory experiments but the disclosed subject matter is not limited to the specific method described.

Embodiments of the disclosed subject matter may provide for or include one or more of the following features or advantages:
  Improve cell survival after delivery—by delivering the building blocks of a vascular network together with the therapeutic cells, the perfusion and/or vascularization and/or integration with the existing vascular network of the patient may be enabled.
  Mature tissues—endothelial cells in the injectable microtissues have been induced to form mature vessels with appropriate timing of growth factors.
  Improved vascularization—pre-vascularization of the microtissue allows delivery of blood vessels rather than single cells which may or may not assemble into a blood vessel.
  Scaffold-free—structures may be formed without using a scaffold.
  Injectable—microtissues may be created and controlled ex vivo.
  Ease of manufacturing—disclosed method is high throughput and less labor intensive than existing methods, and may be automated.

Self-organization using growth factors—for complex tissue/organ engineering, relying on the cells' ability to self-organize may avoid or at least reduce the challenge of growing larger functional tissues in vitro.

Figure 13:
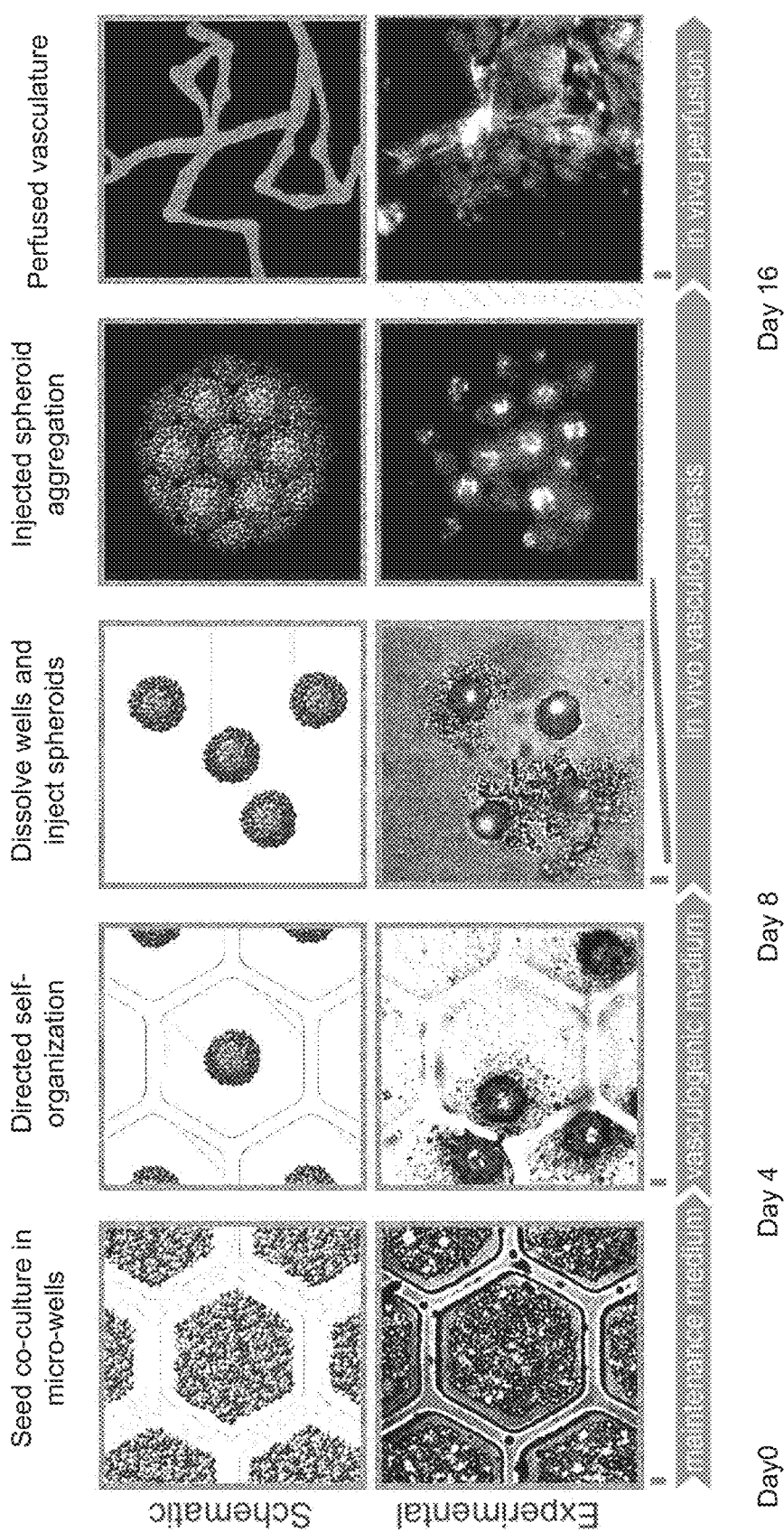
FIG. 13 shows a schematic diagram and results of spheroid fabrication method. Schematic diagrams and the corresponding experimental images showing the steps of spheroid fabrication and their final application. First, a co-culture of therapeutic cells and endothelial cells is seeded on the alginate microwells. Second, the cells are cultured in the microwells in maintenance medium without vasculogenic growth factors for 4 days, allowing the cells to self-organize into spheroids with an endothelial core. After the initial 4 days, the spheroids are cultured in the microwells in vasculogenic medium with vasculogenic growth factors for an additional 4 days, allowing the endothelial cores to mature into vessels. Third, the alginate microwells are dissolved with 5% sodium citrate to release the spheroids into suspension. Fourth, the suspension of spheroids may be spun down and assembled into a macro-tissue in vitro to study the vascular formation, or injected into the subdermis of a mouse demonstrate engraftment in vivo. Fifth, the injected spheroids were observed to form fully-functional and perfused microvasculature in vivo.

According to embodiments, a method for making spheroids includes, as illustrated in FIG. 13a was verified in a laboratory. A co-culture containing endothelial cells (of either mouse or human origin) was seeded in alginate micro-wells (see FIG. 19 and associated description for fabrication details). Second, the self-assembly and self-sorting of the endothelial cells into endothelial cores was directed by culturing them in maintenance medium without growth factors and these cores were matured into blood vessel units by culturing in vasculogenic medium. Third, the spheroids were harvested by gently dissolving the alginate microwells to release the spheroids. Fourth, the spheroids may be injected and used as a therapy without disrupting the blood vessel unit structure. Fifth, within 4-7 days the spheroids interconnect to each other and the host to form a fully-functional, perfused vascular network.

The above method is scalable for high throughput. The same number of steps can take a large number of cells harvested (FIG. 14a) limited only by the number of cells available for seeding (in examples, a quarter of a billion cells). One construct can produce more than 30,000 spheroids within a single 60 mm diameter petri dish (FIG. 14a), as they are seeded into the alginate construct (FIG. 14d).

Figure 20D:
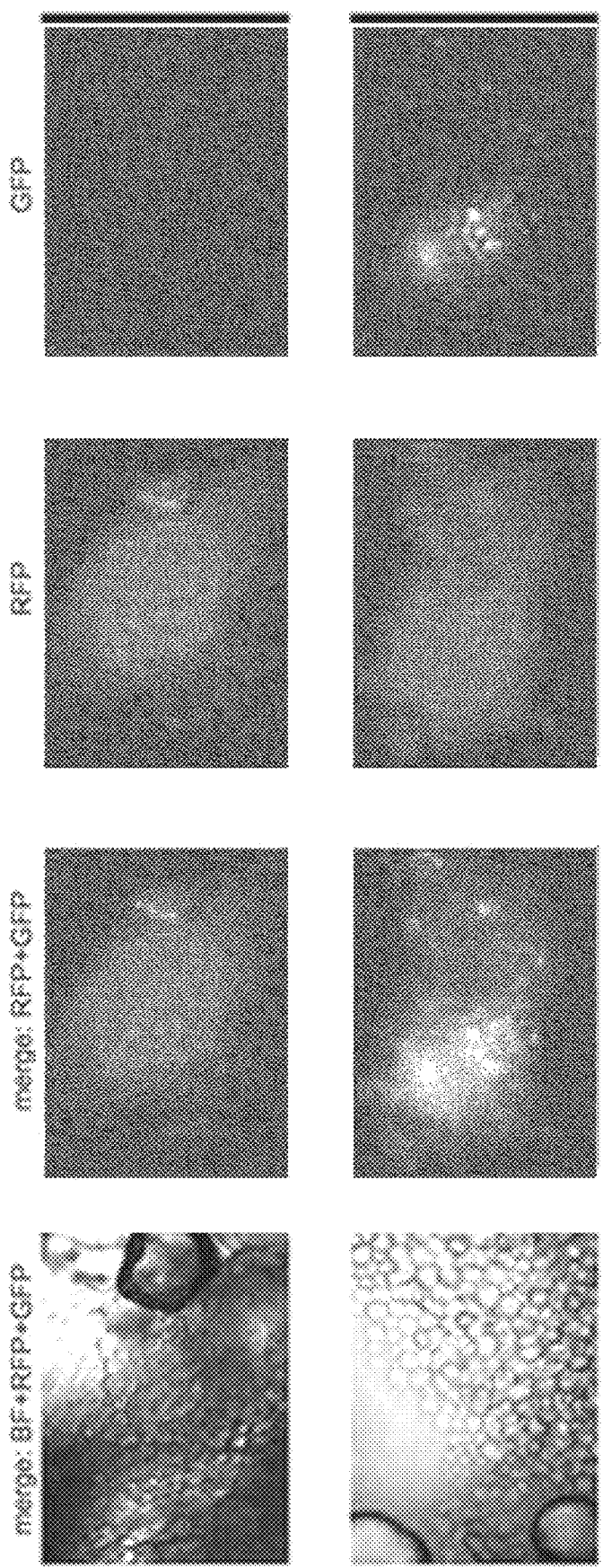
Figures 21A, 21B, 21C:
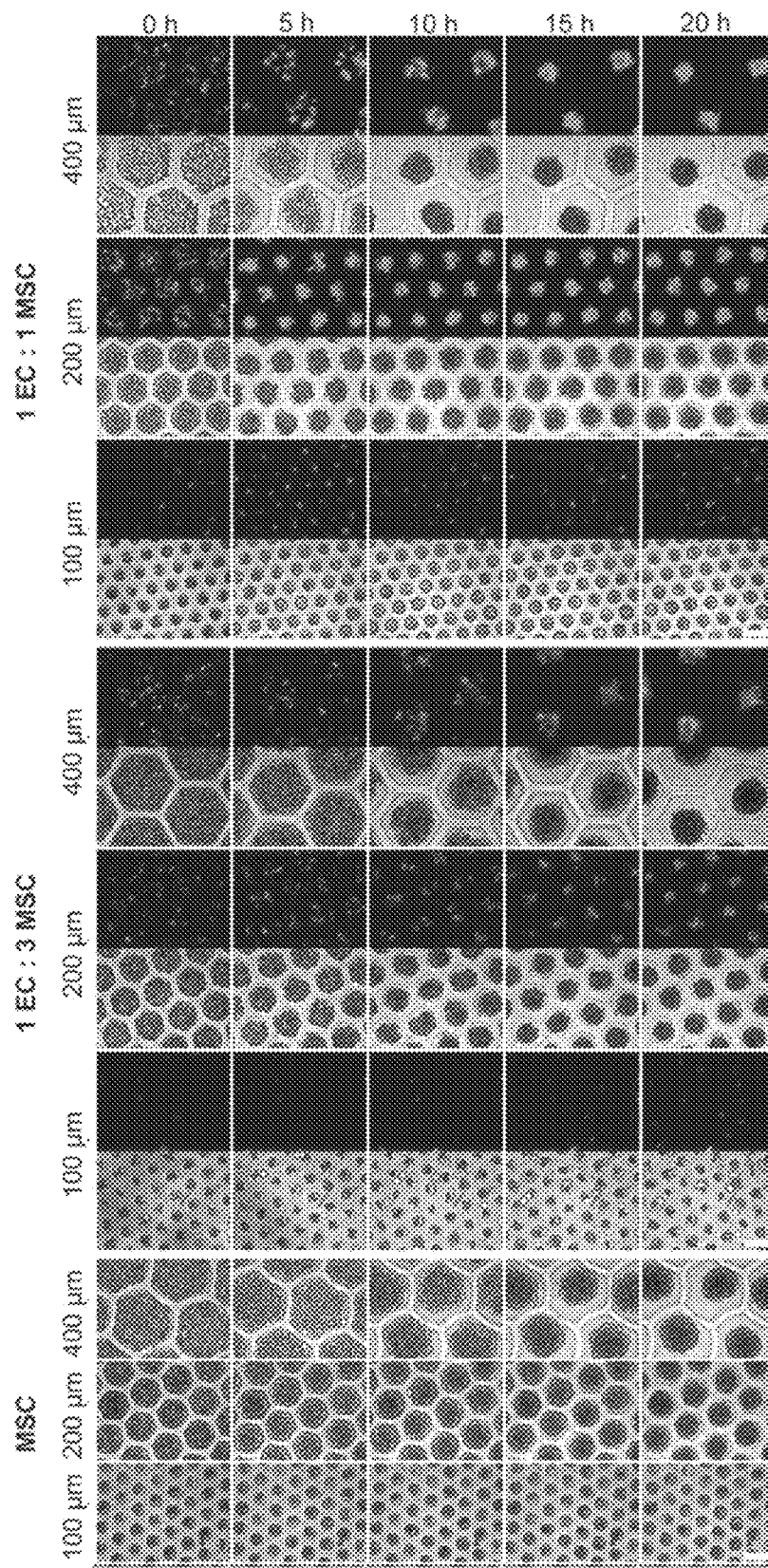
FIGS. 21A-C show an initial phase of spheroid formation and self-sorting. Shown are first 20 h of self-assembly and self-sorting immediately after seeding GFP-HUVEC and MSC cell mixtures in alginate microwells (100, 200, 400 µm). Fluorescent and brightfield images were acquired with a 10× objective. Scale bar=200 µm.
Figure 22:
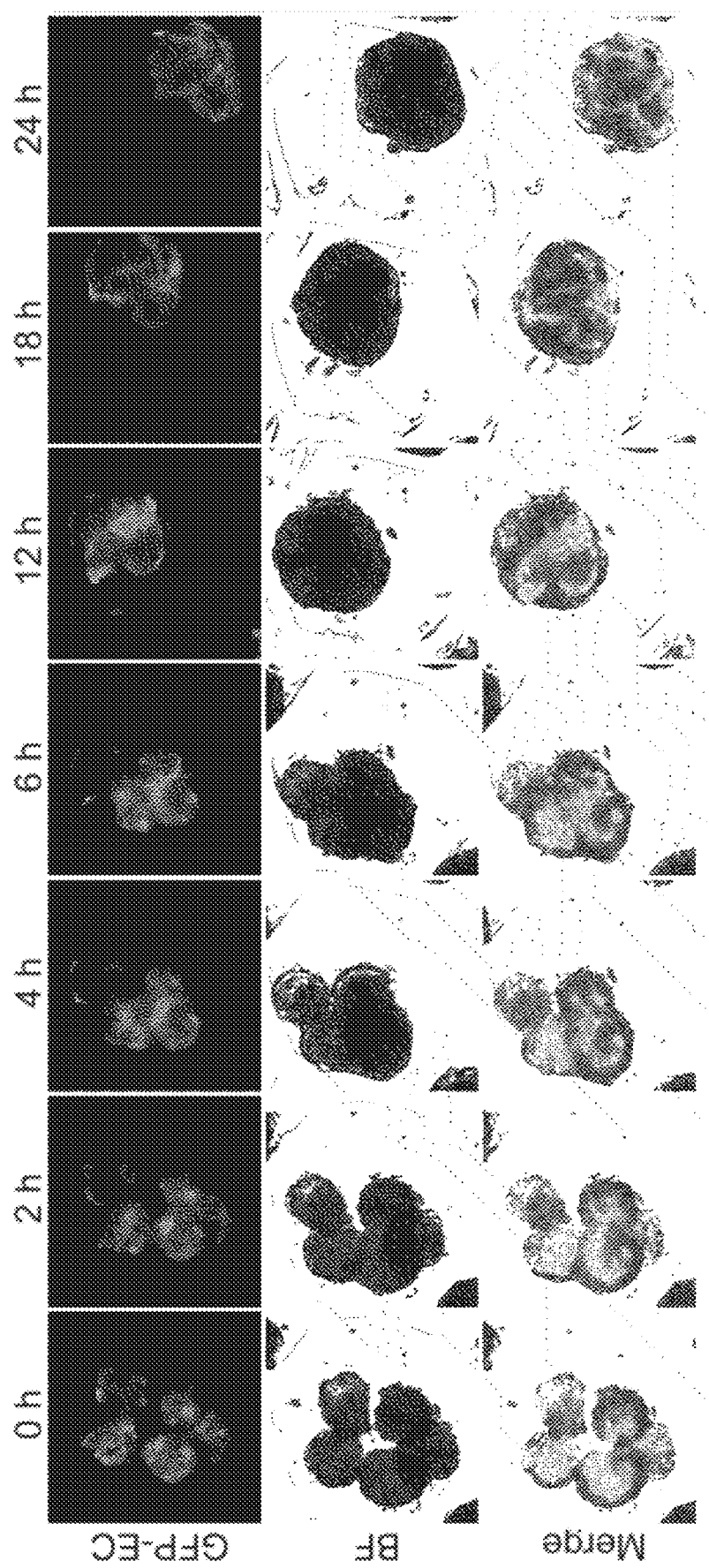
FIG. 22 shows spheroid fusion from microtissue to macrotissue: Spheroids were created in 200 µm sized microwells at 1:1 and 1:3 GFP HUVEC to MSC ratio and cultured for 3 days in maintenance medium and 6 days in a vasculogenic medium to induce prevascularization (see 0 h). For this assay the same vasculogenic medium was used. Prevascularized spheroids were placed in a collagen-alginate microwell. GFP fluorescence and brightfield images were acquired with a 10× objective in time-lapse microscopy over 24 h. Scale bar=200 µm.
Figure 23A:
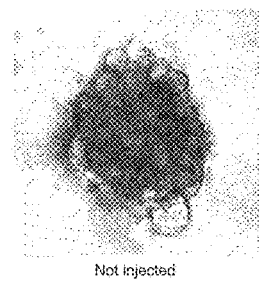
FIGS. 23A-23C illustrate robustness to shear stress: Images of spheroids before (FIG. 23A) and after injection through a 27 gauge needle (FIG. 23B) and a 30 gauge needle (FIG. 23C). Scale bar is 50 µm. It was determined that spheroids (clusters) remain intact
Figure 23B:
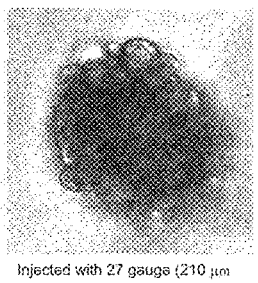
Figure 23C:
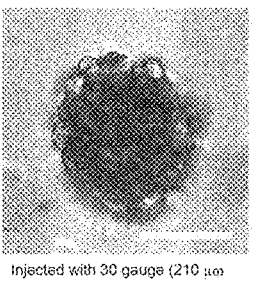

The use of alginate has several benefits. It is non-adhesive to cells, and it can also be uncrosslinked with a chelator that does not disrupt cell function. Uncrosslinking of alginate (FIG. 20) leaves the spheroids suspended in a solution, which can be gently pipetted into tubes, centrifuged and resuspended in whichever media is desirable for cell delivery, hence providing a gentle but effective way of harvesting the spheroids for future research or clinical use. This method of releasing the spheroids (compared to flipping the wells or squirting with saline) results in a controlled release of spheroids with high yield under low mechanical stress. Producing the spheroids in non-adhesive alginate allows the fabrication of a copious amount of spheroids in very little space with very little labor. These features were demonstrated in a laboratory.

Figure 15:
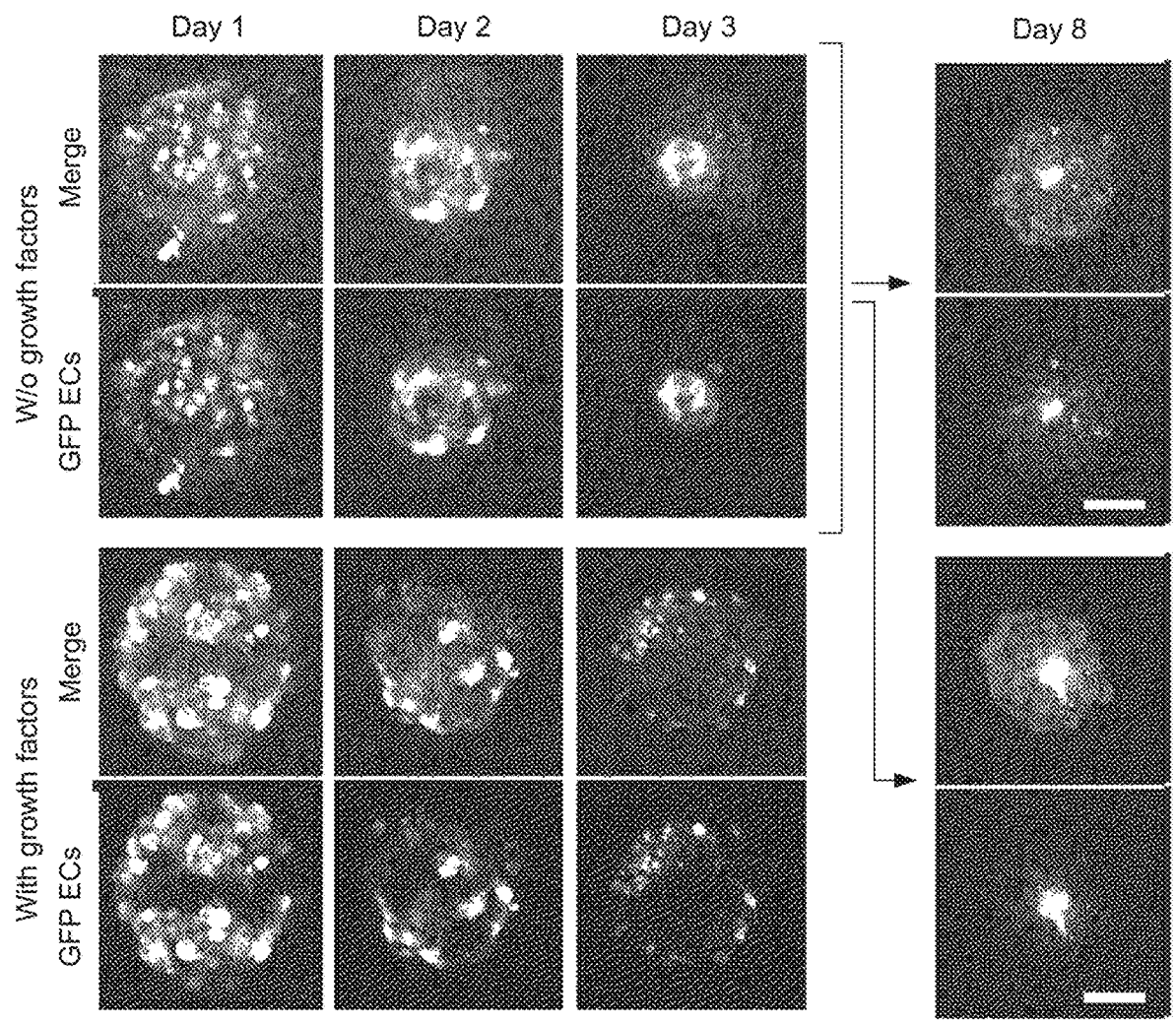
FIG. 15 shows endothelial cores formed by directed self-organization of the cells through timed exposure to growth factors. The first three days, culture in media without growth factors (VEGF and bFGF) induces the endothelial cells to migrate to the spheroid centers and form endothelial cores (top). After endothelial core formation, spheroids continuously cultured in media without growth factors will remain as endothelial cores (top right). Endothelial cores may be induced to mature and produce lumen and sprouts if growth factors are added to the media after the endothelial cores have formed (bottom right). Endothelial cells in spheroids grown in media with growth factors for the first three days migrate to the periphery of the sphere, do not form endothelial cores and cannot be prevascularizes.
Figure 19A:
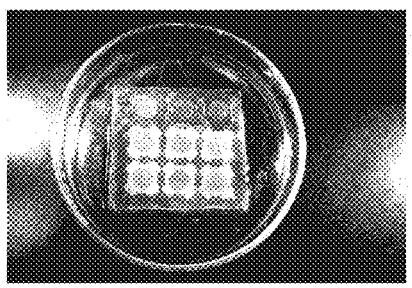
Figure 19B:
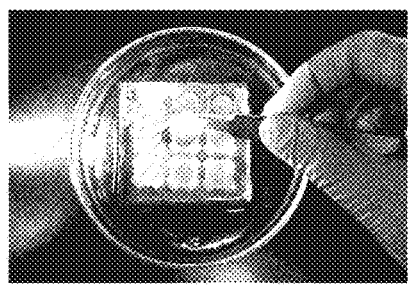
Figure 19C:
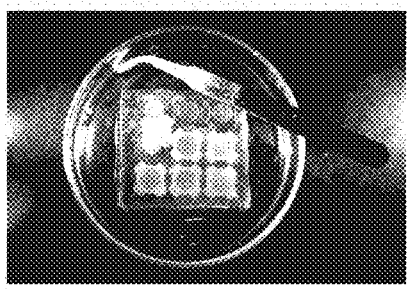
Figure 19D:
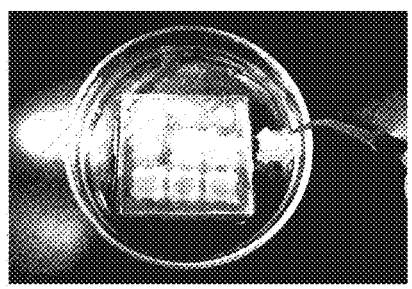
Figure 19D:
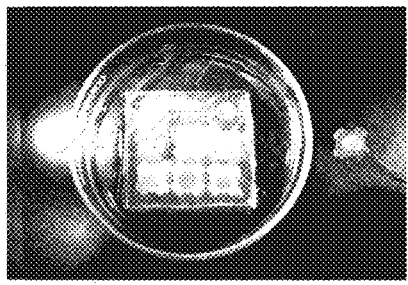
Figure 19F:
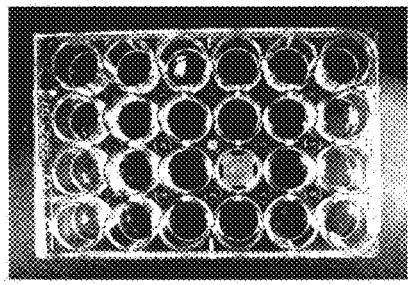

Second, a co-culture was established containing endothelial cells in the alginate microwells. The cells were then in a non-vasculogenic medium (e.g. in a co-culture of ECs and MSCs, an adipogenic medium). These conditions prompted the endothelial cells in these spheroids to self-organize, migrate to the center of the spheroid, and form an endothelial core within 3 days by culturing the spheroids in media without any exogenous growth factors (FIG. 15). After the endothelial cores formed, the spheroids' medium was changed to vasculogenic medium containing exogenous growth factors (VEGF and bFGF) to mature the blood vessel units. In this manner, a pre-vasculature was achieved within a spheroid that would promote vessel formation among the endothelial-cell cores upon implantation—or injection.

After incubation in a vasculogenic medium for 4 to 11 days, the spheroids were harvested by uncrosslinking the alginate wells. The spheroids could also be dislodged from the microwells with gentle flushing of media or ultrasaline, or by flipping the microwells upside-down in which case the spheroids are deposited in the same hexagonal pattern.

The spheroids were collected by centrifuging, removing supernatant, and resuspending. For example, the spheroids were collected on day 8 into a macroscopic tissue with surface area of 1 cm$^2$ and a height of 1 mm (FIG. 1E). Fluorescence imaging of this macroscopic tissue was performed (FIG. 13f). The images showed a high density of spheroids with endothelial-cell cores (ECs were labelled with GFP) throughout the tissue (containing RFP-labelled MSCs). Finally, the intact spheroids may be injected (e.g. into an animal model, subcutaneously in a window chamber, to observe in vivo assembly or into a collagen or other hydrogel to observe in vitro assembly); when injected in vivo, the endothelial cores in the spheroids connected to form a perfused vascular network.

The disclosed methods provide a stable culture technique which allows for easy medium change. This was utilized to direct the self-organization of co-culture spheroids and produce a large number of microtissues with blood vessel units, with high control over the size of the spheroid and size of the blood vessel unit. The self-organization of mouse endothelial cells in the spheroids was directed through the absence of exogenous growth factors (bFGF and VEGF). When co-cultures were first seeded and contracted into spheroids, the RFP-MSCs and the GFP-ECs were randomly distributed (FIG. 15a). When the co-culture spheroids were cultured without growth factors for 3 days, the endothelial cells migrated to the center of the spheroid and formed an endothelial core (FIG. 15a, top row). By contrast, this self-organization into endothelial cores in spheroids that were cultured in media with exogenous growth factors was not observed (FIG. 15a, bottom row). After the endothelial cores formed, the spheroids were cultured in vasculogenic media with exogenous growth factors. The exogenous growth factors caused the ECs in the core to sprout towards the surface and mature into vessels (day 8 or 10).

The methods can produce different spheroid sizes and mesenchymal-stem-cell-to-endothelial-cell ratios (FIG. 16a). Three different spheroid sizes were produced by cultivation in three different micro-well sizes (100, 200, and 400) resulting in spheroids with diameters of approximately 40, 80, and 160 µm, respectively. Experiments produced results for three different endothelial cell ratios: 3 endothelial cells to 1 mesenchymal stem cells (3:1), 1 endothelial cells to 1 mesenchymal stem cells (1:1), and 1 endothelial cells to 3 mesenchymal stem cells (1:3). The endothelial core formation is consistent for all of these ratios. Formation of these prevascularized spheroids as a three-by-three array for three key time points: 1) immediately after seeding at day 0; 2) after initial spheroid formation in basal media with distinct endothelial cores at day 3, after which the spheroids were cultured in a vasculogenic medium which; 3) at day 10 after 7 days of subsequent pre-vascularization by culture in vasculogenic medium with added exogenous growth factors (VEGF and bFGF) (FIG. 2B) that caused the cells in the endothelial core to mature into vessels and sprout towards the surface.

The methods allow for generation of primitive vascular architecture with high throughput and reproducibility of size. The formation of the EC-core and the size of the core and spheroid were highly reproducible (within 90%), as there was little variance over 50 spheroids in the distance of the most distal MSC to the center (FIG. 16b). Over time, the cells in the well contracted into a spheroid, while the distribution of endothelial cells showed migration of the ECs towards the core (FIG. 16b). In addition, the size of the spheroids could be controlled from 40 to 90 µm by controlling the seeding cell concentration and size of wells, such that the well size was big enough to contain the number of cells at initial seeding but small enough to ensure cell-cell contract to form a single spheroid rather than multiple spheroids. It was found that the size of the fully contracted spheroids (at day 2 and after) correlates to the number of cells in the spheroid (FIG. 16c). The diameter of the spheroids' cross-sections related to the number of cells in the spheroid and the cells typical volume, consistent with the relationship d=(6/π vcell ncell)1/3 (FIG. 16c). All spheroids self-assembled in the beginning of the in vitro cultivation period, with only minor changes in shape occurring after day 3. Spheroids contracted over the course of in vitro cultivation. This compaction was more pronounced for larger sizes. Smaller spheroids (100 μm) almost did not change their size. All spheroids were stable during the entire in vitro cultivation period and were uniform in shape.

Referring now to FIG. 17, which relates to HUVECs, human adipose-derived MSCs, to analyze the process of self-assembly and self-sorting, 1 EC:1 MSC cell suspension was seeded on non-adherent 400 μm alginate microwell (FIG. 17a) Immediately after placement in the recesses of the alginate mold, the cells were observed to start to migrate towards each other and cluster up. After 20 h, spheroids were formed.

EC/MSC self-sorting was analyzed. Initially the co-cultured cells were a randomly distributed layer of ECs and MSCs that then self-assembled and also self-sorted. Interestingly ECs first migrated to each other (see FIG. 17a, 5 h GFP image) and then migrated as larger EC units to form a central EC core covered in MSCs. Centrally placed ECs even migrated away from the center of the spheroid in order to cluster up with other ECs and afterwards returned to the center in a larger EC unit. Self-assembly and self-sorting were observed happening simultaneously.

To examine fully the self-assembly and self-sorting mechanisms of the spheroids over the whole in vitro cultivation period, and also investigate the effects of in vitro prevascularization, time-lapse microscopy was applied to image the spheroids over the course of 8 days (FIG. 17b). Cell suspensions of different ratios (1:1, 1:3, MSC only) were placed on non-adherent alginate constructs patterned with micromolds of different size (100, 200, 400 μm). Cells settled within the cavities and as mentioned above, self-sorting and also self-assembly happened immediately after seeding. Self-sorting happened until day 3. ECs migrated to the center of the spheroid forming an endothelial core surrounded by MSCs. Under vasculogenic stimulation, these ECs started to spread out from the endothelial core and formed sprouts and vessel-like structures throughout the entire spheroid as can be seen in the GFP-fluorescent images. Vessel-like structures spread throughout the entire co-cultured spheroid creating an early stage of a vessel network. This was observed to be more pronounced in larger co-cultured spheroids.

To examine the ability of the spheroids to form a macro-tissue in vitro, namely, creating a larger tissue from smaller tissues units, prevascularized and self-assembled spheroids were harvested from their initial alginate microwells and placed in a collagen-alginate microwell to observe their assembly (FIG. 17C). Over the course of the experiment, the outer border of the fused tissue became smoother and more compact. Spheroids attached to each other and contracted to form a larger spheroid. The coherently amalgamated macro-tissue was uniform in shape, had no distinguishable units and was stable throughout the entire experiment. Furthermore, in this experiment the ability to fuse the individual preformed vascular-like structures was examined. While initially forming an endothelial core and sprouting under vasculogenic stimuli, the already formed vessel-like structures connected to create one extensive endothelial cell network within the fused tissue. The individual networks became connected rapidly and spanned the whole macro-tissue. ECs maintained their ability to change architecture until the end of this experiment, which was observed by their continuous rearrangement within the macro-tissue.

Referring now to FIG. 18, to improve graft acceptance, SCID mice have been used to study the integration of a HUVEC/MSC xenograft. Self-assembled in 200 μm alginate microwells and prevascularized HUVEC/MSC spheroids were implanted. The spheroids were implanted by injection. Once the skin on one side of the window chamber was removed, the fascia on the remaining side was lifted up to allow for injection through the fascia and into the space between the facia and the subdermis. The spheroids created with the disclosed methods can be delivered by injection, as they can withstand the shear stress of injection through syringes (See FIG. 24). The range of shear to which spheroids attended injection at rates of 0.1 to 2 mL/min through 27ga (0.27 mm) and 30ga (0.159 mm). The disclosed embodiments may be limited to a spheroid (cluster) integrity of toughness that can survive this level of shear.

Day 0 shows post-operative images of the implanted micro-tissues (FIG. 18b). Similarly to in vitro experiments (FIG. 17c), the ECs started to sprout and connect to their adjacent spheroids. The endothelial cores of spheroids, which were not placed adjacent, did not form connections. A primitive vascular network formed at day 4. Between day 4 and day 7 this network matured, formed lumen, connected to the host vasculature, and became perfused, as indicated by the read arrowheads at day 7. A thin endothelial cell layer is seen in the fluorescent images enclosing the lumina. The lumina were blood-filled (as can be seen from FIGS. 18b and 18b with the co-localization of the lumina of the GFP-ECs). The dashed line (indicated at 410) points out blood-filled vessels. Stereoscopic images taken immediately after implantation until day 11 demonstrated the kinetics of vascular network formation (FIG. 18c). Day 0 gives an overview of the implant placement with the three types of spheroids; 1 EC:1 MSC, 1 EC:3 MSC, and MSC only. The vascular structure for 1 EC:1 MSC and MSC only are shown for day 4, 7, 9, and 11. Until day 4 newly formed red blood cell filled vessels are hardly seen. Between day 4 and day 7 vessel formation intensifies massively in the pre-vascularized spheroids, the implanted vasculature becomes perfused and functional. After day 7 the blood filling in the vessels becomes more prominent and intense. The vascularization is only seen in pre-vascularized spheroids. Spheroids contain MSCs-only remained unvascularized throughout the extent of the experiment (28 days).

One can determine that the origin of the newly formed vessels are the endothelial cores in the implanted spheroids, as these ECs lining the newly formed vessels are GFP labelled (FIGS. 18b and 18d) and co-localize with the new vessels in the grayscale images (FIG. 18b). It is inferred from this observation that a rudimentary vessel is formed during in vitro cultivation and this is identified as a lumen structure, although such a structure has not been consistently observed through direct imaging.

Maximum projection of confocal images taken of the GFP-labeled endothelial cells of EC/MSC spheroids in a spatially defined window chamber insert on day 1 and 11, also show that the endothelial cells in the prevascularized spheroids interconnected to form a vascular network whose spatial dimensions were controlled.

The embodiments employing microwells can achieve high throughput. To make a comparison, several iterations of the hanging drops have been developed in an attempt to semi-automate the production or at least make it less labor intensive (Perfecta3D 96 well hanging drop plates or Trevigen's 96 well spheroid formation plate), but even with these developments, the scalability is still severely limited by the number of wells—96 or 384. Using the smallest constructs illustrated in FIG. 1c which produces 1000 spheroids, one can produce 24,000 spheroids rather than 96 spheroids in the same area and with fewer steps than these hanging drop iterations. That is a 60-250 fold increase in throughput.

As presently disclosed, a spheroid method embodiments are high throughput (and simple, so it may be automated). The spheroid method may be relevant for both 1) therapy production and 2) various research purposes, such as developmental biology. For example, developmental biologists use stem cell spheroids to check pathways, differentiation protocols, etc. and this would speed up their screening/characterization process. Their focus is usually organogenesis—which all happens in the vicinity of blood vessels. An interaction, which is completely neglected in current published studies.

As presently disclosed, a high throughput approach to spheroid production is minimally labor intensive and will make it possible to produce enough spheroids that they could constitute an actual treatment.

It has been demonstrated that it is possible to direct the EC's self-organization by co-culturing the spheroids with MSCs in non-vasculogenic medium without growth factors. It is believed that at the initial formation of the spheroid on day 1 the cells at the center of the spheroid exude endogenous growth factors that guide the endothelial cells on the spheroid's periphery to the center, so the cells self-organize to a spheroid with an endothelial core and a shell of mesenchymal stem cells. This shell provides the 3D structure within which the endothelial core can form and the polarity necessary for correct lumen formation. In addition to providing therapeutic cells, the mesenchymal shell also apparently protects the endothelial structure from shear stress during injections through 25 to 30 gage needles (Supplementary FIG. 5). Known spheroids may be torn apart by the shear stress attending injection. The mesenchymal stem cells in the shell may serve two additional purposes: (1) they can act as an immune suppressive shield and (2) may also provide additional angiogenic signaling. The shell can also be formed with other cell types such as fibroblasts or fat cells.

As presently disclosed, an injectable prevascularized spheroid can have many medical applications. They may be used to deliver therapeutic cells (in the cases presented here MSCs can be delivered as a treatment of Crohn's disease and MSCs differentiated into brown adipose tissue could be used for facial reconstruction or as a treatment for obesity and diabetes).

A hindrance to known cell therapies may be the low survival rate of the injected therapeutic cells. Using disclosed methods to produce prevascularized spheroids of therapeutic cells may increase their survival and treatment potential since the injected micro-tissues would vascularize quicker. The disclosed injectable prevascularized spheroids connect to form functional micro-vasculature within 4 days, and may also be used to treat ischemia and non-healing wounds by directly delivering new micro-vasculature to the affected tissue with injections.

The method does not require any initial scaffold to construct spheroids, as any extra cellular matrix will be endogenously produced by the therapeutic and endothelial cells. Scaffold free approaches may be easier to get into clinical trials and through regulatory approval.

In embodiments, the cells are seeded onto a non-adhesive hydrogel, preferably alginate or other material to which the cells do not adhere and further preferably a material that can release the cellular spheroids after a period of in vitro cultivation. In an example, an alginate construct with 379 to 30,000 microwells is used. The cells settle into these microwells, and the alginate provides no adherence structure for the cells. Further the cells have been demonstrated to adhere strongly to each other forming spherical cell aggregates over the initial 24 hours.

EXAMPLES

The alginate microwells may be cast from hydrophilic PDMS molds. In examples, master molds were fabricated in SU-8 (SU-8 3050, Microchem, Newton, Mass.) on 3-inch Si wafers (Silicon Sense, Nashua, N.H.) by photolithography as described before 34 to cast polydimethylsiloxane (PDMS, Sylgard 184, Essex Brownell, Fort Wayne, Ind.) replicas from the masters. The PDMS molds were made hydrophilic by plasma treatment, and submerged them in distilled water to retain their hydrophilicity. The PDMS molds were autoclaved prior to casting alginate.

A 2% w/v alginate (Pronova UltraPure MVG, NovaMatrix, Drammen, Norway) was prepared and autoclaved in HEPES saline buffer solution (Ultrasaline A, Lonza, Basel, Switzerland). The alginate was pipetted into the PDMS molds. Positive-displacement pipettes were used for accurate pipetting of viscous alginate solutions and to avoid bubbles. The top of the molds were closed with cellulose dialysis membranes (6000 D MWCO), and flattened the membranes using the edge of a sterile glass slide. A 60 mM $CaCl_2$ HEPES buffer solution was pipetted on top of the membrane for at least 60 min to crosslink the alginate at room temperature. The hydrogels were removed from the molds using sterilized tools, and placed the hydrogels in HEPES saline buffer solution (Ultrasaline A, Lonza, Basel, Switzerland) supplemented with 1.8 mM $CaCl_2$ (to prevent leaching of the calcium ions from the hydrogels). The alginate hydrogels were transferred into sterile culture ware, such as 24-well plates (Fisher Scientific, Fair Lawn, N.J.) with the open micro wells facing up and stored them at 4° C. until further use.

GFP-labelled human umbilical vein endothelial cells (GFP-hUVECs) (Angioproteomie, MA, USA) were cultured in Endothelial Growth Medium 2 (PromoCell, Heidelberg, Germany). Adipose derived human mesenchymal stem cells (hMSCs) (Promocell, Heidelberg, Germany) were cultured in Mesenchymal Stem Cell Growth Medium (Promocell, Heidelberg, Germany). The RFP-labelled mouse mesenchymal stem cells (RFP-mMSCs) (Cyagen, CA, USA) were cultured in DMEM with 10% FBS and 1% PenStrep (all from LifeTechnologies). All cells were gently passaged at 80-90% confluency using TrypLE (LifeTechnologies) and used only until passage P6 and mMSC until P8. Cells were cultured in 37° C. and 5% $CO_2$-balanced, humidified atmosphere.

HUVECs and MSCs were harvested from 2D cell culture, counted and desired cell ratios of HUVECs to MSCs were prepared: MSC only, 1 HUVEC to 3 MSC, 1 HUVEC to 1 MSC and 3 HUVEC to 1 MSC.

Then the 1.8 mM $CaCl_2$ solution that the alginate microwells were stored in was removed, and replaced with DMEM (ATCC, Manassas, Va.). The microwells were then placed in the incubator at 37° C. and 5% $CO_2$ to equilibrate for at least 20 minutes. Then DMEM was removed and the microwell constructs gently dried using surgical spears (Braintree Scientific, Braintree, Mass.) leaving the microwell features covered.

Cell suspensions were then pipetted on to alginate molds of 100, 200 and 400 µm microwell size using a positive displacement pipette. Cells were left to settle to the bottom of the microwells for 20 minutes and the culture wells were then filled up with culture medium.

The first 3-4 days after seeding, the cells were cultured in maintenance medium: Dulbecco's Modified Eagle Medium (DMEM) with 10% Fetal Bovine Serum (FBS) and 1% PenStrep (all from LifeTechnologies), with 50 µg/mL Sodium L-ascorbate (Sigma-Aldrich). For FIGS. 17 and 18, the maintenance medium also included 20 mM Hepes (Fisher Scientific, Fair Lawn, N.J.), 1 µM Insulin (LifeTechnologies, Carlsbad, Calif.), 250 nM T3, 1 µM dexamethasone, 0.5 mM IBMX, 50 µM Indomethacine, 1 µM Rosiglitazone and 1 µM CL316243 (all from Sigma, St. Louis, Mo.). After the first 3-4 days, the media was changed from maintenance medium to vasculogenic medium: Dulbecco's Modified Eagle Medium (DMEM) with 10% Fetal Bovine Serum (FBS) and 1% PenStrep (all from LifeTechnologies), with 50 µg/mL Sodium L-ascorbate (Sigma-Aldrich), 40 ng/mL bFGF and 40 ng/mL VEGF recombinant human protein (both from LifeTechnologies). For FIGS. 17 and 18, the vasculogenic media also included 20 mM Hepes, 1 µM Insulin, and 250 nM T3. The spheroids were cultured in vasculogenic medium up to day 11. Spheroid media was changed every other day.

To test the ability of spheroids to assemble in vitro and fuse to a larger tissue, 200 µm sized spheroids of pure MSCs, 1 EC:3 MSC and 1 EC:1 MSC ratio were placed in a 400 µm sized microwell composed of 3.5% collagen and 1% alginate. These spheroids had previously been prevascularized as described above. Spheroid fusion was conducted in vasculogenic medium and observed for 24 h.

Window chamber surgeries were conducted. In brief, a titanium window chamber (APJ Trading, Ventura, Calif.) was surgically implanted midline on the dorsum of male SCID mice (strain: ICRSC-M-M, 5-6 weeks of age, Taconic, Hudson, N.Y.) after hair removal and ethanol and iodine disinfection. To reduce variability between mice prevascularized and non-prevascularized spheroids were implanted in individual compartments of the same window chamber. Spheroids were delivered by injection and pipetting underneath the fascia of connective tissue to the subcutaneous adipose tissue. Window chambers were closed with a circular glass cover slip and a retaining ring (APJ Trading, Ventura, Calif.). A custom-made 3D printed window chamber backing was attached to reduce skin movement in the window chamber. In a subset of experiments, a custom-made ultem plastic 9 well array was screwed onto the front frame of the window chamber to allow for high throughput in vivo testing. Here, spheroids were placed into one of the 9 wells.

Animals were housed aseptically in frog cages to allow for enough clearance for the window chamber while still permitting easy access to standard laboratory chow (Irradiated globle rodent diet, Fisher Scientific, Fair Lawn, N.J.) and drinking water ad libitum. Follow up buprenorphine administration (0.1 mg/kg bodyweight) for pain management was given subcutaneously every 6-12 hours after surgery for the next 2 days post-OP. $CO_2$ euthanasia and cervical dislocation were performed after 30 days or earlier if necessary.

The animal procedures were approved and carried out in accordance to local regulations and authorities. The surgeries were conducted in aseptic technique.

A Leica DMI 6000B inverted microscope with 4× and 10× objectives, equipped with a motorized stage (Leica Microsystems, Bannockburn, Ill.) and a QImaging Retiga 2000R monochrome camera (QImaging, Surrey BC, Canada) was used to acquire fluorescence and brightfield images (FIG. 17 and FIG. 18). Leica LAS X software was used for image acquisition. Cropping, color adjustments and contrast enhancements of images as well as Z-stack projections were performed in ImageJ image analysis software. For time lapse imaging of spheroid formation and spheroid fusion an environmental chamber was used to maintain 37° C. and 5% $CO_2$. Images were acquired every 30 min. Confocal images of the window chamber were taken using a Leica SP5 confocal system with a 10.0×0.30 N.A. objective. Due to the stressfulness of the imaging procedure, in vivo images were acquired every 2-3 days. Fluorescent and grayscale overview images of the window chamber (FIG. 4 d) were acquired with a CRi Maestro 2 in vivo Imaging System. To be able to image the window chamber mice were anesthetized with isoflurane.

To observe individual spheroids precisely (FIGS. 13-16), Stacks of confocal images (1024×1024 pixels, 41 images with a z-spacing of 0.25 microns) were taken using a Leica SP5 confocal microscope, with a 100×1.43 N.A. oil immersion objective (Leica Microsystems) at a resolution of 0.132 µm/pixel (image stacks were thus 135 mm*135 mm*10 mm). The differential interference contrast (DIC) images as well as the RFP- and GFP-signal were simultaneously collected.

To collect spheroids the alginate hydrogel was uncrosslinked. For this, the culture medium of the spheroids was replaced with 5% w/v sodium citrate solution for approximately 20 min. This chelator liquefied the alginate, and allowed for resuspension of the spheroids in a desired medium. Spheroids were then centrifuged at 300 rpm for 5 minutes or as specified and the spheroid pellet carefully collected for further use.

The media was gently removed from the microwells. The alginate microwells were uncrosslinked with 200 µl of 5% sodium-citrate, releasing the fully-formed spheroids into suspension. The suspension was gently spun down at 220 g for 5 minutes. The supernatant was removed and the spheroids resuspended in 0.5 ml vascularization media (DMEM with 10% fetal bovine serum (FBS), 1% PenStrep, 20 ng/mL ascorbic acid, 20 ng/mL vascular endothelial growth factor (VEGF) and 20 ng/mL basic fibroblast growth factor (bFGF). The spheroids were then spun down again at 220 g for 10 minutes and left in the incubator for an hour to form primary cell-cell adhesions between the spheroids to form macroscopic aggregates. The aggregates were gently tapped free of the tube bottom and the whole tube content (tissue-aggregate and vascularization media) was up-ended and transferred into an imaging well. The tissue-aggregates were cultured for an additional 10 days in vitro with a vascularization media change every other day.

Spheroids were collected as described above. The suspension was gently spun down at 220 g for 5 minutes. The supernatant was removed and the spheroids resuspended in 200 µl PBS. This solution was injected on to a mouse's open window chamber under sterile conditions and closed.

In vitro created, prevascularized and non-prevascularized spheroids were implanted in a window chamber to allow for continuous in vivo monitoring of the vascularization and integration process.

All tools, surgical instruments and window chambers were autoclaved. Surgical procedures were done in a laminar flow hood in aseptic technique to reduce risk of contamination and infection. Surgeons were wearing an apron (Kimberly-Clark isolation gown, Fisher Scientific, Fair Lawn, N.J.), a hair net (Fisherbrand bouffant caps, Fisher Scientific, Fair Lawn, N), and a surgical facemask (Kimberly-Clark classic surgical facemask, Fisher Scientific, Fair Lawn, N.J.). Because mice can lose a significant amount of body temperature during surgery, a 42° C. warm water heating pad (heated hard pad, Gaymar warm water pump, both from Braintree Scientific, Braintree, Mass.) was used.

Animal cages were disinfected with MB10 (Quip Laboratories) and opened in a laminar flow hood. Bodyweight was measured. For anesthesia Ketamine/Xylazine was injected intraperitoneally using a concentration of 80-100 mg/kg ketamine and 5-10 mg/kg xylazine (both from Butler Schein, Melville, N.Y.). For maintenance of anesthesia an additional dose of 30% of the original dose of ketamine was given. To monitor the depth of anesthesia toes were pinched every 5 minutes. The mouse eyes were covered with eye gel (Fisher Scientific, Fair Lawn, N.J.) to avoid damage. Hair removal at the surgical site was then done with an electrical animal hair trimmer (Braintree Scientific, Braintree, Mass.). The mouse was then placed on an animal restraint plate (Small animal surgery board, Braintree, Scientific, Braintree, Mass.). Sterile gloves (Fisher Scientific, Fair Lawn, N.J.) were put on. The surgical site on the mouse's dorsum was disinfected twice with scrubbing solution (Betadine surgical scrubbing solution, Fisher Scientific, Fair Lawn, N.J.) followed by cleaning with 70% ethanol. Then buprenorphine (between the scapulae, 0.1 mg/kg body weight) and lidocaine (at the surgical site, 5 mg/kg body weight) (both from Butler Schein, Melville, N.Y.) were injected subcutaneously. Mouse disinfection was then finished with the application of another round of scrubbing solution and ethanol and completed with application of prepping solution (Povidone iodine prepping solution, Fisher Scientific, Fair Lawn, N.J.) at the surgical site. Sterile gloves were changed and marked the completion of the animal preparation.

Figure 24A:
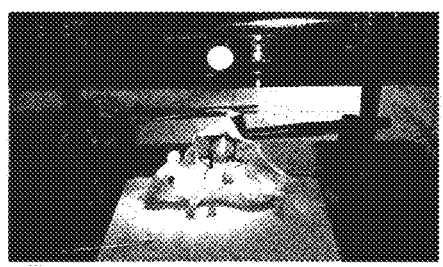
FIGS. 24A-24F show window chamber surgery.
Figure 24B:
Figure 24C:
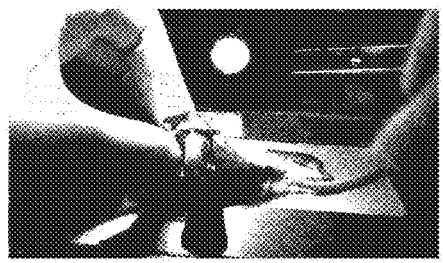
Figure 24D:
Figure 24E:
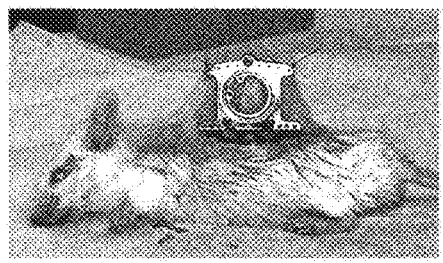
Figure 24F:
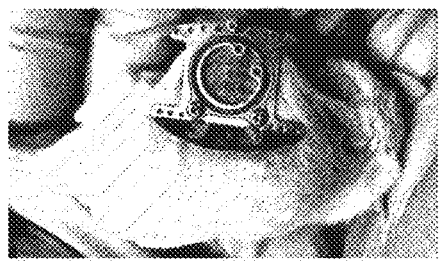

The mouse was placed parallel underneath the bar (custom made in lab) of the animal restraint plate. Three sutures (4.0 non-absorbable nylon suture, Fisher Scientific, Fair Lawn, N.J.) were placed to the front, middle and end of the back to spread out the skin of the dorsum and guided over the metal bar of the animal restraint plate. The middle suture was used as guidance to connect the backside of the window chamber (Window chamber kit, small, APJ Trading, Ventura, Calif.) to the skin. Sharp 18 G hypodermic needles (Fisher Scientific, Fair Lawn, N.J.) were inserted in blunt 15 G dispensing needles (McMaster-Carr, Atlanta, Ga.). The 18 G needles were used to penetrate the spread out skin where holes were needed for window chamber attachment and to push the blunt needles through the skin. Once holes were made, the 18 G needles were removed comparable to "mandrin techniques" and only the 15 G blunt needles were left in place. A piece of PDMS was used to facilitate the piercing of the skin (FIG. 24a). The light of a led lamp (Fisher Scientific, Fair Lawn, N.J.) was used to indicate the inner opening of the window chamber on the mouse and show major vessels under the skin. This shadow was encircled with a marking pen (Fisher Scientific, Fair Lawn, N.J.) and the. skin area was then disinfected as mentioned above. Next a subcutaneous lidocaine injection at the surgical site followed. A new set of sterile gloves was put on. The circular marked skin was then cut out with surgical scissors and Adson tissue forceps (both from Fisher Scientific, Fair Lawn, N.J.) (FIG. 24b). Next the screws of the assembled front part of the window chamber were inserted into the blunt needles. Pushing together the front and back parts of the window chamber assembled it (FIG. 24c). Each screw was locked with a nut. All initial sutures were removed after secure window chamber frame placement. Next the site of implantation was prepared. The fascia of the subcutaneous tissue was carefully excised avoiding damage to the host tissue and vasculature. A magnifying camera and monitor were used to increase accuracy. Last remaining layers of fascia were lifted and prior collected spheroids were injected underneath. The window chamber was separated in up to 3 compartments to inject 3 different conditions simultaneously. To avoid air bubble entrapment in the window chamber, which could decrease imaging quality, the window chamber was filled up with Ultrasaline A (Lonza, Basel, Switzerland). The window chamber was closed by layering a glass slide on top and securing it with the retaining ring of the window chamber kit. A custom made, 3D printed holder was screwed on the window chamber and held in place with additional nuts (FIG. 24d) ensuring a tight seal of the window chamber to the skin. Sutures were placed in lateral holes of the window chamber frame to secure placement (FIG. 24e). As described above, to reduce variability between mice 3 conditions were injected into one window chamber. This concept of simultaneous implantation was extended and in a different set of experiments a 9 well ultem plastic array was milled, and inserted into the window chamber (FIG. 24f). This insert only changed the final steps of the window chamber protocol. Here, fascia was completely removed and spheroids were directly pipetted into one of the 9 wells of the insert.

EXAMPLE

Figures 25A, 25B:
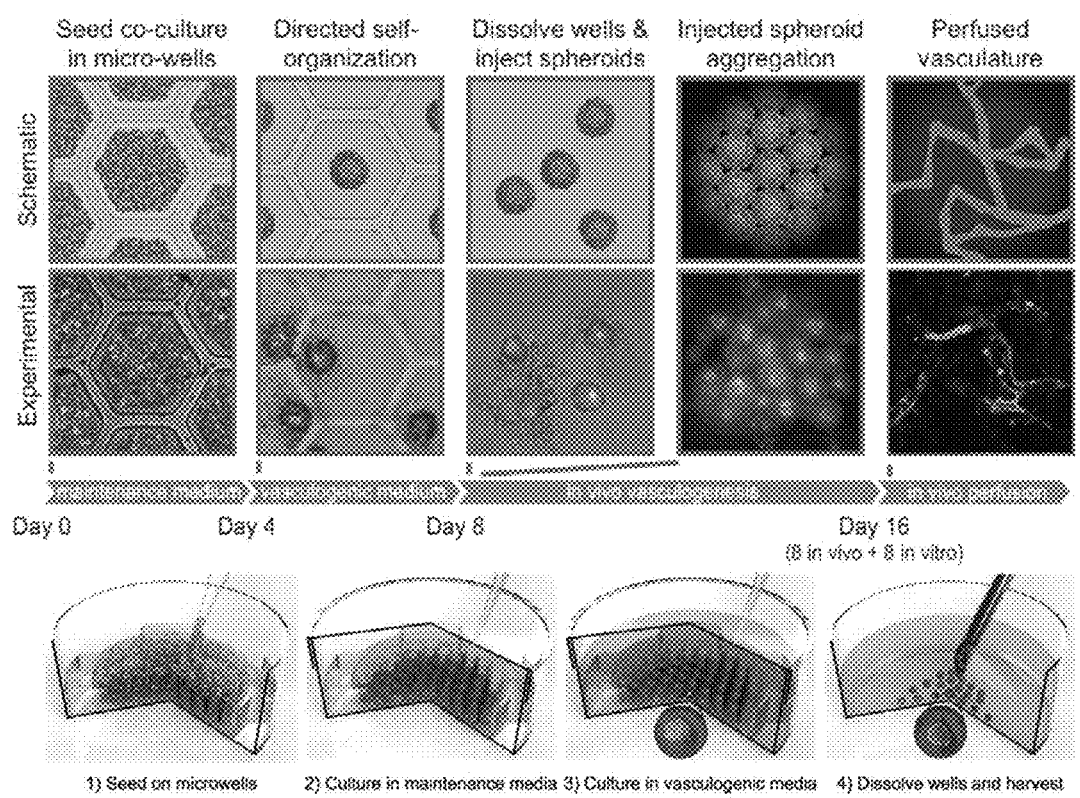
FIGS. 25A-25B are a schematic diagram and results of prevascularized microtissue fabrication method.

High-Throughput Method for Producing and Harvesting Microtissues: Robust, Gentle, and Scalable A large number of prevascularized microtissues was engineered and harvested in four steps (FIG. 25a). First, a co-culture containing ECs and MSCs (of either mouse or human origin) was seeded in dissolvable alginate microwells (see Fig. S1 for fabrication details). Second, the cells were cultured in media without growth factors ("maintenance" medium), followed by a vasculogenic medium with growth factors to induce sprouting. Third, the microtissues were gently harvested by dissolving the alginate microwells. Fourth, the microtissues, which contained blood-vessel structures, could be further manipulated in vitro or injected in vivo.

The use of alginate for microwells has several advantages: it is non-adhesive to cells (enabling cells to contract into microtissues), and importantly, it can also be uncrosslinked with a chelator in a manner that does not significantly disrupt cell function. The use of alginate as a sacrificial template permits gently harvesting large numbers of microtissues (FIGS. 25 a-b), leaving microtissues floating in solution. The microtissue solution could be gently pipetted into tubes, centrifuged and resuspended in a culture medium suitable for downstream manipulation or direct cell delivery. Each step is simple (FIG. 25b) and can be conducted with sterile liquid handling and automated.

This method is highly scalable in terms of the number of microtissues to be produced. The same small number of steps (FIG. 25b) can harvest large number of microtissues by using constructs with large numbers of microwells.

As an example, three different sizes of alginate microwell inserts for culture dishes were demonstrated (FIG. 26a): 15.6 mm-diameter inserts containing >1000 microwells (yielding >24,000 microtissues on a 24-well plate), 22.1-mm inserts containing >3000 microwells (yielding >36,000 microtissues on a 12-well plate), and a 60-mm diameter insert containing >30,000 microwells in a 60-mm culture dish. If desired, the inserts can be stacked to increase the number of microtissues produced in the same area with additional media changes.

This massive parallel production of more than 30,000 microtissues was demonstrated by seeding a quarter of a billion cells (FIG. 26b) in one 60-mm dish insert (FIG. 26c), and assembling the microtissues into a macrotissue (FIG. 26d). RFP-labelled MSCs and GFP-labelled ECs were co-cultured for four days. The microtissues were then gently harvested by uncrosslinking the alginate wells and assembling them into a macroscopic tissue with surface area of 1 cm² and a height of 1 mm (FIG. 26d). Fluorescence imaging of this macroscopic tissue was performed (FIG. 26e). The microtissues were densely packed, and exhibited distinct endothelial cores, confirming that the gentle harvest and assembly did not disturb the internal architecture of the microtissues. The assembled macrotissue, consisting of fully contracted microtissues, did not visibly contract during subsequent in vitro culture.

EXAMPLE

Formation of Pre-Vascularized Microtissues with Size Control

Figure 27C:
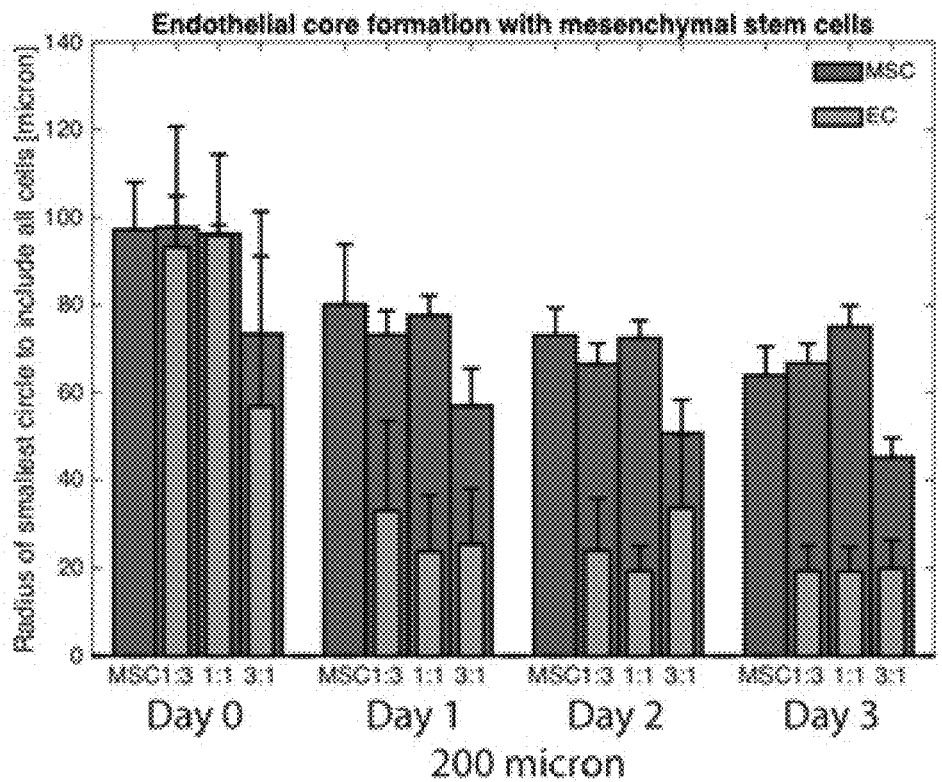
Figure 28A:
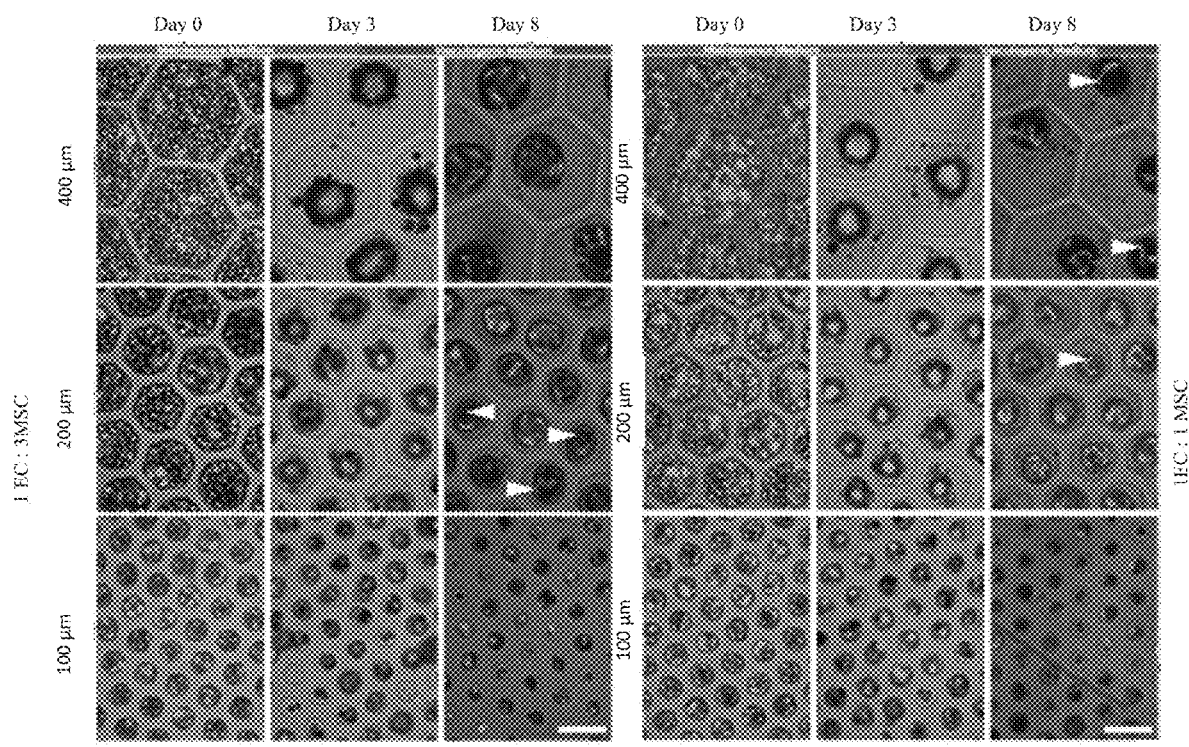
FIGS. 28A-28C illustrate maturation of microtissues with human cells.
Figure 32C:
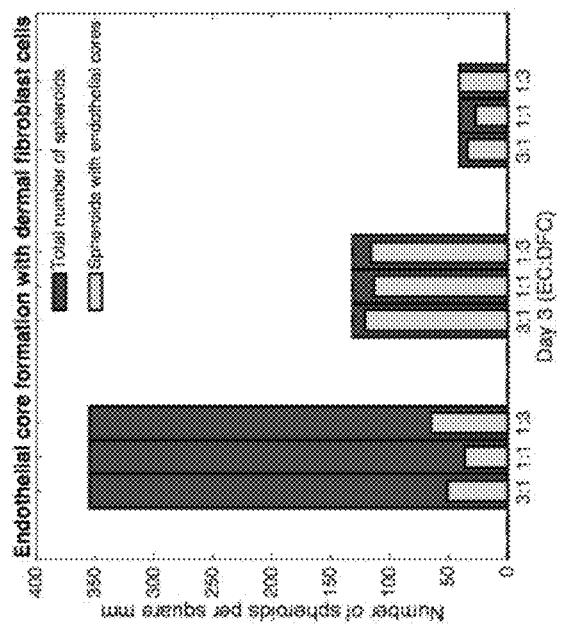
FIGS. 32A-32C illustrate endothelial core formation in co-culture with HUVECs and human dermal fibroblast cells (hDFCs).
Figure 32B:
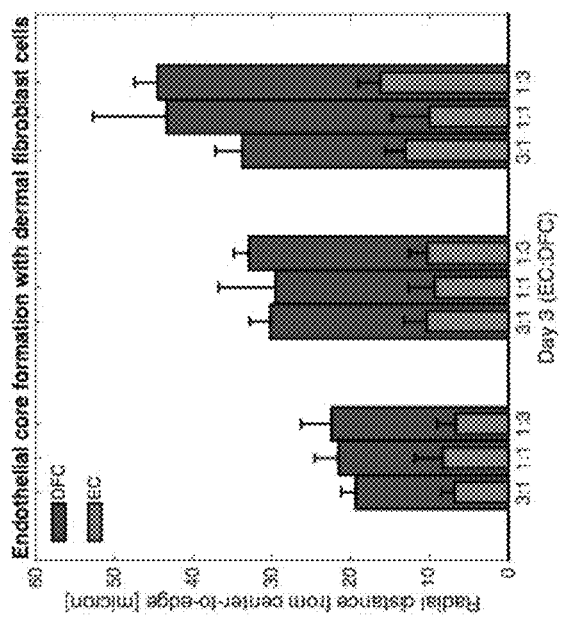
Figure 32A:
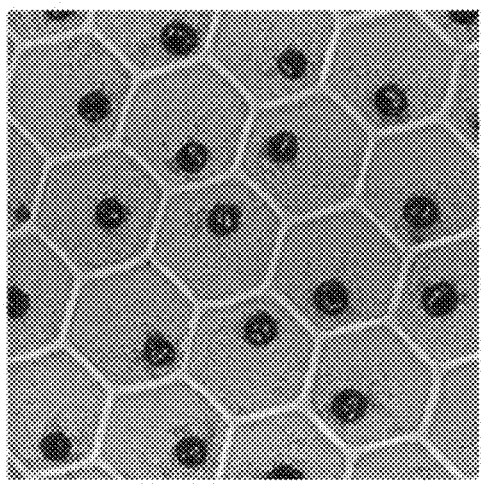

Next, it was studied whether the sizes and internal architectures of microtissues could be controlled reproducibly. In the absence of exogenous growth factors, it was observed that GFP-labelled human umbilical vein endothelial cells (HUVECs), which were initially randomly distributed alongside RFP-labelled mouse MSCs, migrate to the center of the microtissues and form endothelial cores after culture in the "maintenance" medium for 3 days (FIG. 27a, top panel). Similarly, ECs also formed endothelial cores when co-cultured with another cell type (fibroblasts) in a medium without growth factors (FIG. 32), the endothelial cores were more pronounced than in a previous observation. By contrast, ECs did not migrate to the center when the microtissues were cultured in a vasculogenic medium containing 50 ng/mL VEGF and 50 ng/mL bFGF (FIG. 27a, bottom panel), consistent with a previous observation. After formation of endothelial cores in a maintenance medium, switching the culture of microtissues to a vasculogenic medium resulted in formation of lumens within the center of the microtissue, with sprouting and maturation of vessels towards the surface apparent after 5 days of culture in vasculogenic medium (FIG. 28a). Overall, the data showed the microtissues to exhibit reproducible internal architectures containing endothelial cores, lumens and sprouting of vessels.

Figure 33:
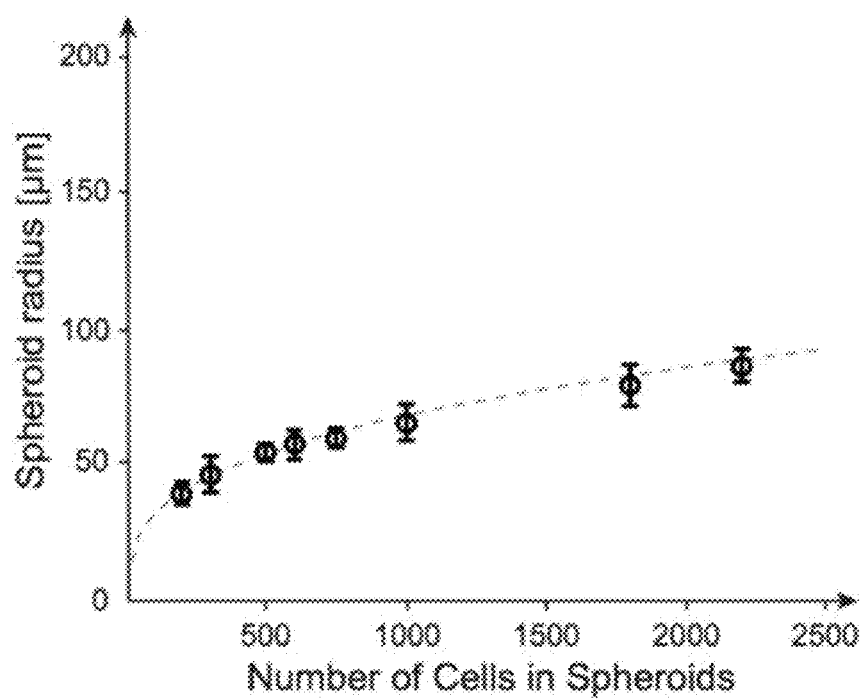
FIG. 33 shows how microtissue size is a function of the number of cells in the microtissue. The invention provides two mechanisms to control the number of cells in each microtissue; either by changing the size of alginate wells or by changing the seeding cell density. Utilizing both, microtissues with 200, 300, 500, 600, 750, 1000, 1800, and 2200 cells were obtained. The radius of the resulting, fully-aggregated microtissues after 3 days follows the expected equation $r_{spheroid} = (6/\pi \; v_{cell} \; n_{cell})^{1/3}/2$.

The reproducibility of the method in controlling the size of the pre-vascularized microtissue was characterized. By varying the microwell sizes and the co-culture ratios of cell types (FIG. 3b), the number of cells that could aggregate into a single microtissue was controlled. For example, microwells of three different sizes (100, 200, and 400 µm diameter) yielded microtissues of three different sizes (39±3 µm, 71±5 µm, and 82±7 µm diameter, respectively, all at the same cell-seeding concentration) (FIG. 27b). The well size was chosen to be large enough to hold all the cells at the initial seeding concentration, but small enough to ensure sufficient cell-cell contact to form a single microtissue rather than multiple microtissues. The cells aggregated into compact microtissues within the first two days of in vitro culture, as seen by the decreasing radius of the smallest circle to include all cells (FIG. 27c), with the main contraction happening in the first day and no further contraction after three days. It was also observed that the size of the fully contracted microtissues (at day 2 and after) correlated to the number of cells in the microtissue as expected; the diameter of the microtissues' cross sections related to the number of cells in the microtissue and the cells typical volume as rspheroid= $(6/\pi \ v_{cell} \ n_{cell})1/3/2$ (FIG. 33).

Figure 27D:
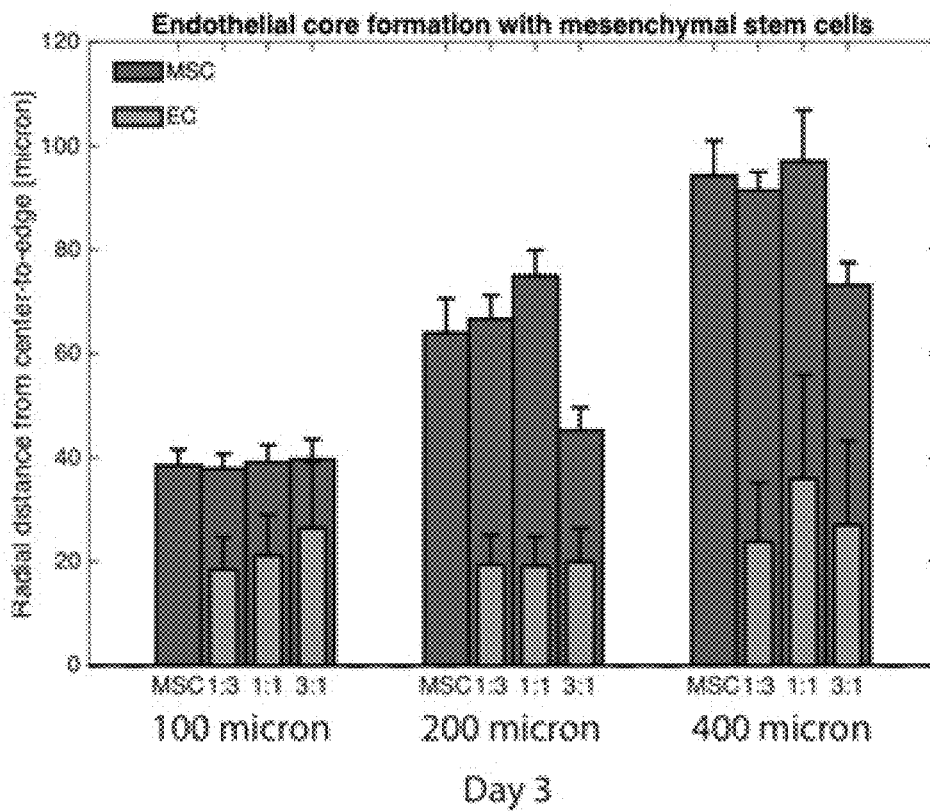
Figure 27E:
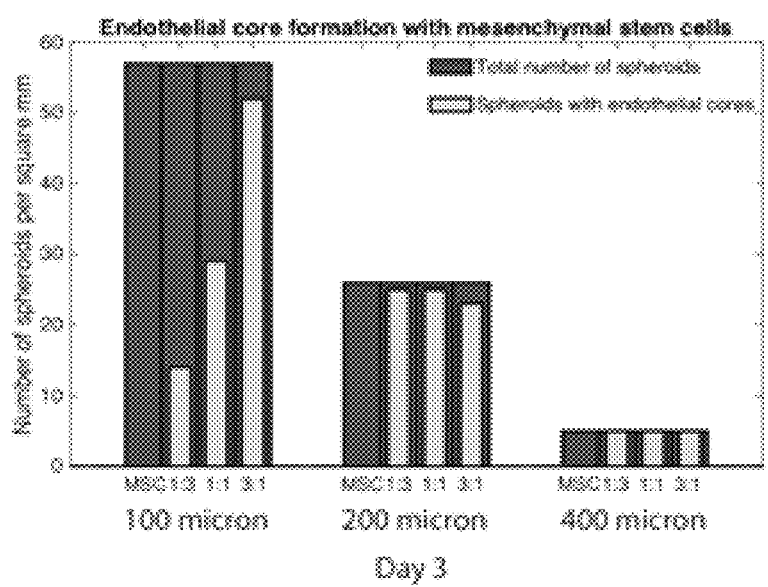
FIG. 27E shows reproducibility of endothelial cores; the number of microtissues produced in 1 mm$^2$ (dark grey) and the number of microtissues containing and endothelial core (light grey) for all tested microwell sizes and co-culture ratios.
Figure 34:
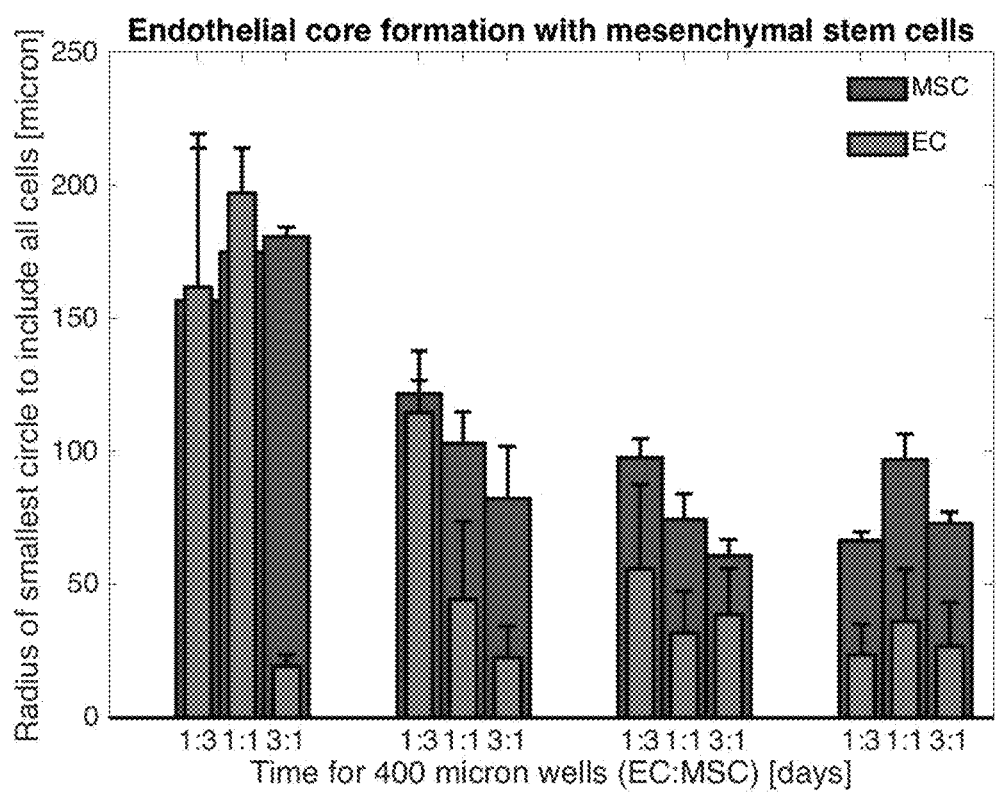
FIG. 34 illustrates microtissue contraction and endothelial core formation in 400-micron microwells from day 0 to day 3.
Figure 35:
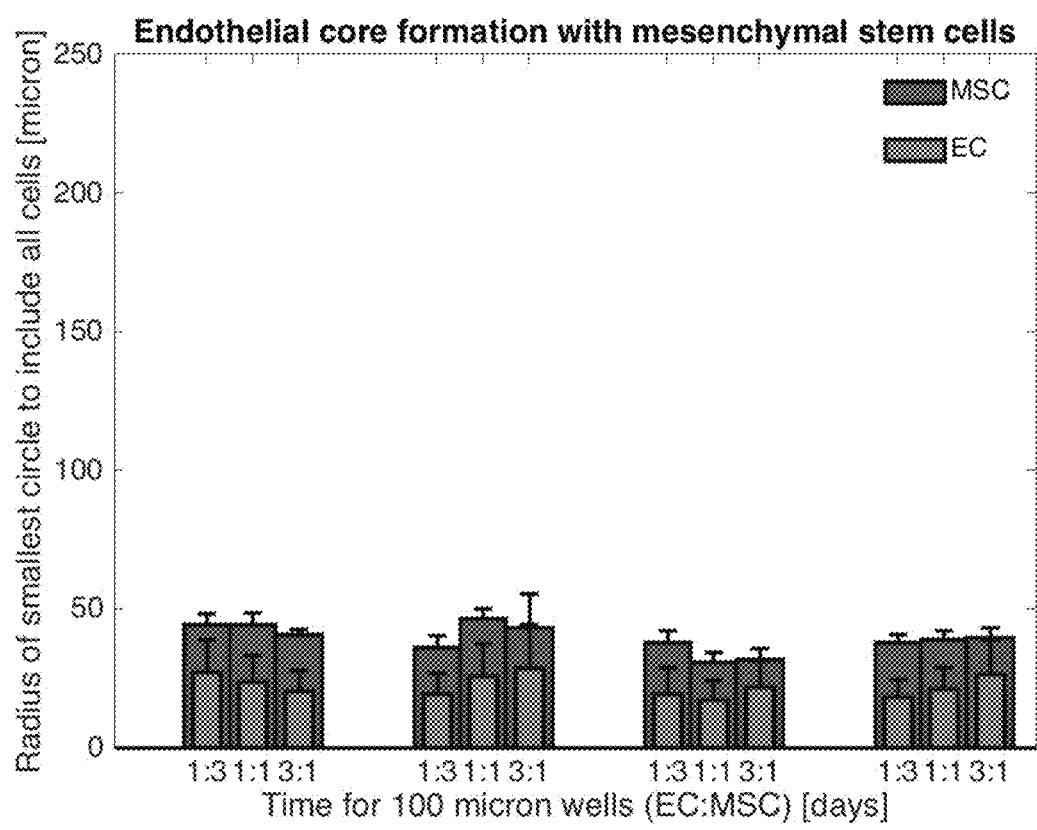
FIG. 35 illustrates microtissue contraction and endothelial core formation in 100-micron microwells from day 0 to day 3.

Also, the formation of microtissues was quantitatively analyzed for cultures containing only MSCs, and co-cultures with EC:MSC ratios of 1:3, 1:1, and 3:1 (FIG. 27 b-e). In 200-µm microwells, over three days, cells contracted into a microtissue and ECs migrated towards the center (FIG. 27c), and co-cultures in 400 µm microwells showed similar trends in microtissue contraction and EC migration (FIG. 34). Co-cultures in 100-µm microwells, however, did not contain enough cells (fewer than 150 cells in total) to form a distinct center (FIG. 35). It was also observed that the microtissues per unit area and the number of microtissues containing defined internal architectures could be controlled by varying microwell sizes and ratios of cell types (FIG. 27e). (In subsequent in vivo studies, 200-µm microwells were used with ratios of MSC only, 1 EC:3 MSC and 1 EC:1 MSC, as these conditions showed aggregation involving almost all the cells within the microwells.) Overall, the data showed the method can produce microtissues with internal architectures at high throughput and different sizes controllably.

EXAMPLE

Production of Pre-Vascularized Microtissues with Human Cells

Figures 28B, 28C:
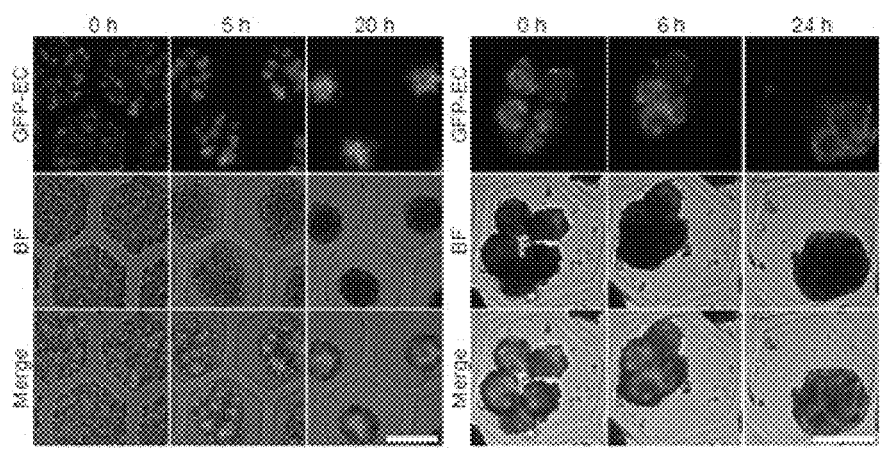
Figure 31A:
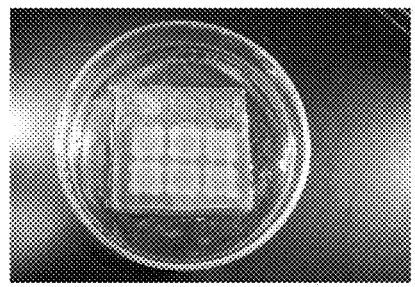
FIGS. 31A-31F show fabrication of alginate-based microwells.
Figure 31B:
Figure 31C:
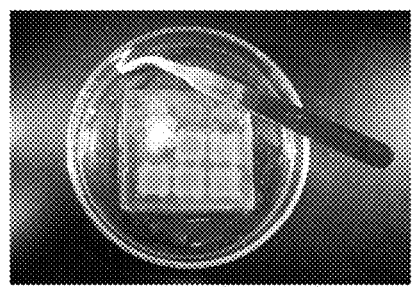
Figure 31D:
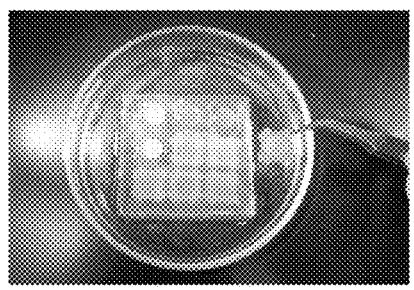
Figure 31E:
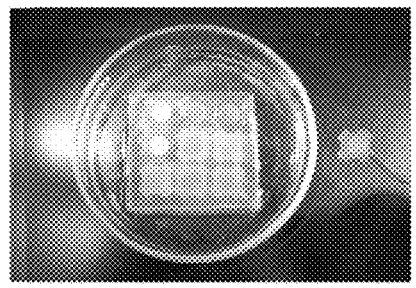
Figure 31F:
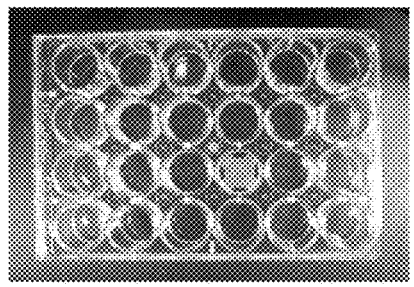
Figures 36A, 36B, 36C:
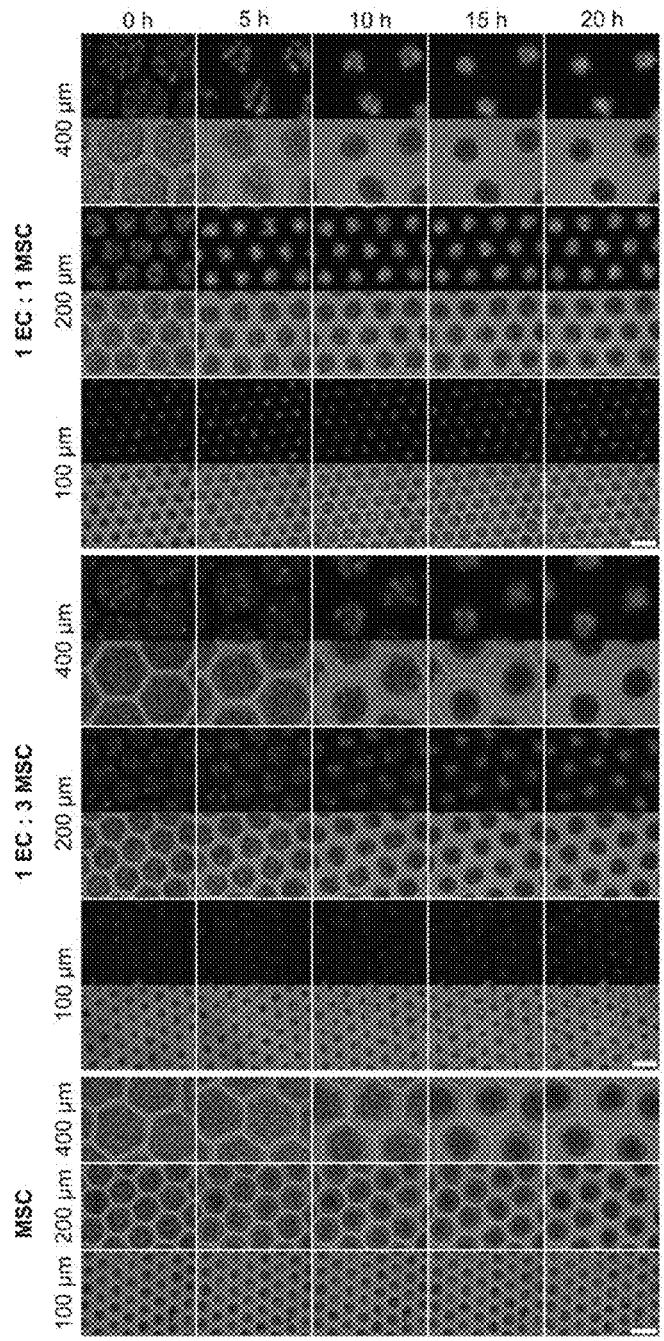
FIGS. 36A-36C illustrate the initial phase of microtissue formation and self-sorting. Shown are the first 20 hours of self-assembly and self-sorting immediately after seeding GFP-HUVEC and hAMSC cell mixtures in alginate microwells (100, 200, 400 μm). Fluorescent and brightfield images were acquired with a 10× objective. Scale bars are 200 μm.
Figure 37:
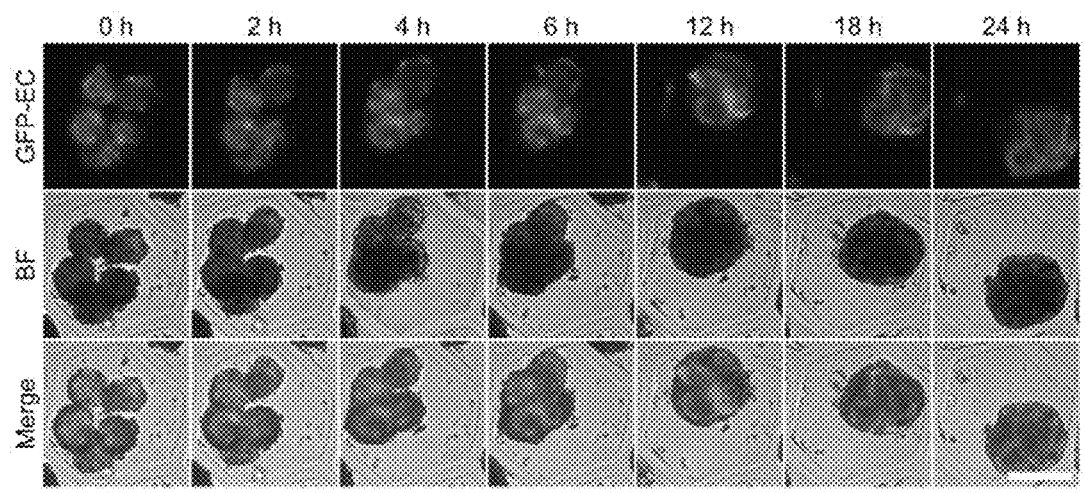
FIG. 37 illustrates microtissue fusion to form macrotissue. Microtissues were created in 200 μm sized microwells at 1:1 and 1:3 GFP-HUVEC to hAMSC ratio. Microtissues were cultured for 3 days in maintenance medium and 6 days in a vasculogenic medium to induce prevascularization (as seen at 0 h). For this assay the same vasculogenic medium was used. Prevascularized microtissues were placed in a collagen-alginate microwell. GFP fluorescence and brightfield images were acquired with a 10× objective in time-lapse microscopy over 24 h. Scale bar is 200 μm.

The effectiveness of this method was examined for producing pre-vascularized microtissues containing human adipose-derived MSCs (hAMSCs) with human umbilical vein endothelial cells (HUVECs), in ratios of MSCs only, 1 EC:3 MSC, and 1 EC:1 MSC. The maturation of microtissues was examined over 8 days, where microtissues were first grown in maintenance medium over 3 days to form endothelial cores, and then switched to vasculogenic medium containing exogenous growth factors for 5 days (FIG. 28a). By day 8, vessel-like structures spread through the entirety of the co-cultured microtissue (especially evident in the larger microtissues of the 400-µm wells). The initial migration of ECs was apparent after 20 hours (FIG. 28b and FIG. 36). In addition, we placed multiple pre-vascularized microtissues inside 400 µm alginate wells that were collagen-doped, to mimic the adhesiveness of native tissues. Within 24 hours, microtissues attached to each other and contracted to form a larger, compact mesotissue (aggregation of multiple microtissues) with a smooth outer border (FIG. 28c, with additional time points in FIG. 37). Hence, this method produced microtissues containing human ECs and MSCs, with control over sizes and spatial architectures, and confirming the ability to form a pre-vascularized mesotissue.

EXAMPLE

Figure 39A:
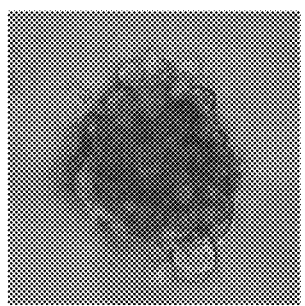
FIGS. 39A-39C show robustness to shear stress. Images are shown of microtissues before (FIG. 39A) and after injection through a 27 gauge needle (FIG. 39B) and a 30 gauge needle (FIG. 39C). Scale bar is 50 μm.
Figure 39B:
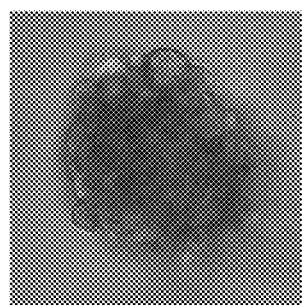
Figure 39C:
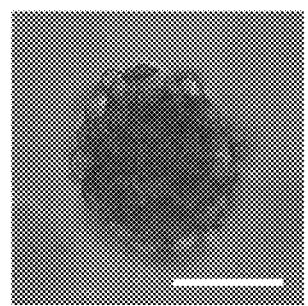
Figure 40A:
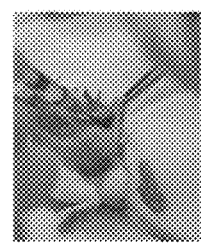
Figure 40B:
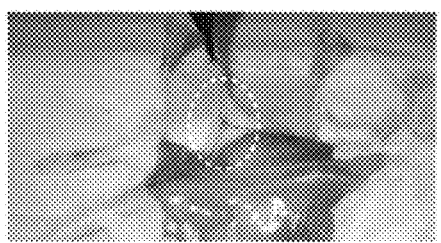
Figure 40C:
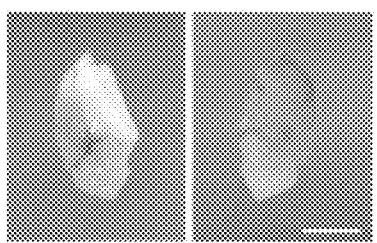
Figure 41A:
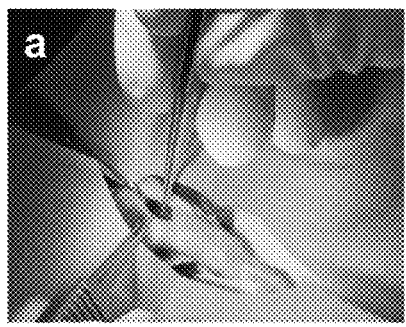
FIGS. 41A-41C illustrate surgical steps for modified induced hindlimb ischemia mouse model.
Figure 41B:
Figure 41C:
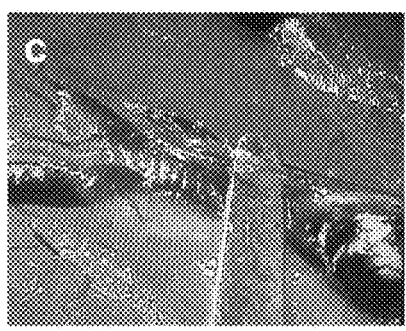
Figure 41D:
FIG. 41D shows how sutures were inserted under the femoral artery and tied off (picture shows the first tie).
Figure 41E:
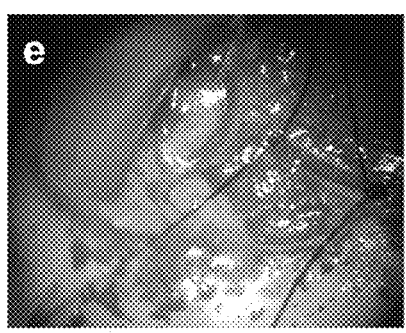
FIG. 41E shows how the femoral artery was doubly ligated and excised in its entirety.
Figure 41F:
FIG. 41F shows how the incision was closed.

Rapid Host Perfusion of Pre-Vascularized Microtissues of Human Cells in Animal Model Effectiveness of the prevascularized microtissues to self-organize to form a vascular network, anastomose to native host vasculature, and be perfused with host blood in a mouse model was assessed (FIG. 29a). To facilitate real-time visualization, we performed surgery to place a window chamber (FIG. 38) to permit brightfield, epifluorescence and confocal imaging. We used microtissues formed in 200-μm wells yielding microtissues approximately 70 μm in diameter, which is also within the diffusion limit of oxygen. Pre-vascularized spheroids made of human cells (HUVECs and hAMSCs) were produced and harvested, and were injected into SCID mice, a well-established animal model for studying integration of xenografts made of human cells. The vascular formation could be injected and monitored for multiple different conditions (e.g. 1 HUVEC:1 hAMSC and hAMSC only) in the same mouse, by utilizing the strong bond between the fascia and the subdermis. We injected the microtissues through the fascia and into the space between the fascia and the subdermis, leaving the subcutaneous tissue intact between injection sites to create a barrier (FIG. 29b). The microtissues held up intact to the shear stress of injection through a syringe and needle (FIG. 39). Interestingly, the shell of MSCs shielded the central blood-vessel building block against shear, and preserved the microtissues' architectural integrity after they passed through the needle. It was also demonstrated that the microtissues could be injected directly into adipose tissue (FIG. 40) and muscle tissue (FIG. 30) with good integration.

Formation of new vasculature was followed by taking epiflourescent and stereoscopic images through the window chamber. Stereoscopic imaging (for example, of the 1 HUVEC:1 hAMSC conditions) showed vessel formation between day 4 and 7 (FIG. 29b, top rows), with the implanted vasculature connected to the host vasculature and becoming perfused (FIG. 29b, top rows). After just 7 days, host perfusion of the implanted vasculature was prominent and intense. The vessels were functional for the remaining 16 days of the 23-day in vivo studies. Quantitatively, we measured the total length of perfused vasculature in three regions-of-interest (ROIs) within the area of injected microtissues (FIG. 29c). At day 7, areas injected with pre-vascularized microtissues showed significant formation of new perfused vasculature, while areas injected with microtissues consisting of MSCs only showed no increase in perfused vasculature (FIGS. 29b bottom row and 29c). For all four mice tested (each with multiple conditions in the window chamber), all conditions with EC-containing microtissues showed rapid vascularization of the injected microtissues.

It was also explored whether this self-organizing, "micro-to-macro" strategy could provide a limited but reproducible level of architectural control in the overall branching length of implanted, perfused microvasculature. It was hypothesized that average distances between endothelial cores could be related to diameters of microtissues. The mean length of the perfused branches for 1 EC:1 MSC at day 7 was 93±39 μm, with minimal changes by day 9 to 11, when the mean branch length was 86±29 μm and 93±44 μm, respectively (FIG. 29d). Indeed, the length of the newly formed vasculature's branches reflected core-to-core distances between the densely packed, injected microtissues with diameters of 71±5 μm. By contrast, co-cultured microtissues with randomly distributed ECs had previously yielded non-uniform branching lengths.

Epiflourescence and confocal microscopy were also used to characterize the formation and integration of the new vasculature. Observing the GFP-labeled HUVECs through the window chamber (FIG. 29e), we noticed the endothelial cores connecting with each other over time: the ECs initially appeared as discrete cores (day 0), then sprouted toward neighboring cores (day 4), connected with the host vasculature and became perfused (day 7), and stabilized as the perfused vascular network matured (day 9, 12, and 23). Between days 4 and 7, the network matured to form lumens (FIG. 29e, red arrows). The lumenous structure of the newly-formed, perfused network on day 11 was further confirmed via confocal microscopy on day 11. Moreover, it was observed that areas indicating newly formed lumens (consisting of GFP-labelled HUVECs) co-localized with areas indicating host blood perfusion, further confirming that it was the newly-formed lumenous vasculature that was perfused, rather than angiogenesis from the host into the implanted tissue.

EXAMPLE

Rapid Re-Vascularization and Re-Perfusion in a Hindlimb Ischemia Mouse Model

The effectiveness of this approach to treat ischemic conditions which are manifested in PAD was assessed. We induced acute, severe hindlimb ischemia by high femoral ligation with complete excision of the superficial femoral artery in C57BL/6 mice (FIG. 30a and FIG. 41). This surgical model was chosen as it consistently achieved distal hindlimb tissue necrosis but was more reproducible and better represented chronic manifestations of atherosclerotic disease than more severe ischemia animal models, where all side branches were severed but which showed less reproducible symptoms. We visualized and measured the perfusion of blood vessels close to the planar surface of the paw using laser speckle contrast imaging (LSCI). Over a defined region, LSCI can image perfusion in microvasculature within 300 μm of the skin surface, and provide accurate relative measurements of velocity of blood flow. Complete excision of the superficial femoral artery in the right hindlimb induced severe ischemia and limited perfusion, as confirmed by LSCI (FIG. 30b, shown are days 1, 7, 9, and 14 post-ligation). In the untreated control group, the hindlimb recovered by approximately days 14 to 19 (FIGS. 30b and 30c), consistent with previous results for this femoral ligation model.

For the treatment group, microtissues were injected into the hindlimb at four sites (FIG. 30a), taking advantage of the robustness of the microtissues to shear stress (FIG. 39) and thereby obviating invasive surgery. The microtissues contained 2 million cells across the sites, in the range of previous studies. While mice in both the control and microtissues groups exhibited a similar level of depressed perfusion in the injured hindlimb two days post-ligation, mice injected with microtissues rapidly regained perfusion in the ischemic leg after 7 to 9 days (FIGS. 30b and 30c), a week quicker than the untreated control group.

Histological analysis of the gastrocnemius muscle from mice confirmed the ischemic limb of the control group displayed only few regenerating myofibers (FIG. 30d), at levels indistinguishable from that of naive limbs (FIG. 30e). Also, they showed signs of tissue necrosis, as indicated by a fragmented collection of short hypereosinophilic and swollen pale eosinophilic myofibers (FIG. 30d). By contrast, histological cross-sections from mice injected with microtissues showed centralized nuclei characteristic of regenerating myofibers (FIG. 30d), with significantly more regenerating fibers than those of naive hindlimbs and ischemic limb of control group (FIG. 30e). Moreover, cross striations, which are characteristic of viable myofibers, were also more apparent in the hindlimbs of mice treated with microtissues compared to control group (FIG. 30e). The mice treated with injections of prevascularized microtissues regained perfusion of the ischemic limb in just 9 days, had more viable myofibers and exhibited significantly more regenerating myofibers.

This method of producing microtissues has practical advantages: high-throughput production and gentle harvesting. Previously, modest throughput, high labor intensiveness or harshness of handling have limited the practical impact of methods for producing microtissues. For example, automated methods based on hanging drops have been developed, but the scalability is limited by the number of wells. By comparison, the smallest construct shown in FIG. 2 produces 24,000 microtissues in a 24 well-plate, compared to 384 microtissues in the same area using conventional approaches. Also, there are fewer steps needed, both during the engineering of the microtissues (e.g. fewer and easier media-changing steps than hanging-drop methods) and their harvesting (e.g. one simple step of dissolving the alginate microwells which could be automated by conventional liquid handling). The use of alginate also contrasts with use of materials (such as PDMS) that adsorb steroid hormones and drugs, thereby enabling diverse culture conditions and downstream assays. Because this method is scaffold-independent, it opens up the method to producing microtissues and co-cultures of many different cell types and combinations that can mimic different tissues or in vivo interactions. For example, microtissues could provide a scaffold-independent alternative approach to current approaches for 3D printing of organs (such as bio-ink and cell-laden hydrogels), which will require a large scale of cellular and tissue components. A more detailed comparison of the current approach with other approaches is shown in FIG. 42. This method can be readily scaled beyond the quarter billion cells demonstrated in this study, to a degree which will be sufficient for a broad range of studies including developmental biology, cancer cell intravasation, drug screening, organ printing, and in vivo cell therapy.

Microtissue self-organization as a concept for clinical use. This method for producing injectable prevascularized microtissues could be used for tissue engineering and cell therapy. For tissue engineering, we demonstrated the microtissues can be reliably formed with controlled sizes and spatial architectures, and can self-organize into a macrotissue in which elements of the final architecture (such as branching lengths) of the new vascular network can also be controlled. For example, upon implantation into the host, blood-vessel networks formed between the microtissues, with integration and perfusion from host vasculature observed within 4 to 7 days, compared to several weeks typical of implanted materials or tissues which rely on host blood vessel invasion or connection. The vascular network forming from the endothelial cores exhibited characteristic branching lengths of 93±39 µm relating to the diameter of the microtissues, rather than chaotic microvascular networks. This level of reproducible self-organization suggests the potential of microtissues to act as self-assembling building blocks for other types of engineered tissues in the future.

For cell therapy, injection and printing with previously engineered unilaminar vascular microtissues have been challenging due to shear stress formation. Whenever possible, it would be advantageous in cell therapy to be able to deliver the cells via minimally invasive injection rather than invasive surgery. Our method produced microtissues which held up intact to shear stress during injections, even with high-gauge (25 to 30) needles (FIG. 39). This behavior may partially have been due to a shell of MSCs which protected the endothelial structure; interestingly, previous studies have also shown that the MSCs could act as an immune-suppressive shield for cell therapy in addition to providing angiogenic signaling.

Towards a novel treatment modality for ischemic conditions. To date, over 50 cell-therapy trials are at clinical stages for treating CLI. Many trials involve injecting isolated MSCs, but they have not yet shown significant new re-perfusion. A few approaches (such as MarrowStim) involve injecting isolated ECs, but the cells could die from deprivation of oxygen and nutrients before they are able to assemble into vascular networks in vivo. After injection of microtissues, the rapid revascularization and reperfusion observed in the mouse hindlimb ischemia model, as well as reduction of necrosis, point to the promise of a potentially new therapeutic approach for treating ischemic conditions. In a clinical scenario, such an approach could be especially attractive for "no-option" patients on the verge of amputation with subsequently poor mortality outcomes. Beyond CLI, this treatment could be extended to treat other types of ischemic conditions, including microvascular conditions such as wound ulcers, in either an injectable format or wound dressing. Before it can be tested clinically, more work will have to be done to tailor dosages and study long-term preclinical outcomes. This technique could also serve as a platform for delivery of other types of stem cells or tissues.

EXAMPLE

Fabrication of Alginate Microwells

An experimental setup was developed to culture cellular microtissues with high throughput and without the labor-intensive hanging drop approach. The cells were seeded onto an alginate construct with between 379 and 30,000 microwells. The cells settle into these microwells, and as the alginate provides no adherence structure for the cells, the cells will adhere strongly to each other forming spherical cell aggregates over the initial 24 hours.

The alginate microwells are cast on hydrophilic PDMS molds. Master molds were fabricated in SU-8 (SU-8 3050, Microchem, Newton, Mass.) on 3-inch Si wafers (Silicon Sense, Nashua, N.H.) by photolithography as described before 66 to cast polydimethylsiloxane (PDMS, Sylgard 184, Essex Brownell, Fort Wayne, Ind.) replicas from the masters. The PDMS molds were then made hydrophilic by plasma treatment, and submerged them in distilled water to retain their hydrophilicity. The PDMS molds were then autoclaved prior to casting alginate.

A 2% w/v alginate (Pronova UltraPure MVG, NovaMatrix, Drammen, Norway) was then prepared and autoclaved in HEPES saline buffer solution (Ultrasaline A, Lonza, Basel, Switzerland). The alginate was pipetted into the PDMS molds. Positive-displacement pipettes were used for accurate pipetting of viscous alginate solutions and to avoid bubbles. The top of the molds were closed with cellulose dialysis membranes (6000 Da MWCO), and the membranes were flattened using the edge of a sterile glass slide. A 60 mM $CaCl_2$ HEPES buffer solution was pipetted on top of the membrane for at least 60 min to crosslink the alginate at room temperature. The hydrogels were removed from the molds using sterilized tools, and the hydrogels placed in HEPES saline buffer solution (Ultrasaline A, Lonza, Basel, Switzerland) supplemented with 1.8 mM $CaCl_2$ (to prevent leaching of the calcium ions from the hydrogels). The alginate hydrogels were then transferred into sterile culture ware, such as 24-well plates (Fisher Scientific, Fair Lawn, N.J.) with the open micro wells facing up and stored them at 4° C. until further use.

EXAMPLE

Cell Sources

GFP-labeled human umbilical vein endothelial cells (GFP-hUVECs) (Angioproteomie, MA, USA) were cultured in Endothelial Growth Medium 2 (PromoCell, Heidelberg, Germany). Adipose derived human mesenchymal stem cells (hAMSCs) (Promocell, Heidelberg, Germany) were cultured in Mesenchymal Stem Cell Growth Medium (Promocell, Heidelberg, Germany). GFP expressing mouse endothelial cells (GFP-mECs) (Cell Biologics, IL, USA) were cultured in Complete Mouse Endothelial Cell Media (Cell Biologics, IL, USA). RFP-labeled mouse mesenchymal stem cells (RFP-mMSCs) (Cyagen, CA, USA) were cultured in DMEM with 10% FBS and 1% PenStrep (all from LifeTechnologies). All cells were gently passaged at 80-90% confluency using TrypLE (LifeTechnologies) and used only until passage P6 and mMSC until P8. Cells were cultured in 37° C. and 5% CO2-balanced, humidified atmosphere.

EXAMPLE

Fabrication of Microtissues

HUVECs and MSCs were harvested from 2D cell culture, counted and desired cell ratios of HUVECs to MSCs were prepared: MSC only, 1 HUVEC to 3 MSC, 1 HUVEC to 1 MSC and 3 HUVEC to 1 MSC.

Then the 1.8 mM $CaCl_2$ solution that the alginate microwells were stored in was removed, and replaced with DMEM (ATCC, Manassas, Va.). The microwells were then placed in the incubator at 37° C. and 5% $CO_2$ to equilibrate for at least 20 minutes. Then DMEM was removed and the microwell constructs gently dried using surgical spears (Braintree Scientific, Braintree, Mass.) leaving the microwell features covered. Cell suspensions were then pipetted on to alginate molds of 100, 200 and 400 μm microwell size using a positive displacement pipette. Cells were left to settle to the bottom of the microwells for 20 minutes and the culture wells were then filled up with culture medium.

EXAMPLE

Microtissue Media

The first 3-4 days after seeding, the cells were cultured in maintenance medium: Dulbecco's Modified Eagle Medium (DMEM) with 10% Fetal Bovine Serum (FBS) and 1% PenStrep (all from LifeTechnologies), with 50 μg/mL Sodium L-ascorbate (Sigma-Aldrich). For FIG. 28 and FIG. 29, the maintenance medium also included 20 mM Hepes (Fisher Scientific, Fair Lawn, N.J.), 1 μM Insulin (LifeTechnologies, Carlsbad, Calif.), 250 nM T3, 1 μM dexamethasone, 0.5 mM IBMX, 50 μM Indomethacine, 1 μM Rosiglitazone and 1 μM CL316243 (all from Sigma, St. Louis, Mo.). After the first 3-4 days, the media was changed from maintenance medium to vasculogenic medium: Dulbecco's Modified Eagle Medium (DMEM) with 10% Fetal Bovine Serum (FBS) and 1% PenStrep (all from LifeTechnologies), with 50 μg/mL Sodium L-ascorbate (Sigma-Aldrich), 40 ng/mL bFGF and 40 ng/mL VEGF recombinant human protein (both from LifeTechnologies). For FIG. 28 and FIG. 25, the vasculogenic media also included 20 mM Hepes, 1 μM Insulin, and 250 nM T3. The microtissues were cultured in vasculogenic medium up to day 11. Microtissue media was changed every other day.

EXAMPLE

Microtissue Collection

To collect microtissues, the alginate hydrogel was uncrosslinked 65. For this, the culture medium of the microtissues was replaced with 5% w/v sodium citrate solution for approximately 20 min. This chelator liquefied the alginate, and allowed for resuspension of the microtissues in a desired medium. Microtissues were then centrifuged at 300 rpm for 5 minutes or as specified and the microtissue pellet carefully collected for further use.

EXAMPLE

Microtissue Fusion

To test the ability of microtissues to assemble in vitro and fuse to a larger tissue, 200 μm sized microtissues of only hAMSCs, 1 EC:3 hAMSC and 1 EC:1 hAMSC ratio were placed in a 400 μm sized microwell of collagen-doped alginate composed of 3.5% collagen and 1% alginate. These microtissues had previously been prevascularized as described above. Microtissue fusion was conducted in vasculogenic medium and observed for 24 hours.

EXAMPLE

Formation of Microtissue

To yield a large enough number of microtissues in parallel to produce a macroscopic tissue, a co-culture of 1 MSC:1 EC ratio was seeded onto an alginate microwell construct that fits into a 60 mm culture dish and produces over 30,000 microtissues (FIGS. 26a and c). The cells were cultured in maintenance medium without growth factors for 4 days with daily media change due to the high number of cells. The microtissues were collected by removing the medium and uncrosslinking the alginate with 5 mL 5% w/v sodium citrate solution. The alginate liquefied and the microtissue solution was gently collected, spun down and resuspended in 1 mL vasculogenic media. To facilitate sustained culture and imaging of the macro-tissue, we had constructed a 1 $cm^2$ cylindrical hole in a 1 cm thick 10% agarose layer in the middle of a 60 mm dish. The hole was made by placing a 1 $cm^2$ by 1 cm PDMS mold in the middle, pouring on agarose and removing the PDMS cylinder when the agarose had gelled. The 1 mL microtissue suspension was pipetted into the hole, allowed to settle for 1 hour, and then had 5 mL vasculogenic media added on top. The media was changed daily.

EXAMPLE

Window Chamber Surgery

Window chamber surgeries were conducted as described previously. Briefly, a titanium window chamber (APJ Trading, Ventura, Calif.) was surgically implanted midline on the dorsum of male SCID mice (strain: ICRSC-M-M, 5-6 weeks of age, Taconic, Hudson, N.Y.) after hair removal and ethanol and iodine disinfection. To reduce variability between mice, prevascularized and non-prevascularized microtissues were implanted in individual compartments of the same window chamber. Microtissues were delivered by injection and pipetting underneath the fascia of connective tissue to the subcutaneous adipose tissue. Window chambers were closed with a circular glass cover slip and a retaining ring (APJ Trading, Ventura, Calif.). A custom-made 3D printed window chamber backing was attached to reduce skin movement in the window chamber. In a subset of experiments, a custom-made ultem plastic 9 well array was screwed onto the front frame of the window chamber to allow for high throughput in vivo testing. Here, microtissues were placed into one of the 9 wells.

Animals were housed aseptically in frog cages to allow for enough clearance for the window chamber while still permitting easy access to standard laboratory chow (Irradiated globle rodent diet, Fisher Scientific, Fair Lawn, N.J.) and drinking water ad libitum. Follow up buprenorphine administration (0.1 mg/kg bodyweight) for pain management was given subcutaneously every 6-12 hours after surgery for the next 2 days post-OP. CO2 euthanasia and cervical dislocation were performed after 30 days or earlier if necessary.

The animal procedures were approved and carried out in accordance to local regulations and authorities. The surgeries were conducted in aseptic technique.

EXAMPLE

Hindlimb Ischemia Surgery

Hindlimb ischemia-inducing surgeries were conducted as described previously. Briefly, ischemia was induced in the right hindlimb of the mouse by a high femoral artery ligation and total excision of the superficial femoral artery in 20 week-old C57BL/6 mice (The Jackson Laboratory, Bar Harbor, Me.). Mice were anesthetized with isoflurane and maintained on a warmed surface. Intraperitoneal injection of buprenorphine, for analgesia, and ultrasaline, for increased hydration, were administered pre-operatively. Mice were positioned in dorsal recumbency with their hindlimbs externally rotated. Lidocaine, for local anesthesia, was administered subcutaneously at the shaven surgical site, which was subsequently sterilized with ethanol and iodine. A skin incision was made over the femoral artery beginning at the inguinal ligament and continued caudally to the popliteal bifurcation. The femoral artery was isolated from the femoral vein and nerve bundle above the level of the profunda and epigastric branches, doubly ligated using 7-0 nylon suture and excised in its entirety. Prevascularized microtissues (corresponding to a total of $2 \times 10^6$ cells) or control medium at a volume of 0.1 mL were injected into the semimembranosus muscle at four sites along the thigh, immediately following femoral artery ligation and the incision was closed with 4-0 nylon suture. The prevascularized microtissues were made in 200 μm micro wells from a 1 RFP-mMSCs:1 GFP-mECs mix. Body temperature was maintained with heating pads until the animals recovered from surgery and were ambulatory. Animals were housed separately and closely monitored.

The animal procedures were approved and carried out in accordance to local regulations and authorities. The surgeries were conducted in aseptic technique.

EXAMPLE

Laser Speckle Contrast Imaging (LSCI) to Measure Perfusion

Laser speckle contrast imaging (LSCI) was used to measure perfusion of the ligated and naïve limbs on Day 0, 1, 2, 3, 5, 7, 9, 11 and 14 post surgery. A LSCI system was build and consisted of a 810 nm infrared laser diode, a beam expander and a CCD camera with a band-pass filter. The mice were briefly anesthetized with isoflurane and placed in sternal recumbency with the hindlimb stretched out behind them exposing the plantar surface of the hind paws. For each measurement, 40 consecutive images were obtained and the spatial speckle contrast was estimated from a 7×7 window of pixels. Average hind limb perfusion was determined for an anatomical defined region of the foot—the plantar surface of the hind paw spanning the digital, metacarpal and carpal pads. Calculated perfusion was expressed as a ratio of the mean perfusion of the planter surface of the right (ischemic) to the left (control) hind limb.

EXAMPLE

Histological Analysis

The animals were euthanized 14 days after femoral artery ligation. The bilateral gastrocnemius muscle from both hindlimbs were fixed, paraffin-embedded, cross-sectionally sliced and stained for H&E. The total number of myofibers were counted and the percentage distribution of regenerating (centralized nuclei), viable (striated) and necrotic (broken swollen pale hyalinized) myofibers were calculated for at least three ROI.

EXAMPLE

Imaging

A Leica DMI 6000B inverted microscope with 4× and 10× objectives, equipped with a motorized stage (Leica Microsystems, Bannockburn, Ill.) and a QImaging Retiga 2000R monochrome camera (QImaging, Surrey BC, Canada) was used to acquire fluorescence and brightfield images. Leica LAS X software was used for image acquisition. Cropping, color adjustments and contrast enhancements of images as well as Z-stack projections were performed in ImageJ. For time lapse imaging of microtissue formation and microtissue fusion an environmental chamber was used to maintain 37° C. and 5% $CO_2$. Images were acquired every 30 min. Confocal images of the window chamber were taken using a Leica SP5 confocal system with a 10.0×0.30 N.A. objective. To be able to image the window chamber mice were anesthetized with isoflurane. Due to the stressfulness of the anesthesia of the imaging procedure, in vivo images were acquired every 2-3 days.

To precisely observe individual microtissues, we took stacks of confocal images (1024×1024 pixels, 41 images with a z-spacing of 0.25 microns) using a Leica SP5 confocal microscope, with a 100×1.43 N.A. oil immersion objective (Leica Microsystems) at a resolution of 0.132 μm/pixel (image stacks were thus 135 mm*135 mm*10 mm). The differential interference contrast (DIC) images were simultaneously collected, as well as the RFP- and GFP-signal.

EXAMPLE

Assembling Microtissues In Vitro

The media was gently removed from the microwells. The alginate microwells were uncrosslinked with 200 µl of 5% sodium citrate, releasing the fully-formed microtissues into suspension. The suspension was gently spun down at 220 g for 5 minutes. The supernatant was removed and the microtissues resuspended in 0.5 ml vasculogenic media (DMEM with 10% fetal bovine serum (FBS), 1% PenStrep, 20 ng/mL ascorbic acid, 20 ng/mL vascular endothelial growth factor (VEGF) and 20 ng/mL basic fibroblast growth factor (bFGF). The microtissues were then spun down again at 220 g for 10 minutes and left in the incubator for an hour to form primary cell-cell adhesions between the microtissues to form macroscopic aggregates. The aggregates were gently tapped free of the tube bottom and the whole tube content (tissue-aggregate and vasculogenic media) was up-ended and transferred into an imaging well. The tissue-aggregates were cultured for an additional 10 days in vitro with a vasculogenic media change every other day.

EXAMPLE

Window Chamber Surgery

Microtissues were collected as described above. The suspension was gently spun down at 220 g for 5 minutes. The supernatant was removed and the microtissues resuspended in 200 µl PBS. In vitro created, prevascularized and non-prevascularized microtissues were implanted in a window chamber to allow for continuous in vivo monitoring of the vascularization and integration process.

All tools, surgical instruments and window chambers were autoclaved. Surgical procedures were done in a laminar flow hood in aseptic technique to reduce risk of contamination and infection. Surgeons were wearing an apron (Kimberly-Clark isolation gown, Fisher Scientific, Fair Lawn, N.J.), a hair net (Fisherbrand bouffant caps, Fisher Scientific, Fair Lawn, N.J.), and a surgical facemask (Kimberly-Clark classic surgical facemask, Fisher Scientific, Fair Lawn, N.J.). Because mice can loose a significant amount of body temperature during surgery, a 42° C. warm water heating pad (heated hard pad, Gaymar warm water pump, both from Braintree Scientific, Braintree, Mass.) was used.

Animal cages were disinfected with MB10 (Quip Laboratories) and opened in a laminar flow hood. Bodyweight was measured. For anesthesia Ketamine/Xylazine was injected intraperitoneally using a concentration of 80-100 mg/kg ketamine and 5-10 mg/kg xylazine (both from Butler Schein, Melville, N.Y.). For maintenance of anesthesia an additional dose of 30% of the original dose of ketamine was given. To monitor the depth of anesthesia toes were pinched every 5 minutes. The mouse eyes were covered with eye gel (Fisher Scientific, Fair Lawn, N.J.) to avoid damage. Hair removal at the surgical site was then done with an electrical animal hair trimmer (Braintree Scientific, Braintree, Mass.). The mouse was then placed on an animal restraint plate (Small animal surgery board, Braintree, Scientific, Braintree, Mass.). Sterile gloves (Fisher Scientific, Fair Lawn, N.J.) were put on. The surgical site on the mouse's dorsum was disinfected twice with scrubbing solution (Betadine surgical scrubbing solution, Fisher Scientific, Fair Lawn, N.J.) followed by cleaning with 70% ethanol. Then buprenorphine (between the scapulae, 0.1 mg/kg body weight) and lidocaine (at the surgical site, 5 mg/kg body weight) (both from Butler Schein, Melville, N.Y.) were injected subcutaneously. Mouse disinfection was then finished with the application of another round of scrubbing solution and ethanol and completed with application of prepping solution (Povidone iodine prepping solution, Fisher Scientific, Fair Lawn, N.J.) at the surgical site. Sterile gloves were changed and marked the completion of the animal preparation.

The mouse was placed parallel underneath the bar (custom made in lab) of the animal restraint plate. Three sutures (4.0 non-absorbable nylon suture, Fisher Scientific, Fair Lawn, N.J.) were placed to the front, middle and end of the back to spread out the skin of the dorsum and guided over the metal bar of the animal restraint plate. The middle suture was used as guidance to connect the backside of the window chamber (Window chamber kit, small, APJ Trading, Ventura, Calif.) to the skin. Sharp 18 G hypodermic needles (Fisher Scientific, Fair Lawn, N.J.) were inserted in blunt 15 G dispensing needles (McMaster-Carr, Atlanta, Ga.). The 18 G needles were used to penetrate the spread out skin where holes were needed for window chamber attachment and to push the blunt needles through the skin. Once holes were made, the 18 G needles were removed comparable to "mandrin techniques" and only the 15 G blunt needles were left in place. A piece of PDMS was used to facilitate the piercing of the skin (FIG. 38a). The light of a led lamp (Fisher Scientific, Fair Lawn, N.J.) was used to indicate the inner opening of the window chamber on the mouse and show major vessels under the skin. The shadow was encircled with a marking pen (Fisher Scientific, Fair Lawn, N.J.) and the skin area was then disinfected as mentioned above. Next a subcutaneous lidocaine injection at the surgical site followed. A new set of sterile gloves was put on. The circular marked skin was then cut out with surgical scissors and Adson tissue forceps (both from Fisher Scientific, Fair Lawn, N.J.) (FIG. 38b). Next the screws of the assembled front part of the window chamber were inserted into the blunt needles. Pushing together the front and back parts of the window chamber assembled it (FIG. 38c). Each screw was locked with a nut. All initial sutures were removed after secure window chamber frame placement. Next the site of implantation was prepared. The fascia of the subcutaneous tissue was carefully excised avoiding damage to the host tissue and vasculature. A magnifying camera and monitor were used to increase accuracy. Last remaining layers of fascia were lifted and prior collected microtissues were injected underneath. The window chamber was separated in up to 3 compartments (by leaving the fascia between injection sites undisturbed) and 3 different conditions were injected into separate compartments for simultaneous observation. To avoid air bubble entrapment in the window chamber, which could decrease imaging quality, the window chamber was filled up with Ultrasaline A (Lonza, Basel, Switzerland). The window chamber was closed by layering a glass slide on top and securing it with the retaining ring of the window chamber kit. A custom made, 3D printed holder was screwed on the window chamber and held in place with additional nuts (FIG. 38d) ensuring a tight seal of the window chamber to the skin. Sutures were placed in lateral holes of the window chamber frame to secure placement (FIG. 38e). As described above, to reduce variability between mice 3 conditions were injected into one window chamber. This concept of simultaneous implantation was extended and in a different set of experiments a 9 well ultem plastic array was milled, and inserted into the window chamber (FIG. 38f). This insert only changed the final steps of the window chamber protocol. Here, fascia was completely removed and microtissues were directly pipetted into one of the 9 wells of the insert.

In one or more first embodiments, an implantable microtissue comprises a spheroid. The spheroid may comprise a plurality of cells of a first cell type and a plurality of cells of a second cell type. The first cell type may be endothelial cells and can form a lumen in an interior region of the spheroid.

In the first embodiments or any other embodiment, the endothelial cells are vascular endothelial cells and the lumen forms a blood vessel unit.

In the first embodiments or any other embodiment, the endothelial cells are lymphatic endothelia cells and the lumen forms a lymph vessel unit.

In the first embodiments or any other embodiment, the first cell type is different from the second cell type.

In the first embodiments or any other embodiment, the second cell type is one of mesenchymal stem cells, smooth muscle cells, dermal fibroblasts, and adipose cells.

In the first embodiments or any other embodiment, the spheroid has a diameter less than 200 μm.

In the first embodiments or any other embodiment, the spheroid is constructed to be injected presumably in a solution with other spheroids.

In the first embodiments or any other embodiment, the lumen is formed at or near a center of the spheroid.

In one or more second embodiments, a method of forming microtissue for injection can comprise depositing cells of a first and second type into a microwell of a construct. The construct or surfaces of the microwell can comprise a material that is non-adherent with respect to the deposited cells. The method can further comprise, during a first time period, culturing the deposited cells in a culture media without one or more growth factors so as to form a spheroid. Optionally, the method can further comprise, during a second time period after the first time period, further culturing the spheroid with one or more growth factors to form the microtissue.

In the second embodiments or any other embodiment, the first time period is less than 4 days and the second time period is at least 6 days.

In the second embodiments or any other embodiment, the first cell type is endothelial cells and the second cell type is different than the first cell type.

In the second embodiments or any other embodiment, the second cell type is at least one of mesenchymal stem cells, smooth muscle cells, dermal fibroblasts, and adipose cells.

In the second embodiments or any other embodiment, the culturing during the first time period is such that a gradient of growth factor from the interior to the exterior of the spheroid is formed by the cells, and the endothelial cells migrate toward the center of the spheroid as a result of the gradient.

In the second embodiments or any other embodiment, the culturing during the first time period is such that a lumen is formed by the endothelial cells in an interior region of the spheroid.

In the second embodiments or any other embodiment, the culturing during the second time period is such that the endothelial cells sprout toward the exterior of the spheroid and mature into lumenous vessels.

In the second embodiments or any other embodiment, the method further comprises harvesting the microtissue from the construct.

In the second embodiments or any other embodiment, the harvesting comprises dissolving the construct and recovering the microtissue in solution.

In the second embodiments or any other embodiment, the construct is formed of alginate, agarose, or PDMS.

In the second embodiments or any other embodiment, the microwell has a diameter or cross-sectional width of less than 500 μm.

In the second embodiments or any other embodiment, the microwell has a diameter or cross-sectional width of 400 μm or less, of 200 μm or less, or of 100 μm or less.

In the second embodiments or any other embodiment, the one or more growth factors include one of vascular endothelial growth factor (VEGF) or basic fibroblast growth factor (bFGF).

In the second embodiments or any other embodiment, the culturing during the first time period is such that there is a non-homogeneous distribution of cells of the first and second type in the spheroid.

In the second embodiments or any other embodiment, the construct includes a plurality of microwells and the depositing and the culturing during the first and second time periods are performed for the plurality of microwells at the same time.

In the second embodiments or any other embodiment, the construct includes at least 1000 microwells.

In one or more third embodiments, a method of treating a patient can comprise forming a plurality of microtissues. Each microtissue can comprise a pre-vascularized spheroid. Each spheroid can comprise multiple cells with at least an endothelial cell core region. The method can further comprise injecting the plurality of microtissues into a patient such that a new vascular network is formed therein with the endothelial cell core regions of the spheroids as nodes.

In the third embodiments or any other embodiment, the new vascular network connects to the existing vasculature of the patient.

In the third embodiments or any other embodiment, the connection to the existing vasculature occurs within seven days after the injecting.

In the third embodiments or any other embodiment, the injecting is effective to treat a condition of ischemia.

In the third embodiments or any other embodiment, the injecting is performed at multiple locations spaced apart along a limb or other anatomical feature of the patient.

In the third embodiments or any other embodiment, the multiple cells comprise at least one of mesenchymal stem cells, smooth muscle cells, dermal fibroblasts, and adipose cells.

In this application, unless specifically stated otherwise, the use of the singular includes the plural and the use of "or" means "and/or." Furthermore, use of the terms "including" or "having," as well as other forms, such as "includes," "included," "has," or "had" is not limiting. Any range described herein will be understood to include the endpoints and all values between the endpoints. Moreover, any use of terms such as "near," "approximate," or the like, include the recited limitation as well as values within 10% of the recited limitation.

According to fourth embodiments, the disclosed subject matter includes a biological tissue product prepared by a process. the process includes co-culturing therapeutic and endothelial cells in a cluster in maintenance medium depleted in vasculogenic growth factors and for a period of time that together are effective to cause the endothelial cells to concentrate in respective central regions of the cluster. continuing the co-culturing for a period of time effective to cause the concentration of endothelial cells to form a lumen in the central region. integrating the cluster in a living host or combining with other like clusters to form a biological tissue in vitro.

In further fourth embodiments, the co-culturing is performed in a hydrogel well of an array of hydrogel wells. In further fourth embodiments, the process includes dissolving the hydrogel to release the cluster. In further fourth embodiments, the maintenance medium includes no vasculogenic growth factor. In further fourth embodiments, the integrating or combining includes exposing the cluster to vasculogenic growth factors. In further fourth embodiments, the integrating or combining includes exposing the cluster to vasculogenic growth factors. In further fourth embodiments, the exposing is effective to cause endothelial cells of the lumen to connect with external endothelial cells to form interconnecting vessels. In further fourth embodiments, the integrating includes injecting the cluster through a cannula into a living organism. In further fourth embodiments, the integrating or combining includes combining the cluster with other like clusters to form a biological tissue in vitro and further culturing a resulting combination. In further fourth embodiments, the further culturing includes exposing the resulting combination to a vasculogenic growth factor. In further fourth embodiments, the therapeutic cells include mesenchymal stem cells. In further fourth embodiments, the product cluster can be injected through a cannula without disintegration.

According to fifth embodiments, the disclosed subject matter includes a method for producing a biological tissue product. The method includes co-culturing therapeutic and endothelial cells in a cluster in maintenance medium depleted in vasculogenic growth factors and for a period of time that together are effective to cause the endothelial cells to concentrate in respective central regions of the cluster. The method further includes continuing the co-culturing for a period of time effective to cause the concentration of endothelial cells to form a lumen in the central region and integrating the cluster in a living host or combining with other like clusters to form a biological tissue in vitro.

In further fifth embodiments, the co-culturing is performed in a hydrogel well of an array of hydrogel wells. In further fifth embodiments, the process includes dissolving the hydrogel to release the cluster. In further fifth embodiments, the maintenance medium includes no vasculogenic growth factor. In further fifth embodiments, the integrating or combining includes exposing the cluster to vasculogenic growth factors. In further fifth embodiments, the integrating or combining includes exposing the cluster to vasculogenic growth factors. In further fifth embodiments, the exposing is effective to cause endothelial cells of the lumen to connect with external endothelial cells to form interconnecting vessels. In further fifth embodiments, the integrating includes injecting the cluster through a cannula into a living organism. In further fifth embodiments, the integrating or combining includes combining the cluster with other like clusters to form a biological tissue in vitro and further culturing a resulting combination. In further fifth embodiments, wherein the further culturing includes exposing the resulting combination to a vasculogenic growth factor. In further fifth embodiments, the therapeutic cells include mesenchymal stem cells. In further fifth embodiments, the product cluster can be injected through a cannula without disintegration.

According to sixth embodiments, the disclosed subject matter includes a method of forming microtissue for injection. The method includes depositing cells of a first and second type into a microwell of a construct, the construct or surfaces of the microwell including a material to which the deposited cells are non-adherent. During a first time period, the deposited cells are cultured in a culture media depleted in growth factors, the level of growth factors and length of the first time period being such that a spheroid with a concentration the endothelial cells is formed by the end of the first time period. During a second time period after the first time period, the spheroid is further cultured with one or more growth factors to form the microtissue. In further sixth embodiments, the first time period is less than 4 days and the second time period is at least 6 days. In further sixth embodiments, the first cell type is endothelial cells and the second cell type is different than the first cell type. In further sixth embodiments, the second cell type is at least one of mesenchymal stem cells, smooth muscle cells, dermal fibroblasts, and adipose cells. In further sixth embodiments, the culturing during the first time period is such that a gradient of growth factor from the interior to the exterior of the spheroid is formed by the cells, and the endothelial cells migrate toward the center of the spheroid as a result of the gradient. In further sixth embodiments, the culturing during the first time period is such that a lumen is formed by the endothelial cells in an interior region of the spheroid. In further sixth embodiments, the second time period is such that the endothelial cells sprout toward the exterior of the spheroid and mature into lumenous vessels. Further sixth embodiments include harvesting the microtissue from the construct. In further sixth embodiments, the harvesting comprises dissolving the construct and recovering the microtissue in solution. In further sixth embodiments, the construct is formed of alginate, agarose, or PDMS. In further sixth embodiments, the microwell has a diameter or cross-sectional width of less than 500 µm. In further sixth embodiments, the microwell has a diameter or cross-sectional width of 400 µm or less, of 200 µm or less, or of 100 µm or less. In further sixth embodiments, the one or more growth factors include one of vascular endothelial growth factor (VEGF) or basic fibroblast growth factor (bFGF). The method of claim 56, wherein the culturing during the first time period is such that there is a non-homogeneous distribution of cells of the first and second type in the spheroid. In further sixth embodiments, the construct includes a plurality of microwells and the depositing and the culturing during the first and second time periods are performed for the plurality of microwells at the same time. In further sixth embodiments, the construct includes at least 1000 microwells.

According to seventh embodiments, the disclosed subject matter includes a method of forming a biological tissue. The method includes co-culturing endothelial and therapeutic cells to form spheroids each with a size of less than 1000 microns to form a region concentrated in endothelial cells surrounded by a region depleted in endothelial cells. The method includes ex vivo, placing multiple spheroids resulting from the co-culturing in mutual contact under conditions and for a time that permits signaling between the regions concentrated in endothelial cells to form lumens between the spheroids to form a larger vascularized construct. According to seventh embodiments the placing for a time includes exposing the multiple spheroids to vasculogenic growth factors.

According to eighth embodiments, the disclosed subject matter includes an injectable microtissue. The microtissue includes a plurality of spheroids, each with a plurality of cells of a first cell type and a plurality of cells of a second cell type, the first cell type being endothelial cells that are concentrated in an interior region of the each spheroid. Each of the plurality of spheroids resides in a microwell formed in a soluble matrix and isolated from others of the plurality of spheroids.

In further eighth embodiments, the endothelial cells concentrated in an interior region define a lumen-shaped structure. In further eighth embodiments, the plurality of cells of the second type form a durable shell that can withstand the shear strain and stress of injection through a 27ga (0.27 mm) or 30ga (0.159 mm) cannula at rates of 0.1 to 2 mL/min. In further eighth embodiments, the endothelial cells are vascular endothelial cells and the lumen-shaped structure is a blood vessel precursor. In further eighth embodiments, the endothelial cells are lymphatic endothelial cells and the lumen-shaped structure forms a lymph vessel precursor. In further eighth embodiments, the second cell type is one of mesenchymal stem cells, smooth muscle cells, dermal fibroblasts, and adipose cells. In further eighth embodiments, the majority of the spheroids have diameters less than 200 µm. In further eighth embodiments, the spheroid have a structural integrity capable of withstanding the shear strain of injection through a cannula into a host without disintegration in a solution with other spheroids. In embodiments, the shear is that associated injection through a 27ga (0.27 mm) or 30ga (0.159 mm) cannula at rates of 0.1 to 2 mL/min In further eighth embodiments, the lumens are located at or near the center of a respective one of the plurality of spheroids. In further eighth embodiments, the soluble matrix includes a hydrogel. In further eighth embodiments, the soluble matrix includes alginate.

According to ninth embodiments, the disclosed subject matter includes an injectable microtissue including a plurality of spheroids, each having a plurality of cells of a first cell type and a plurality of cells of a second cell type. The first cell type is endothelial and they are concentrated in an interior region of the each spheroid. The spheroids have diameters of less than 200 µm.

In further ninth embodiments, the plurality of spheroids is free of vascular interconnections therebetween. In further ninth embodiments, the plurality of spheroids is suspended in an injectable blood-normal medicament. In further ninth embodiments, the endothelial cells concentrated in an interior region define a lumen-shaped structure. In further ninth embodiments, the plurality of cells of the second type form a durable shell that that can withstand the shear strain and stress of injection through a 27ga (0.27 mm) or 30ga (0.159 mm) cannula at rates of 0.1 to 2 mL/min In further ninth embodiments, the endothelial cells are vascular endothelial cells and the lumen-shaped structure is a blood vessel precursor. In further ninth embodiments, the endothelial cells are lymphatic endothelial cells and the lumen-shaped structure forms a lymph vessel precursor. In further ninth embodiments, the second cell type is one of mesenchymal stem cells, smooth muscle cells, dermal fibroblasts, and adipose cells. In further ninth embodiments, the majority of the spheroids have diameters less than 200 µm. In further ninth embodiments, the spheroid have a structural integrity capable of withstanding the shear strain and stress of injection through a 27ga (0.27 mm) or 30ga (0.159 mm) cannula at rates of 0.1 to 2 mL/min disintegration in a solution with other spheroids. The microtissue of claim 85, wherein the lumens are located at or near the center of a respective one of the plurality of spheroids.

According to tenth embodiment, the disclosed subject matter includes an array of microtissue spheroids. The array includes a plurality of spheroids, each comprising a plurality of cells of a first cell type and a plurality of cells of a second cell type, the first cell type being endothelial cells that are concentrated in an interior region of the each spheroid. Each of the plurality of spheroids being isolated from others in a respective well of an array of microwells in a substrate.

In further tenth embodiments, the endothelial cells concentrated in an interior region define a lumen-shaped structure. In further tenth embodiments, the plurality of cells of the second type form a durable shell that can withstand the shear strain and stress of injection through a 27ga (0.27 mm) or 30ga (0.159 mm) cannula at rates of 0.1 to 2 mL/min. In further tenth embodiments, the endothelial cells are vascular endothelial cells and the lumen-shaped structure is a blood vessel precursor. In further tenth embodiments, endothelial cells are lymphatic endothelial cells and the lumen-shaped structure forms a lymph vessel precursor. In further tenth embodiments, the second cell type is one of mesenchymal stem cells, smooth muscle cells, dermal fibroblasts, and adipose cells. In further tenth embodiments, the spheroids have diameters less than 200 µm. In further tenth embodiments, the spheroid have a structural integrity capable of withstanding the shear strain and stress of injection through a 27ga (0.27 mm) or 30ga (0.159 mm) cannula at rates of 0.1 to 2 mL/min without disintegration in a solution with other spheroids. In further tenth embodiments, the lumens are located at or near the center of a respective one of the plurality of spheroids.

According to eleventh embodiments, the disclosed subject matter includes an injectable microtissue. The microtissue includes a plurality of spheroids, each comprising a plurality of cells of a first cell type and a plurality of cells of a second cell type, the first cell type being endothelial cells that are concentrated in an interior region of the each spheroid. The spheroids having diameters of less than 200 µm and each being vascularly isolated including vascularly disconnected from the others of the spheroids and vascularly disconnected from an external host.

In further eleventh embodiments, the plurality of spheroids is free of vascular interconnections therebetween. In further eleventh embodiments, wherein the plurality of spheroids is suspended in an injectable blood-normal medicament. In further eleventh embodiments, the endothelial cells concentrated in an interior region define a lumen-shaped structure. In further eleventh embodiments, plurality of cells of the second type form a durable shell that can withstand the shear strain and stress of injection through a 27ga (0.27 mm) or 30ga (0.159 mm) cannula at rates of 0.1 to 2 mL/min In further eleventh embodiments, the endothelial cells are vascular endothelial cells and the lumen-shaped structure is a blood vessel precursor. In further eleventh embodiments, the endothelial cells are lymphatic endothelial cells and the lumen-shaped structure forms a lymph vessel precursor. In further eleventh embodiments, the second cell type is one of mesenchymal stem cells, smooth muscle cells, dermal fibroblasts, and adipose cells. In further eleventh embodiments, the majority of the spheroids have diameters less than 200 µm. In further eleventh embodiments, the spheroid have a structural integrity capable of withstanding the shear strain and stress of injection through a 27ga (0.27 mm) or 30ga (0.159 mm) cannula at rates of 0.1 to 2 mL/min without disintegration in a solution with other spheroids. The microtissue of claim 105, wherein the lumens are located at or near the center of a respective one of the plurality of spheroids.

According to twelfth embodiments, the disclosed subject matter includes a method of growing a tissue structure in a living host. The method includes co-culturing cells of multiple types in respective microwells, including controlling a composition of a nutrient medium such that the cells in each microwell organizes into a respective cluster responsively to growth factors, that naturally arise from the cells, into spheroids with a first cell type concentrated in the center and depleted at a periphery of the respective cluster. the co-culturing including culturing for a period of days. The method further includes releasing the clusters from the microwells and combining in a solution. injecting the solution, containing the clusters, into a living host.

In further twelfth embodiments, the releasing includes dissolving a matrix in which the microwells are formed. In further twelfth embodiments, the first cell type is endothelial. In further twelfth embodiments, the multiple types include stem type cells. In further twelfth embodiments, the multiple types include therapeutic cells. In further twelfth embodiments, the co-cultivating includes controlling a composition of a nutrient medium at a first time to include no vasculogenic growth factors and at a second time, controlling a composition of a nutrient medium to include vasculogenic growth factors, wherein the method includes exposing the clusters to the resulting mediums during the respective first and second times.

According to thirteenth embodiments, the disclosed subject matter includes a method of forming a tissue construct. The method includes creating multiple tissue clusters each with a mixture of endothelial and therapeutic cells organized such that when the tissue clusters are placed together in a culturing medium, the therapeutic cells separate from the endothelial cells, the latter being concentrated in respective nodes at the center of each cluster. The method further includes placing the tissue clusters together in a vasculogenic medium to induce the formation of vascular tissue connections between the endothelial cell nodes. The method further includes culturing for a time sufficient to generate vascular branches interconnecting a substantial number of the nodes, whereby a vascularized tissue construct is formed. The method further includes implanting the vascularized tissue construct in a living host.

In further thirteenth embodiments, the ratio of endothelial cells (EC) to therapeutic cells (TC), (EC:TC), is in the range of 1:1 through 1:2. In further thirteenth embodiments, the ratio of endothelial cells (EC) to therapeutic cells (TC), (EC:TC), is in the range of 1:1 through 1:3. In further thirteenth embodiments, the ratio of endothelial cells (EC) to therapeutic cells (TC), (EC:TC), is in the range of 1:1 through 2:3. In further thirteenth embodiments, the ratio of endothelial cells (EC) to therapeutic cells (TC), (EC:TC), is in the range of 1:2 through 2:1. In further thirteenth embodiments, the ratio of endothelial cells (EC) to therapeutic cells (TC), (EC:TC), is in the range of 2:3 through 3:1. In further thirteenth embodiments, the ratio of endothelial cells (EC) to therapeutic cells (TC), (EC:TC), is about 1:1. In further thirteenth embodiments, the ratio of endothelial cells (EC) to therapeutic cells (TC), (EC:TC), is about 1:2. In further thirteenth embodiments, the ratio of endothelial cells (EC) to therapeutic cells (TC), (EC:TC), is about 1:3.

According to fourteenth embodiments, the disclosed subject matter includes a method of forming a tissue construct. The method includes creating multiple tissue clusters each with a mixture of endothelial and therapeutic cells organized such that when the tissue clusters are placed together in a culturing medium, the therapeutic cells separate from the endothelial cells, the latter being concentrated in respective nodes at the center of each cluster. The method further includes the creating including culturing tissue clusters in a medium having a first concentration of vasculogenic growth factors for a first time and, after the first time, culturing the tissue clusters in a medium having a second concentration of vasculogenic growth factors for a second time, where the second concentration is greater than the first. The method further includes implanting or injecting the clusters in a living animal.

In further fourteenth embodiments, the ratio of endothelial cells (EC) to therapeutic cells (TC), (EC:TC), is in the range of 1:1 through 1:2. In further fourteenth embodiments, the ratio of endothelial cells (EC) to therapeutic cells (TC), (EC:TC), is in the range of 1:1 through 1:3. In further fourteenth embodiments, the ratio of endothelial cells (EC) to therapeutic cells (TC), (EC:TC), is in the range of 1:1 through 2:3. In further fourteenth embodiments, the ratio of endothelial cells (EC) to therapeutic cells (TC), (EC:TC), is in the range of 1:2 through 2:1. In further fourteenth embodiments, the ratio of endothelial cells (EC) to therapeutic cells (TC), (EC:TC), is in the range of 2:3 through 3:1. In further fourteenth embodiments, the ratio of endothelial cells (EC) to therapeutic cells (TC), (EC:TC), is about 1:1. In further fourteenth embodiments, the ratio of endothelial cells (EC) to therapeutic cells (TC), (EC:TC), is about 1:2. In further fourteenth embodiments, the ratio of endothelial cells (EC) to therapeutic cells (TC), (EC:TC), is about 1:3.

In any of the foregoing embodiments, the ratio of endothelial cells (EC) to therapeutic cells (TC), (EC:TC), may be in the range of 1:1 through 1:2.

In any of the foregoing embodiments, the ratio of endothelial cells (EC) to therapeutic cells (TC), (EC:TC), may be in the range of 1:1 through 1:3.

In any of the foregoing embodiments, the ratio of endothelial cells (EC) to therapeutic cells (TC), (EC:TC), may be in the range of 1:1 through 2:3.

In any of the foregoing embodiments, the ratio of endothelial cells (EC) to therapeutic cells (TC), (EC:TC), may be in the range of 1:2 through 2:1.

In any of the foregoing embodiments, the ratio of endothelial cells (EC) to therapeutic cells (TC), (EC:TC), may be in the range of 2:3 through 3:1.

In any of the foregoing embodiments, the ratio of endothelial cells (EC) to therapeutic cells (TC), (EC:TC), may be about 1:1.

In any of the foregoing embodiments, the ratio of endothelial cells (EC) to therapeutic cells (TC), (EC:TC), may be about 1:2.

In any of the foregoing embodiments, the ratio of endothelial cells (EC) to therapeutic cells (TC), (EC:TC), may be about 1:3.

In any of the foregoing embodiments, the therapeutic cells may include stem cells. In any of the foregoing method embodiments, the therapeutic cells may be cells selected responsively to a predefined disease or pathology of a host. In any of the foregoing methods in which spheroids or clusters (the terms being used interchangeably herein) are injected in a suspension thereof, the suspending fluid may include a buffered saline. In any of the foregoing methods in which spheroids or clusters (the terms being used interchangeably herein) are injected in a suspension thereof, the suspending fluid may include a phosphate-buffered saline.

According to fifteenth embodiments, the disclosed subject matter includes a method of creating a therapeutic tissue for injection. The method includes, in vitro, in 200 micron diameter or less wells, culturing endothelial cells and therapeutic cells forming cell clusters in a medium depleted in vasculogenic growth factor for a first period of time to induce a sorting of the endothelial cells in which the endothelial cells concentrate in a region near a center of the each cell cluster. The method further includes after the first period of time, further culturing in a medium with an increased concentration of vasculogenic growth factor for a second period of time to induce the formation of branching structures extending from the regions, the branching structures comprising the endothelial cells. The method further includes removing the clusters from the wells after at least the first period of time and adding the clusters to an injectable solution to form a suspension.

In further fifteenth embodiments, the solution is a buffered saline. Further fifteenth embodiments may include centrifuging or otherwise mechanically concentrating the clusters in a medium containing the clusters to produce a supernatant, the adding including adding the supernatant to the injectable solution. In further fifteenth embodiments, the removing the clusters from the wells after at least the first period of time is removing the clusters from the wells after the second period of time. In further fifteenth embodiments, the therapeutic cells include stem cells. In further fifteenth embodiments, the ratio of therapeutic cells to endothelial cells is greater than unity. In further fifteenth embodiments, the ratio of therapeutic cells to endothelial cells is greater than 1.5. In further fifteenth embodiments, the ratio of therapeutic cells to endothelial cells is greater than 2. In further fifteenth embodiments, the ratio of therapeutic cells to endothelial cells is 3. In further fifteenth embodiments, the first period of time is between 2 and 5 days. In further fifteenth embodiments, the sum of the first and second periods of time is less than 6 days. In further fifteenth embodiments, the sum of the first and second periods of time is less than 7 days. In further fifteenth embodiments, the sum of the first and second periods of time is less than 8 days. In further fifteenth embodiments, the sum of the first and second periods of time is between 6 and 12 days. In further fifteenth embodiments, the first time period is less than 4 days and the second time period is at least 6 days.

According to sixteenth embodiments, the disclosed subject matter includes a method of creating a therapeutic tissue for implantation. The method includes, in vitro and in 200 micron diameter or less wells, culturing endothelial cells and therapeutic cells forming cell clusters in a medium depleted in vasculogenic growth factor for a first period of time to induce a sorting of the endothelial cells in which the endothelial cells concentrate in a region near a center of the each cell cluster. After the first period of time, the cell clusters are further cultured in a medium with an increased concentration of vasculogenic growth factor for a second period of time to induce the formation of branching structures extending from the regions, the branching structures comprising the endothelial cells. The method further includes removing the clusters from the wells after at least the first period of time and combining the clusters and further culturing to cause fusion and vascular interconnection between the clusters prior to implantation in a living host.

Further sixteenth embodiments may include centrifuging or otherwise mechanically concentrating the clusters in a medium containing the clusters to produce a supernatant, the adding including adding the supernatant to a culture medium to perform the further culturing.

The removing the clusters from the wells after at least the first period of time may be removing the clusters from the wells after the second period of time. The therapeutic cells may include stem cells. The ratio of therapeutic cells to endothelial cells may be greater than unity.

The ratio of therapeutic cells to endothelial cells may be greater than 1.5.

The ratio of therapeutic cells to endothelial cells may be greater than 2.

The ratio of therapeutic cells to endothelial cells may be 3.

The first period of time may be between 2 and 5 days.

The sum of the first and second periods of time may be less than 6 days.

The sum of the first and second periods of time may be less than 7 days. The sum of the first and second periods of time may be less than 8 days. The sum of the first and second periods of time may be between 6 and 12 days. The first time period may be less than 4 days and the second time period, at least 6 days.

In further embodiments, the disclosed subject matter includes a method, microtissue, or product according to any of the method embodiments, including claims, where each includes all combinations or subcombinations of the limitations of their respective dependent claims not otherwise explicitly claimed.

In further embodiments, the disclosed subject matter includes a therapeutic method employing any of the products, microtissues, or methods (including the claims), in which the therapeutic cells are previously harvested from a host and then implanted and injected in the same host.

The foregoing descriptions apply, in some cases, to examples generated in a laboratory, but these examples may be extended to production methods. For example, where quantities and methods apply to the laboratory examples, they should not be understood as limiting. In addition, although specific chemicals and materials have been disclosed herein, other chemicals and materials may also be employed according to one or more contemplated embodiments.

Although in the embodiments, endothelial cells are combined with therapeutic cells, the cells chosen may have further functions and be of different types than these. For example endothelial cells may be combined with cells that provide other functions such as diagnostic or labeling function. Any type of cell that may form a tissue structure and which may be vascularized using the methods of the disclosed subject matter may be used. These cell types may include differentiated cells rather than the stem cells employed in many of the embodiments. The methods may include a step of exposing undifferentiated cell types to signaling the induces differentiation prior to combining with endothelial cells to form spheroids. Also, any of the embodiments can be modified to include more than one type of cell in addition to the type of cell used to form blood vessels (e.g., endothelial).

The angiogenic growth factors described herein may be replaced or modified by the addition of one or more additional factors including any of Angiogenin; Angiopoietin-1; Angiopoietin-2; Del-1; Fibroblast growth factors: acidic (aFGF) and basic (bFGF); Follistatin; Granulocyte colony-stimulating factor (G-CSF); Hepatocyte growth factor (HGF)/scatter factor (SF); Interleukin-8 (IL-8); Leptin; Midkine; Placental growth factor; Platelet-derived endothelial cell growth factor (PD-ECGF); Platelet-derived growth factor-BB (PDGF-BB); Pleiotrophin (PTN); Progranulin; Proliferin; Transforming growth factor-alpha (TGF-alpha); Transforming growth factor-beta (TGF-beta); Tumor necrosis factor-alpha (TNF-alpha); Vascular endothelial growth factor (VEGF)/vascular permeability factor (VPF); Phorbol esters.

Conditions that may be treated using therapeutic angiogenesis include: Chronic wounds (e.g. diabetic lower extremity ulcers, venous leg ulcerations, pressure ulcers, arterial ulcers); Peripheral arterial disease, critical limb ischemia; Ischemic heart disease; Brain ischemia/stroke; Intestinal ischemia;

Conditions that may be treated (or modeled for diagnostics, research, drug screening etc.) with vascularized engineered tissues include: Liver disease; Soft tissue damage due disease or injury; Muscle loss; Bone damage due to disease or injury; Diabetes; Kidney failure; Pulmonary disease; Genetic diseases causing tissue dysfunction; Cancer; Heart disease.

The endothelial cells described in the embodiments may of various types and sources including: Umbilical vein endothelial cells; Arterial endothelial cells; Venous endothelial cells; Microvascular endothelial cells (e.g. from dermis, fat tissue, brain, retina).

Stem and progenitor cell sources may be used to derive endothelial cells. Examples of such sources include: Embryonic stem cells; Induced pluripotent stem cells; Mesenchymal stem cells (e.g. bone marrow or adipose tissue); Endothelial progenitor cells (blood and bone marrow).

Additional cell types that may be included in spheroids or cell clusters according to any of the embodiments include: Stem and progenitor cells; Embryonic stem cells; Induced pluripotent stem cells; Mesenchymal stem cells (e.g. bone marrow or adipose tissue)

Tissue-specific cells may be differentiated from stem/progenitor cells or from primary cultures at any stage in the disclosed embodiments, including: Fibroblasts; Dermal papilla cells; Keratinocytes; melanocytes; Neurons; Kidney cells; Pancreas cells (islet cells); Hepatocytes; Cardiomyocytes; Skeletal muscle; Smooth muscle; Intestinal epithelial and submucosal cells; Adipocytes; Cancer cells:; Glioblastoma or other brain tumors; Prostate cancer; Cervical cancer; Breast cancer; Liver cancer; Pancreatic cancer; Skin cancer; Bladder cancer; Colon cancer; Ovarian cancer; Testicular cancer.

Although in the embodiments, spheroids (equivalently, clusters) are formed as a first primitive structure for tissue formation, the methods of the disclosed embodiments may be applied to other types of primitive structures. For example, a sheet of cells containing a mix of endothelial and other cells types may be cultured. The tendency of the endothelial cells to concentrate may cause clusters of endothelial cells to arise due to endothelial self-organizing potential combined with initial variations in the initial concentration of the endothelial cells.

Although in embodiments, the spheroids are cultured in the presence of one or more vasculogenic growth factors and then injected or implanted, these embodiments may be modified to culture in the absence of vasculogenic growth factors (or sufficiently depleted of such factors) to cause endothelial cells to concentrate in the center of the spheroids and then immediately inject or implant the spheroids, thereby relying on naturally-occurring vasculogenic signaling to promote the vascular integration of the spheroids. In further embodiments, the implantation or injection may include vasculogenic growth factors in a suspending aqueous solution carrying the spheroids.

While a lumen or vascular precursor has been inferred from observation, it is not evident merely from direct observation that a lumen-shaped structure is formed in vitro in the methods disclosed. However, further development in the presence of vasculogenic growth factors that goes beyond the concentration of endothelial after cultivation without vasculogenic growth factors provides indirect evidence that a lumen structure or vascular precursor forms. The evidence arises from a distinct region of primarily endothelial cells with a largely a defined boundary and sometimes a degree of greater transparency in the center as well as an oblong shape. The evidence also arises from the observation that observable lumens arise from the region of endothelial cell concentration in the spheroids very rapidly (as reported with regard to the various embodiments) combined with the fact that the lumens that are directly observed connect the regions where the endothelial concentration has been directly observed.

Embodiments of the disclosed subject matter can provide treatment for various vascular issues. For example, the disclosed methods can provide a treatment for critical limb ischemia (CLI). A patient may be injected on an outpatient basis with engineered microtissues, each of which contains a blood vessel unit (i.e., a spheroid with an endothelial core). Upon injection, these microtissue units are observed to connect to form a vascular network, which formation occurs faster than the formation of a vascular network by single cell therapies. Multiple injections may be given along the affected limb resulting in a new vascular network that can perfuse the limb and save it from amputation. The therapy may be autologous by using blood vessel units formed from the patient's own cells, for example, harvested with liposuction and injected in-clinic by a clinician.

In any of the embodiments, according to additional embodiments, the culturing in the presence of vasculogenic growth factors may be performed in vitro either before or after releasing from the microwell matrix. In alternative embodiments culturing in the presence of vasculogenic growth factors may be performed initially for a period of time before releasing from the microwells and performed for a further period of time after release in a single vessel, for example in a fluidized bed bioreactor.

Features of the disclosed embodiments may be combined, rearranged, omitted, etc., within the scope of the invention to produce additional embodiments. Furthermore, certain features may sometimes be used to advantage without a corresponding use of other features.

Throughout the specification and claims, there are embodiments in which cell clusters or spheroids are limited to 200 microns. In extensions of the disclosed subject matter any of the embodiments may be expanded to a higher size threshold, for example 300 micron. According to known principles, the size may be extended to up to 400 microns according to further embodiments.

In any of the embodiments identifying microwells, the materials of which the microwells are made may include any type of material that is suitable including other plastics, acrylics, other hydrogels.

Throughout the specification, all references to "embodiments" refer severally to any of the described devices, methods, articles, systems, apparatuses, etc. whether they are described in the specification or defined by the claims. For example, statements stating that "Any of the embodiments may be modified by the inclusion of X," means any of the claims may be so modified and such modified claims form part of the original disclosure.

It is thus apparent that there is provided in accordance with the present disclosure, system, methods, and devices for injectable microtissues. Many alternatives, modifications, and variations are enabled by the present disclosure. While specific embodiments have been shown and described in detail to illustrate the application of the principles of the present invention, it will be understood that the invention may be embodied otherwise without departing from such principles. Accordingly, Applicants intend to embrace all such alternatives, modifications, equivalents, and variations that are within the spirit and scope of the present invention.

REFERENCES

Each of the following documents is incorporated herein by references in its entirety.
1. Novosel, E. C., Kleinhans, C. & Kluger, P. J. Vascularization is the key challenge in tissue engineering. Adv Drug Deliv Rev 63, 300-311 (2011).
2. Dimmeler, S., Ding, S., Rando, T. A. & Trounson, A. Translational strategies and challenges in regenerative medicine. Nat Med 20, 814-821 (2014).
3. Kim, J. J., Hou, L. & Huang, N. F. Vascularization of three-dimensional engineered tissues for regenerative medicine applications. Acta Biomater 41, 17-26 (2016).
4. Sun, X., Altalhi, W. & Nunes, S. S. Vascularization strategies of engineered tissues and their application in cardiac regeneration. Adv Drug Deliv Rev 96, 183-194 (2016).
5. Lovett, M., Lee, K., Edwards, A. & Kaplan, D. L. Vascularization strategies for tissue engineering. Tissue engineering. Part B, Reviews 15, 353-370 (2009).
6. Miller, J. S. et al. Rapid casting of patterned vascular networks for perfusable engineered three-dimensional tissues. Nat Mater 11, 768-774 (2012).
7. Black, A. F., Berthod, F., L'Heureux, N., Germain, L. & Auger, F. A. In vitro reconstruction of a human capillary-like network in a tissue-engineered skin equivalent. FASEB J 12, 1331-1340 (1998).
8. Zisch, A. H. et al. Cell-demanded release of VEGF from synthetic, biointeractive cell ingrowth matrices for vascularized tissue growth. FASEB J 17, 2260-2262 (2003).
9. Mazza, G. et al. Decellularized human liver as a natural 3D-scaffold for liver bioengineering and transplantation. Sci Rep 5, 13079 (2015).
10. Ott, H. C. et al. Perfusion-decellularized matrix: using nature's platform to engineer a bioartificial heart. Nat Med 14, 213-221 (2008).
11. Kang, H. W. et al. A 3D bioprinting system to produce human-scale tissue constructs with structural integrity. Nat Biotechnol 34, 312-319 (2016).
12. Clark, E. R. & Clark, E. L. Microscopic observations on the growth of blood capillaries in the living mammal. American journal of anatomy 64, 251-301 (1939).
13. Lokmic, Z., Stillaert, F., Morrison, W. A., Thompson, E. W. & Mitchell, G. M. An arteriovenous loop in a protected space generates a permanent, highly vascular, tissue-engineered construct. FASEB J 21, 511-522 (2007).
14. Leong, M. F. et al. Patterned prevascularised tissue constructs by assembly of polyelectrolyte hydrogel fibres. Nat Commun 4, 2353 (2013).
15. Haraguchi, Y. S., T.; Sasagawa, T.; Sekine, H.; Sakaguchi, K.; Kikuchi, T.; Sekine, W.; Sekiya, S.; Yamato, M.; Umezu, M.; Okano, T. Fabrication of functional three-dimensional tissues by stacking cell sheets in vitro. Nature Protocols 7, 850-858 (2012).
16. Sekine, H. et al. In vitro fabrication of functional three-dimensional tissues with perfusable blood vessels. Nat Commun 4, 1399 (2013).
17. Sasagawa, T. et al. Design of prevascularized three-dimensional cell-dense tissues using a cell sheet stacking manipulation technology. Biomaterials 31, 1646-1654 (2010).
18. Kolesky, D. B., Homan, K. A., Skylar-Scott, M. A. & Lewis, J. A. Three-dimensional bioprinting of thick vascularized tissues. Proc Natl Acad Sci USA 113, 3179-3184 (2016).
19. Kolesky, D. B. T., R. L.; Gladman, A. S.; Busbee, T. A.; Homan, K. A.; Lewis, J. A. 3D Bioprinting of Vascularized, Heterogeneous Cell-Laden Tissue Constructs. Adv. Mater. 26, 3124-3130 (2014).
20. Mironov, V., Kasyanov, V. & Markwald, R. R. Organ printing: from bioprinter to organ biofabrication line. Curr Opin Biotechnol 22, 667-673 (2011).
21. Mironov, V. et al. Organ printing: tissue spheroids as building blocks. Biomaterials 30, 2164-2174 (2009).
22. Pati, F. et al. Printing three-dimensional tissue analogues with decellularized extracellular matrix bioink. Nat Commun 5, 3935 (2014).
23. Tan, Y. et al. 3D printing facilitated scaffold-free tissue unit fabrication. Biofabrication 6, 024111 (2014).
24. Feiring, A. J. et al. Preventing leg amputations in critical limb ischemia with below-the-knee drug-eluting stents: the PaRADISE (PReventing Amputations using Drug eluting StEnts) trial. J Am Coll Cardiol 55, 1580-1589 (2010).
25. Davies, M. Critical limb ischemia: epidemiology. Methodist DeBakey Cardiovasc J 8, 10-14 (2012).
26. Tongers, J., Roncalli, J. G. & Losordo, D. W. Therapeutic angiogenesis for critical limb ischemia: microvascular therapies coming of age. Circulation 118, 9-16 (2008).
27. Raval, Z. & Losordo, D. W. Cell therapy of peripheral arterial disease: from experimental findings to clinical trials. Circ Res 112, 1288-1302 (2013).
28. Lawall, H., Bramlage, P. & Amann, B. Treatment of peripheral arterial disease using stem and progenitor cell therapy. J Vasc Surg 53, 445-453 (2011).
29. Chen, L., Tredget, E. E., Wu, P. Y. & Wu, Y. Paracrine factors of mesenchymal stem cells recruit macrophages and endothelial lineage cells and enhance wound healing. PLoS One 3, e1886 (2008).
30. Botham, C. M. B., W. L.; Cooke, J. P. Clinical trials of adult stem cell therapy for peripheral artery disease. MdCvJ 9 (2013).
31. Benoit, E., O'Donnell, T. F. & Patel, A. N. Safety and efficacy of autologous cell therapy in critical limb ischemia: a systematic review. Cell Transplant 22, 545-562 (2013).
32. Mirabella, T. et al. 3D-printed vascular networks direct therapeutic angiogenesis in ischaemia. Nature Biomedical Engineering 1, 0083 (2017).
33. Greggio, C. et al. Artificial three-dimensional niches deconstruct pancreas development in vitro. Development 140, 4452-4462 (2013).
34. Lancaster, M. A. et al. Cerebral organoids model human brain development and microcephaly. Nature 501, 373-379 (2013).
35. Lee, J. H. et al. Lung stem cell differentiation in mice directed by endothelial cells via a BMP4-NFATc1-thrombospondin-1 axis. Cell 156, 440-455 (2014).
36. Spence, J. R. et al. Directed differentiation of human pluripotent stem cells into intestinal tissue in vitro. Nature 470, 105-109 (2011).
37. Takasato, M. et al. Directing human embryonic stem cell differentiation towards a renal lineage generates a self-organizing kidney. Nat Cell Biol 16, 118-126 (2014).
38. Takebe, T. et al. Vascularized and functional human liver from an iPSC-derived organ bud transplant. Nature 499, 481-484 (2013).

39. Alajati, A. et al. Spheroid-based engineering of a human vasculature in mice. Nat Methods 5, 439-445 (2008).
40. Nam, K. H., Smith, A. S., Lone, S., Kwon, S. & Kim, D. H. Biomimetic 3D Tissue Models for Advanced High-Throughput Drug Screening. J Lab Autom 20, 201-215 (2015).
41. Walser, R. et al. Generation of co-culture spheroids as vascularisation units for bone tissue engineering. Eur Cell Mater 26, 222-233 (2013).
42. Yap, K. K. et al. Enhanced liver progenitor cell survival and differentiation in vivo by spheroid implantation in a vascularized tissue engineering chamber. Biomaterials 34, 3992-4001 (2013).
43. Dissanayaka, W. L., Zhu, L., Hargreaves, K. M., Jin, L. & Zhang, C. Scaffold-free Prevascularized Microtissue Spheroids for Pulp Regeneration. J Dent Res 93, 1296-1303 (2014).
44. Verseijden, F. et al. Prevascular structures promote vascularization in engineered human adipose tissue constructs upon implantation. Cell Transplant 19, 1007-1020 (2010).
45. Meyer, U. et al. Cartilage defect regeneration by ex vivo engineered autologous microtissue--preliminary results. In Vivo 26, 251-257 (2012).
46. Sutherland, R. M., McCredie, J. A. & Inch, W. R. Growth of multicell spheroids in tissue culture as a model of nodular carcinomas. J Natl Cancer Inst 46, 113-120 (1971).
47. Akiyama, M., Nonomura, H., Kamil, S. H. & Ignotz, R. A. Periosteal cell pellet culture system: a new technique for bone engineering. Cell Transplant 15, 521-532 (2006).
48. Liu, J. et al. Functional three-dimensional HepG2 aggregate cultures generated from an ultrasound trap: comparison with HepG2 spheroids. J Cell Biochem 102, 1180-1189 (2007).
49. Okochi, M. et al. Three-dimensional cell culture array using magnetic force-based cell patterning for analysis of invasive capacity of BALB/3T3/v-src. Lab Chip 9, 3378-3384 (2009).
50. Chung, H. J. & Park, T. G. Injectable cellular aggregates prepared from biodegradable porous microspheres for adipose tissue engineering. Tissue Eng Part A 15, 1391-1400 (2009).
51. Griffin, D. R., Weaver, W. M., Scumpia, P. O., Di Carlo, D. & Segura, T. Accelerated wound healing by injectable microporous gel scaffolds assembled from annealed building blocks. Nat Mater 14, 737-744 (2015).
52. Huebsch, N. et al. Matrix elasticity of void-forming hydrogels controls transplanted-stem-cell-mediated bone formation. Nat Mater 14, 1269-1277 (2015).
53. Jeong, G. S. et al. Viscoelastic lithography for fabricating self-organizing soft micro-honeycomb structures with ultra-high aspect ratios. Nat Commun 7, 11269 (2016).
54. Tung, Y. C. et al. High-throughput 3D spheroid culture and drug testing using a 384 hanging drop array. Analyst 136, 473-478 (2011).
55. Frey, O., Misun, P. M., Fluri, D. A., Hengstler, J. G. & Hierlemann, A. Reconfigurable microfluidic hanging drop network for multi-tissue interaction and analysis. Nat Commun 5, 4250 (2014).
56. Ehsan, S. M., Welch-Reardon, K. M., Waterman, M. L., Hughes, C. C. & George, S. C. A three-dimensional in vitro model of tumor cell intravasation. Integr Biol (Camb) 6, 603-610 (2014).
57. Yuhas, J. M., Li, A. P., Martinez, A. O. & Ladman, A. J. A simplified method for production and growth of multicellular tumor spheroids. Cancer Res 37, 3639-3643 (1977).
58. Metzger, W. et al. The liquid overlay technique is the key to formation of co-culture spheroids consisting of primary osteoblasts, fibroblasts and endothelial cells. Cytotherapy 13, 1000-1012 (2011).
59. Wenger, A. et al. Development and characterization of a spheroidal coculture model of endothelial cells and fibroblasts for improving angiogenesis in tissue engineering. Cells Tissues Organs 181, 80-88 (2005).
60. Chen, Y. C., Lou, X., Zhang, Z., Ingram, P. & Yoon, E. High-Throughput Cancer Cell Sphere Formation for Characterizing the Efficacy of Photo Dynamic Therapy in 3D Cell Cultures. Sci Rep 5, 12175 (2015).
61. Liu, T., Winter, M. & Thierry, B. Quasi-spherical microwells on superhydrophobic substrates for long term culture of multicellular spheroids and high throughput assays. Biomaterials 35, 6060-6068 (2014).
62. Ozawa, F. et al. Alginate gel microwell arrays using electrodeposition for three-dimensional cell culture. Lab Chip 13, 3128-3135 (2013).
63. Li, N., Schwartz, M. & Ionescu-Zanetti, C. PDMS Compound Adsorption in Context. J Biomol Screen 14, 194-202 (2009).
64. Toepke, M. W. & Beebe, D. J. PDMS absorption of small molecules and consequences in microfluidic applications. Lab Chip 6, 1484-1486 (2006).
65. Gillette, B. M. et al. In situ collagen assembly for integrating microfabricated three-dimensional cell-seeded matrices. Nat Mater 7, 636-640 (2008).
66. Gillette, B. M. et al. Engineering extracellular matrix structure in 3D multiphase tissues. Biomaterials 32, 8067-8076 (2011).
67. Steffens, L., Wenger, A., Stark, G. B. & Finkenzeller, G. In vivo engineering of a human vasculature for bone tissue engineering applications. J Cell Mol Med 13, 3380-3386 (2009).
68. Walser, R. M., W.; Görg, A.; Pohlemann, T.; Menger, M. D.; Laschke, M. W. Generation of co-culture spheroids as vascularisation units for bone tissue engineering. European cells & materials 26, 222-233 (2013).
69. Rouwkema, J. D. B., J.; Van Blitterswijk, C. A. Endothelial Cells Assemble into a 3-Dimensional Prevascular Network in a Bone Tissue Engineering Construct. Tissue Engineering 12, 2685-2693 (2006).
70. Brenes, R. A. et al. Toward a mouse model of hind limb ischemia to test therapeutic angiogenesis. J Vasc Surg 56, 1669-1679; discussion 1679 (2012).
71. Goto, T. F., N.; Aki, A.; Kanabuchi, K.; Kimura, K.; Taira, H.; Tanaka, E.; Wakana, N.; Mori, H.; Inoue, H. Search for appropriate experimental methods to create stable hind-limb ischemia in mouse. Tokai J Exp Clin Med 20, 128-132 (2006).
72. Briers, J. D. Laser Doppler, speckle and related techniques for blood perfusion mapping and imaging. Physiol. Meas. 22, R35-R66 (2001).
73. Fennema, E., Rivron, N., Rouwkema, J., van Blitterswijk, C. & de Boer, J. Spheroid culture as a tool for creating 3D complex tissues. Trends Biotechnol 31, 108-115 (2013).
74. White, S. M. et al. Implanted cell-dense prevascularized tissues develop functional vasculature that supports reoxygenation after thrombosis. Tissue Eng Part A 20, 2316-2328 (2014).

75. Wang, Y. C., Q.; Yuan, F. Alginate encapsulation is a highly reproducible method for tumor cell implantation in dorsal skinfold chambers. BioTechniques 39, 834-839 (2005).
76. Fleming, P. A. et al. Fusion of uniluminal vascular spheroids: a model for assembly of blood vessels. Dev Dyn 239, 398-406 (2010).
77. Huang, W. H. et al. Mesenchymal stem cells promote growth and angiogenesis of tumors in mice. Oncogene 32, 4343-4354 (2013).
78. Iwase, T. et al. Comparison of angiogenic potency between mesenchymal stem cells and mononuclear cells in a rat model of hindlimb ischemia. Cardiovasc Res 66, 543-551 (2005).
79. Laschke, M. W., Vollmar, B. & Menger, M. D. The dorsal skinfold chamber: window into the dynamic interaction of biomaterials with their surrounding host tissue. European cells & materials 22, 147-164; discussion 164-147 (2011).
80. Palmer, G. M., Fontanella, A. N., Shan, S. & Dewhirst, M. W. High-resolution in vivo imaging of fluorescent proteins using window chamber models. Methods Mol Biol 872, 31-50 (2012).
81. Ponticorvo, A. & Dunn, A. K. How to build a Laser Speckle Contrast Imaging (LSCI) system to monitor blood flow. J Vis Exp (2010).
82. Boas, D. A. & Dunn, A. K. Laser speckle contrast imaging in biomedical optics. J Biomed Opt 15, 011109 (2010).

The invention claimed is:

1. An injectable microtissue comprising:
a plurality of spheroids, each comprising a plurality of cells of a first cell type and a plurality of cells of a second cell type, the first cell type being endothelial cells that are concentrated in an interior core region of each spheroid, wherein the second cell type is one of mesenchymal stem cells, smooth muscle cells, and dermal fibroblasts;
the plurality of spheroids being free of vascular interconnections therebetween and suspended in an injectable medicament, and
wherein the injectable microtissue is free of brown adipose tissue,
wherein the injectable microtissue is suitable for therapeutic injection in a human patient,
wherein a majority of the spheroids have diameters less than 200 µm,
wherein the endothelial cells concentrated in an interior region define a distinct structure with discernable boundaries and consisting essentially of said endothelial cells, and
wherein the endothelial cells are vascular endothelial cells and the distinct structure is a blood vessel precursor.

2. The microtissue of claim 1, wherein the plurality of cells of the second type form a shell that can withstand the shear strain and stress of injection through a 27 ga (0.27 mm) or 30 ga (0.159 mm) cannula at rates of 0.1 to 2 mL/min.

3. An injectable microtissue comprising:
a plurality of spheroids, each comprising a plurality of cells of a first cell type and a plurality of cells of a second cell type, the first cell type being endothelial cells that are concentrated in an interior core region of each spheroid;
the plurality of spheroids being free of vascular interconnections therebetween and suspended in an injectable medicament,
wherein the injectable microtissue is free of brown adipose tissue,
wherein the injectable microtissue is suitable for therapeutic injection in a human patient,
wherein a majority of the spheroids have diameters less than 200 µm, and wherein the second cell type is mesenchymal stem cells.

4. A method of treating a patient, the method comprising:
injecting an injectable microtissue into a patient such that a new vascular network is formed therein with the endothelial cell core regions of the spheroids as nodes, wherein the injectable microtissue comprises:
a plurality of spheroids, each comprising a plurality of cells of a first cell type and a plurality of cells of a second cell type, the first cell type being endothelial cells that are concentrated in an interior core region of each spheroid, wherein the second cell type is one of mesenchymal stem cells, smooth muscle cells, and dermal fibroblasts;
the plurality of spheroids being free of vascular interconnections therebetween and suspended in an injectable medicament,
wherein the injectable microtissue is free of brown adipose tissue,
wherein the injectable microtissue is suitable for therapeutic injection in a human patient,
wherein a majority of the spheroids have diameters less than 200 µm, and
wherein the endothelial cells concentrated in an interior region define a distinct structure with discernable boundaries and consisting of said endothelial cells, the endothelial cells are vascular endothelial cells, and the distinct structure is a blood vessel precursor.

5. The method of claim 4, wherein the injecting is effective to treat a condition of ischemia.

6. The method of claim 4, wherein the injecting is performed at multiple locations spaced apart along a limb or other anatomical feature of the patient.

7. The microtissue of claim 1, wherein the injectable microtissue is free of growth factors.

8. A method of treating a patient, the method comprising:
injecting an injectable microtissue into a patient such that a new vascular network is formed therein with the endothelial cell core regions of the spheroids as nodes, wherein the injectable microtissue comprises:
a plurality of spheroids, each comprising a plurality of cells of a first cell type and a plurality of cells of a second cell type, the first cell type being endothelial cells that are concentrated in an interior core region of each spheroid;
the plurality of spheroids being free of vascular interconnections therebetween and suspended in an injectable medicament,
wherein the injectable microtissue is free of brown adipose tissue,
wherein the injectable microtissue is suitable for therapeutic injection in a human patient,
wherein a majority of the spheroids have diameters less than 200 µm, and
wherein the second cell type is mesenchymal stem cells.

9. The method of claim 8, wherein the injecting is effective to treat a condition of ischemia.

10. The method of claim 8, wherein the injecting is performed at multiple locations spaced apart along a limb or other anatomical feature of the patient.

* * * * *